(12) United States Patent
Jeon et al.

(10) Patent No.: US 11,453,682 B2
(45) Date of Patent: Sep. 27, 2022

(54) CONDENSED-CYCLIC COMPOUND AND ORGANIC LIGHT-EMITTING DEVICE INCLUDING THE SAME

(71) Applicant: Samsung Electronics Co., Ltd., Suwon-si (KR)

(72) Inventors: Soonok Jeon, Suwon-si (KR); Yeonsook Chung, Seoul (KR); Eunsuk Kwon, Suwon-si (KR); Jhunmo Son, Yongin-si (KR); Hasup Lee, Seoul (KR); Sooghang Ihn, Hwaseong-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 355 days.

(21) Appl. No.: 16/580,503

(22) Filed: Sep. 24, 2019

(65) Prior Publication Data
US 2020/0317694 A1 Oct. 8, 2020

(30) Foreign Application Priority Data

Apr. 3, 2019 (KR) .................. 10-2019-0039099

(51) Int. Cl.
*C07D 519/00* (2006.01)
*H01L 51/00* (2006.01)
*H01L 51/50* (2006.01)
*H01L 51/52* (2006.01)

(52) U.S. Cl.
CPC ........ *C07D 519/00* (2013.01); *H01L 51/0067* (2013.01); *H01L 51/0072* (2013.01); *H01L 51/5012* (2013.01); *H01L 51/5056* (2013.01); *H01L 51/5072* (2013.01); *H01L 51/5092* (2013.01); *H01L 51/5206* (2013.01); *H01L 51/5221* (2013.01)

(58) Field of Classification Search
CPC .................................................... C07D 519/00
See application file for complete search history.

(56) References Cited

U.S. PATENT DOCUMENTS

| 2014/0252280 A1 | 9/2014 | Schaefer et al. |
| 2016/0072077 A1 | 3/2016 | Ito et al. |
| 2018/0086763 A1 | 3/2018 | Raimann et al. |

FOREIGN PATENT DOCUMENTS

| CN | 109651406 A | * | 4/2019 |
| KR | 1020150058083 A | | 5/2015 |
| KR | 1020160029187 A | | 3/2016 |

OTHER PUBLICATIONS

Computer-generated English-language translation of CN-109651406-A.*

* cited by examiner

*Primary Examiner* — Vu A Nguyen
(74) *Attorney, Agent, or Firm* — Cantor Colburn LLP

(57) ABSTRACT

A condensed-cyclic compound represented by Formula 1 and an organic light-emitting device including the same:

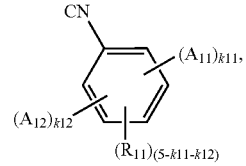

Formula 1 wherein, in Formula 1,
$A_{11}$ is a group represented by Formulae 2-1 to 2-3 as described herein.

17 Claims, 1 Drawing Sheet

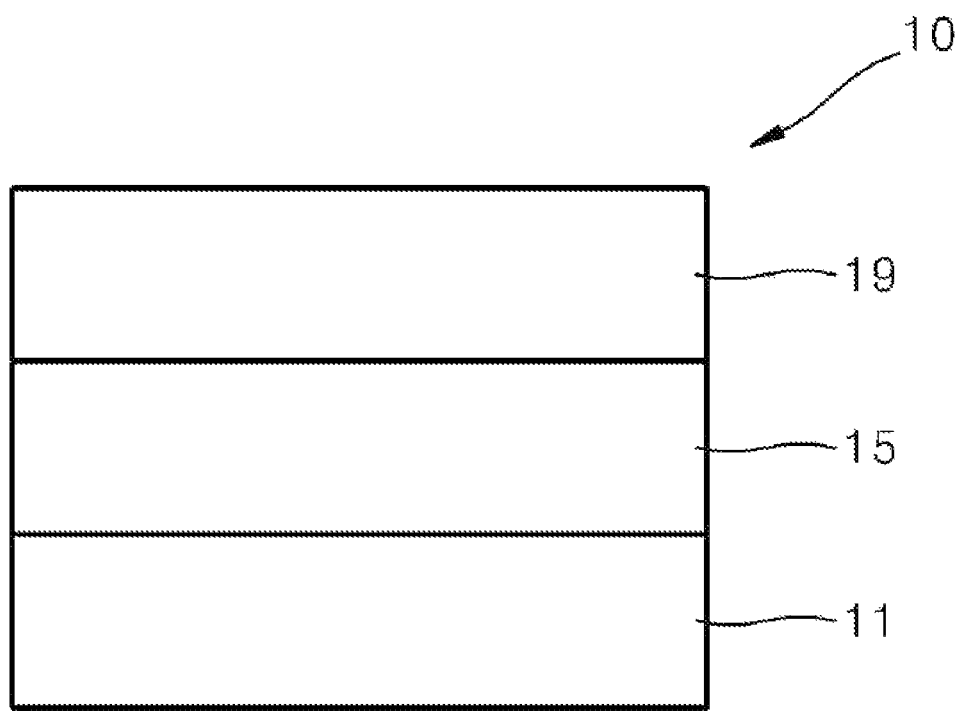

CONDENSED-CYCLIC COMPOUND AND ORGANIC LIGHT-EMITTING DEVICE INCLUDING THE SAME

CROSS-REFERENCE TO RELATED APPLICATION

This application claims the priority to and the benefit of Korean Patent Application No. 10-2019-0039099, filed on Apr. 3, 2019, in the Korean Intellectual Property Office, and all the benefits accruing therefrom under 35 U.S.C. § 119, the contents of which in its entirety are herein incorporated by reference.

BACKGROUND

1. Field

One or more embodiments relate to a condensed-cyclic compound and an organic light-emitting device including the same.

2. Detailed Description of the Related Art

Organic light-emitting devices are self-emissive devices and, compared with devices of the related art, have a wide viewing angle, a high contrast ratio, and a short response time, and exhibit excellent characteristics in terms of luminance, driving voltage, and response speed.

In an example, an organic light-emitting device includes an anode, a cathode, and an organic layer between the anode and the cathode, wherein the organic layer includes an emission layer. A hole transport region may be between the anode and the emission layer, and an electron transport region may be between the emission layer and the cathode. Holes provided from the anode may move toward the emission layer through the hole transport region, and electrons provided from the cathode may move toward the emission layer through the electron transport region. The holes and the electrons, which are carriers, recombine in the emission layer to produce excitons. These excitons transition from an excited state to a ground state, thereby generating light.

SUMMARY

One or more embodiments include a condensed-cyclic compound having excellent delayed fluorescence emission characteristics and an organic light-emitting device that has high efficiency and/or a long lifespan due to the inclusion of the condensed-cyclic compound.

Additional aspects will be set forth in part in the description which follows and, in part, will be apparent from the description, or may be learned by practice of the presented embodiments.

According to one or more embodiments, a condensed-cyclic compound represented by Formula 1 is provided:

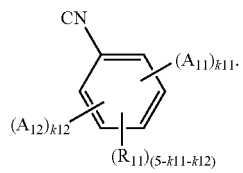

Formula 1

In Formula 1,
$A_{11}$ may be a group represented by any of Formulae 2-1 to 2-3;

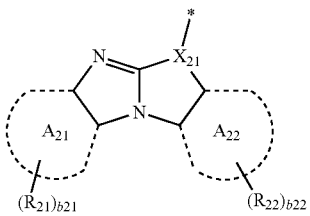

Formula 2-1

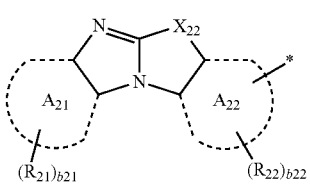

Formula 2-2

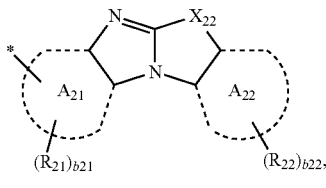

Formula 2-3 wherein, in Formulae 2-1 to 2-3;
$X_{21}$ may be N or $C(R_{23})$;
$X_{22}$ may be $N(R_{24})$, $C(R_{24})(R_{25})$, O, or S;
ring $A_{21}$ and ring $A_{22}$ may each independently be a $C_5$-$C_{60}$ carbocyclic group or a $C_1$-$C_{60}$ heterocyclic group;
$R_{21}$ to $R_{25}$ may each independently be hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$),
b21 and b22 may each independently be 1, 2, 3, 4, 5, 6, 7, 8, 9, or 10;
* indicates a binding site to a neighboring atom;
k11 indicates an integer from 1 to 5;
$A_{12}$ may be a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_7$-$C_{60}$ alkylaryl group, a substituted or unsubstituted $C_1$-$C_{60}$ heteroaryl group, a substituted or unsubstituted $C_2$-$C_{60}$ alkylheteroaryl group, a substituted or unsubstituted monovalent non-aromatic condensed polycyclic group, or a substituted or unsubstituted monovalent non-aromatic condensed heteropolycyclic group;

k12 may be an integer from 0 to 5;

the sum of k11 and k12 may be 4 or 5;

$R_{11}$ may be hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), and $Q_1$ to $Q_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with deuterium, —F, a cyano group, a $C_1$-$C_{60}$ alkyl group, a $C_6$-$C_{60}$ aryl group, or a combination thereof, a $C_6$-$C_{60}$ aryl group substituted with deuterium, —F, a cyano group, a $C_1$-$C_{60}$ alkyl group, a $C_6$-$C_{60}$ aryl group, or a combination thereof.

BRIEF DESCRIPTION OF THE DRAWING

These and/or other aspects will become apparent and more readily appreciated from the following description of the embodiments, taken in conjunction with FIGURE which shows a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer, or section from another element, component, region, layer, or section. Thus, "a first element," "component," "region," "layer," or "section" discussed below could be termed a second element, component, region, layer, or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "At least one" is not to be construed as limiting "a" or "an." "Or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the FIGURES. It will be understood that relative terms are intended to encompass different orientations of the device in addition to the orientation depicted in the FIGURES. For example, if the device in one of the FIGURES is turned over, elements described as being on the "lower" side of other elements would then be oriented on "upper" sides of the other elements. The exemplary term "lower," can therefore, encompasses both an orientation of "lower" and "upper," depending on the particular orientation of the FIGURE. Similarly, if the device in one of the FIGURES is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

The condensed-cyclic compound may be represented by Formula 1:

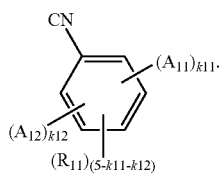

Formula 1

In Formula 1, $A_{11}$ may be a group represented by any of Formulae 2-1 to 2-3:

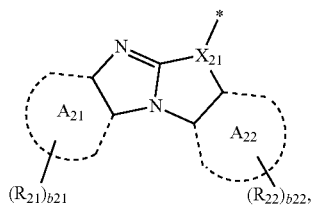

Formula 2-1

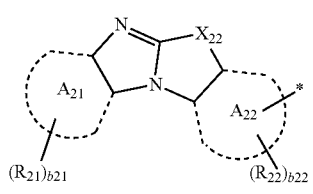

Formula 2-2

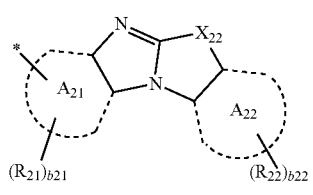

Formula 2-3 wherein $X_{21}$, $X_{22}$, $A_{21}$, $A_{22}$, $R_{21}$, $R_{22}$, b21, and b22 in Formulae 2-1 to 2-3 may each independently be understood by referring to the description provided below; and
* indicates a binding site to a neighboring atom.

In Formulae 2-1 to 2-3, $X_{21}$ may be N or $C(R_{23})$, wherein $R_{23}$ may be understood by referring to the description provided below.

In Formulae 2-1 to 2-3, $X_{22}$ may be $N(R_{24})$, $C(R_{24})(R_{25})$, O, or S, wherein $R_{24}$ and $R_{25}$ may each independently be understood by referring to the description provided below.

For example, in Formulae 2-1 to 2-3,
$X_{21}$ may be N; and
$X_{22}$ may be $N(R_{24})$, O, or S, but embodiments of the present disclosure are not limited thereto.

In Formulae 2-1 to 2-3, ring $A_{21}$ and ring $A_{22}$ may each independently be a $C_5$-$C_{60}$ carbocyclic group or a $C_1$-$C_{60}$ heterocyclic group.

For example, ring $A_{21}$ and ring $A_{22}$ in Formulae 2-1 to 2-3 may each independently be a benzene group, a naphthalene group, an anthracene group, a phenanthrene group, a phenalene group, a triphenylene group, a pyridine group, a pyrimidine group, a pyrazine group, a pyridazine group, a triazine group, a quinoline group, an isoquinoline group, a 2,6-naphthyridine group, a 1,8-naphthyridine group, a 1,5-naphthyridine group, a 1,6-naphthyridine group, a 1,7-naphthyridine group, a 2,7-naphthyridine group, a quinoxaline group, a phthalazine group, a quinazoline group, a phenanthroline group, a benzoquinoline group, a benzoisoquinoline group, a benzoquinoxaline group, a benzoquinazoline group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an indenopyridine group, an indolopyridine group, a benzofuropyridine group, a benzothienopyridine group, a benzosilolopyridine group, an indenopyrimidine group, an indolopyrimidine group, a benzofuropyrimidine group, a benzothienopyrimidine group, or a benzosilolopyrimidine group, but embodiments of the present disclosure are not limited thereto.

In one embodiment, ring $A_{21}$ and ring $A_{22}$ in Formulae 2-1 to 2-3 may each independently be a benzene group or a naphthalene group, but embodiments of the present disclosure are not limited thereto.

In one or more embodiments, ring $A_{21}$ and ring $A_{22}$ in Formulae 2-1 to 2-3 may each independently be a benzene group, but embodiments of the present disclosure are not limited thereto.

In Formulae 2-1 to 2-3, $R_{21}$ to $R_{25}$ may each independently be hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —$Si(Q_1)(Q_2)$ ($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$($Q_1$), —P(=O)($Q_1$)($Q_2$), or —P(=S)($Q_1$)($Q_2$), wherein $Q_1$ to $Q_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with deuterium, —F, a cyano group, a $C_1$-$C_{60}$ alkyl group, a $C_6$-$C_{60}$ aryl group, or a combination thereof, or a $C_6$-$C_{60}$ aryl group substituted with deuterium, —F, a cyano group, a $C_1$-$C_{60}$ alkyl group, a $C_6$-$C_{60}$ aryl group, or a combination thereof.

For example, $R_{21}$ to $R_{25}$ in Formulae 2-1 to 2-3 may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a pyridinyl group, a pyrimidinyl group, or a combination thereof;

a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each substituted with deuterium, —F, —Cl, —Br, —I, —CD$_3$, —CD$_2$H, —CDH$_2$, —CF$_3$, —CF$_2$H, —CFH$_2$, a hydroxyl group, a nitro group, a cyano group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyridinyl group substituted with a phenyl group, a pyrazinyl group, a pyrazinyl group substituted with a phenyl group a pyrimidinyl group, a pyrimidinyl group substituted with a phenyl group, a pyridazinyl group, a pyridazinyl group substituted with a phenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a triazinyl group substituted with a phenyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si($Q_{11}$)($Q_{12}$)($Q_{13}$), —B($Q_{11}$)($Q_{12}$), —N($Q_{11}$)($Q_{12}$), or a combination thereof; or —Si($Q_1$)($Q_2$)($Q_3$), —B($Q_1$)($Q_2$), or —N($Q_1$)($Q_2$), and $Q_1$ to $Q_3$ and $Q_{11}$ to $Q_{13}$ may each independently be selected from:

a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a phenyl ($C_1$-$C_{20}$ alkyl) group, or a naphthyl group; or a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group substituted with deuterium, a phenyl group, or a combination thereof, but embodiments of the present disclosure are not limited thereto.

In one embodiment, $R_{21}$ to $R_{25}$ in Formulae 2-1 to 2-3 may each independently be hydrogen, deuterium, —F, a cyano group, a nitro group, —$CH_3$, —$CD_3$, —$CD_2H$, —$CDH_2$, —$CF_3$, —$CF_2H$, —$CFH_2$, groups represented by Formulae 9-1 to 9-27, groups represented by Formulae 9-1 to 9-27 in which a hydrogen is substituted with deuterium, groups represented by Formulae 10-1 to 10-226, —$Si(Q_1)(Q_2)(Q_3)$, —$B(Q_1)(Q_2)$, or —$N(Q_1)(Q_2)$, but embodiments of the present disclosure are not limited thereto:

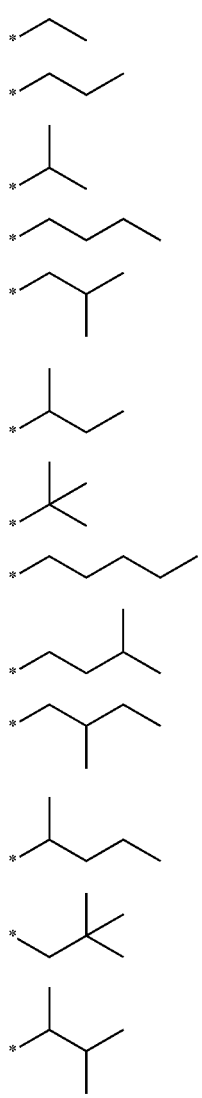

9-1
9-2
9-3
9-4
9-5
9-6
9-7
9-8
9-9
9-10
9-11
9-12
9-13

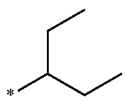

9-14

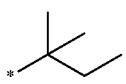

9-15

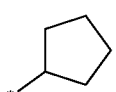

9-16

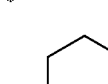

9-17

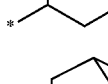

9-18

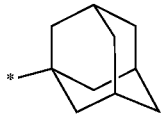

9-19

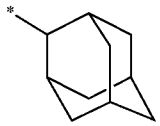

9-20

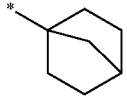

9-21

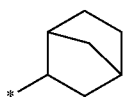

9-22

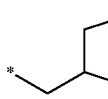

9-23

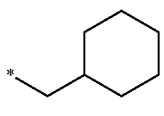

9-24

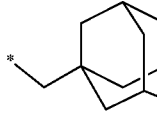

9-25

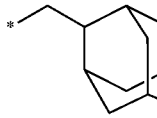

9-26

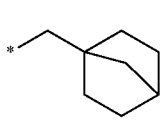

9-27

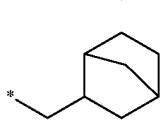

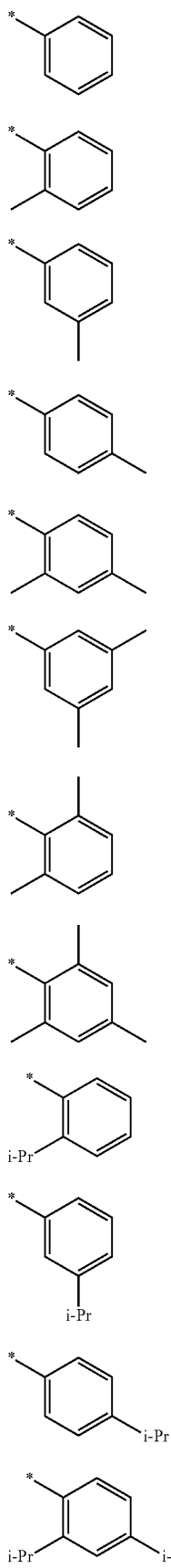
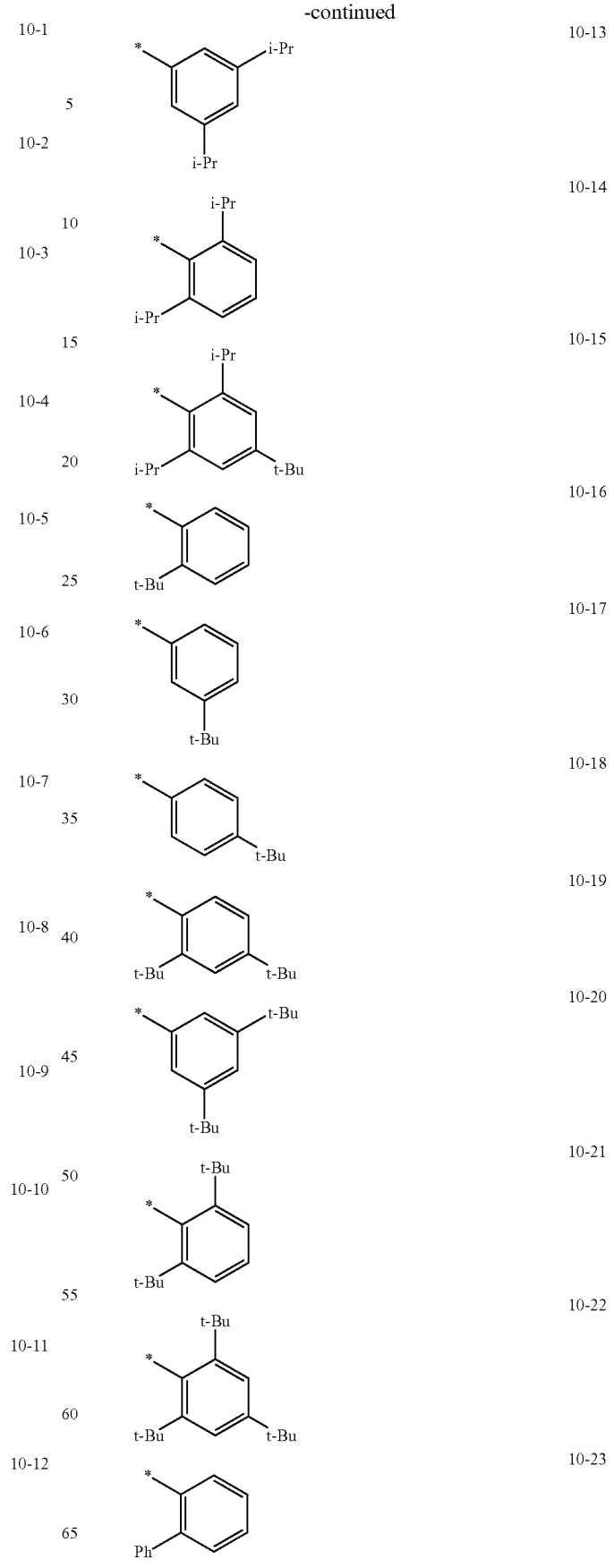

-continued
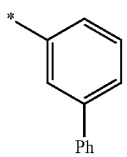
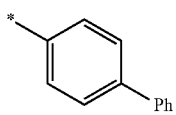
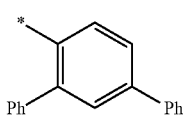
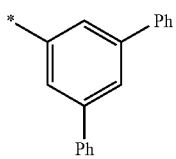
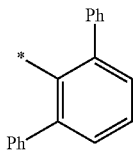
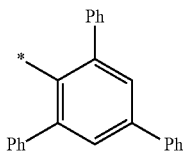
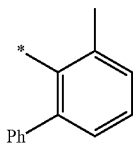
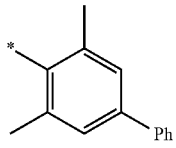
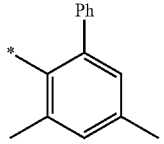
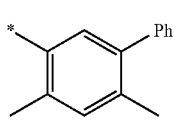
-continued
10-24
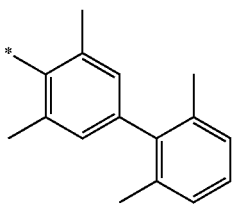
10-25
10-26
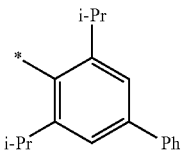
10-27
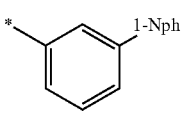
10-28
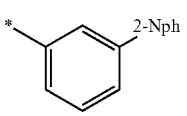
10-29
10-30
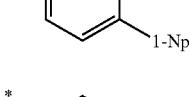
10-31
10-32
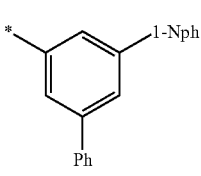
10-33
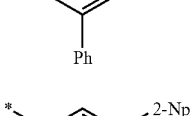
10-34
10-35
10-36
10-37
10-38
10-39
10-40
10-41
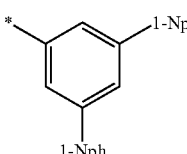
10-42
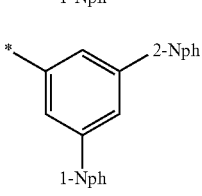
10-43

-continued
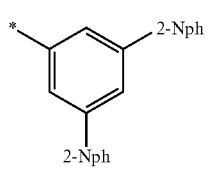
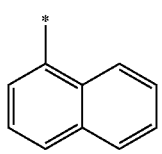
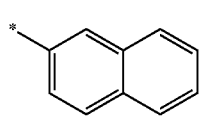
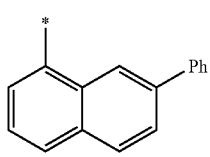
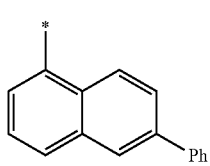
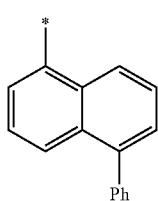
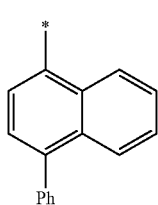
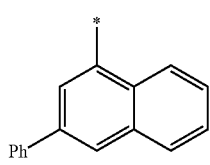
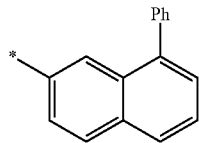
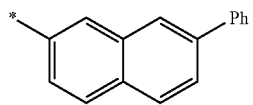
-continued
10-44
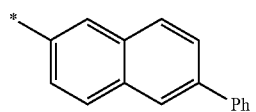
10-45
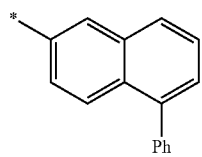
10-46
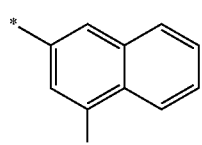
10-47
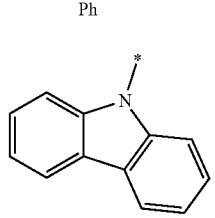
10-48
10-49
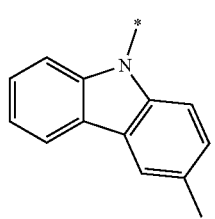
10-50
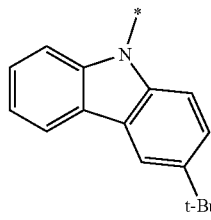
10-51
10-52
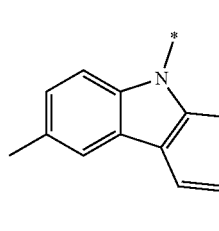
10-53
10-54
10-55
10-56
10-57
10-58
10-59
10-60
10-61
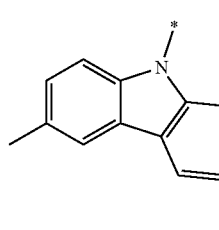

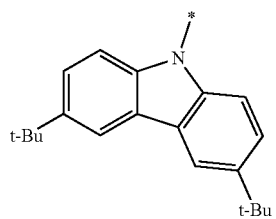
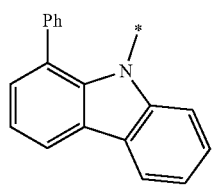
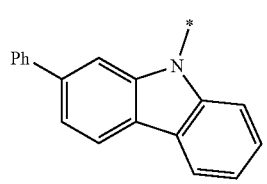
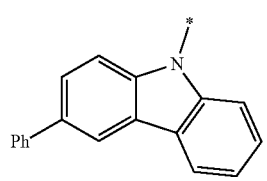
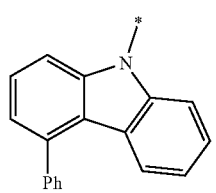
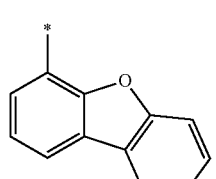
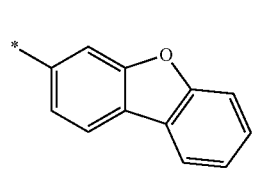
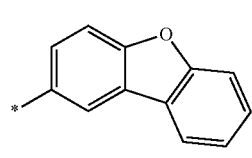
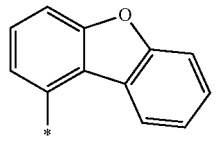
10-62
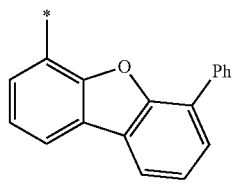
10-63
10-64
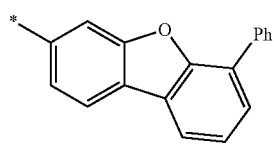
10-65
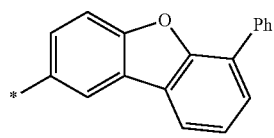
10-66
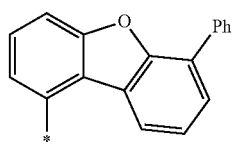
10-67
10-68
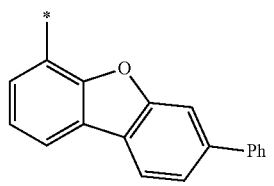
10-69
10-70
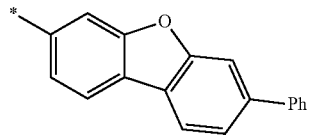
10-71
10-72
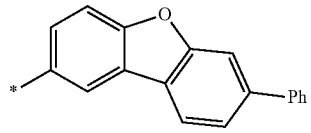
10-73
10-74
10-75
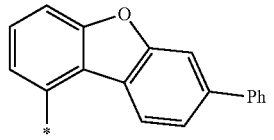
10-76
10-77
10-78
10-79
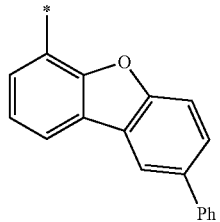

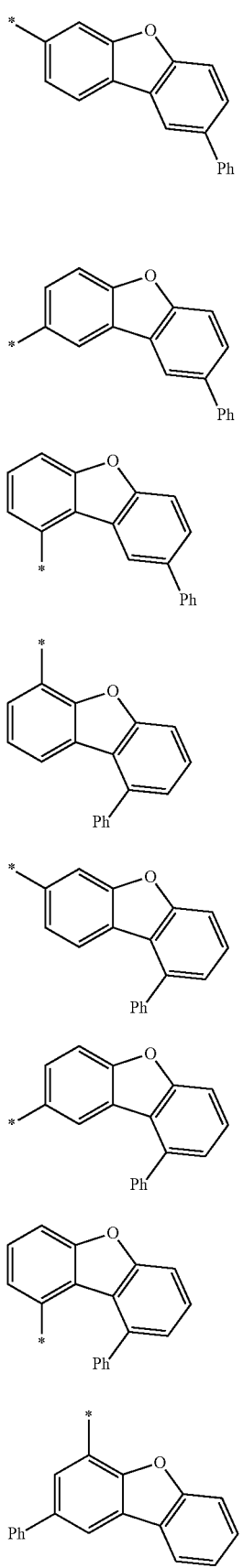
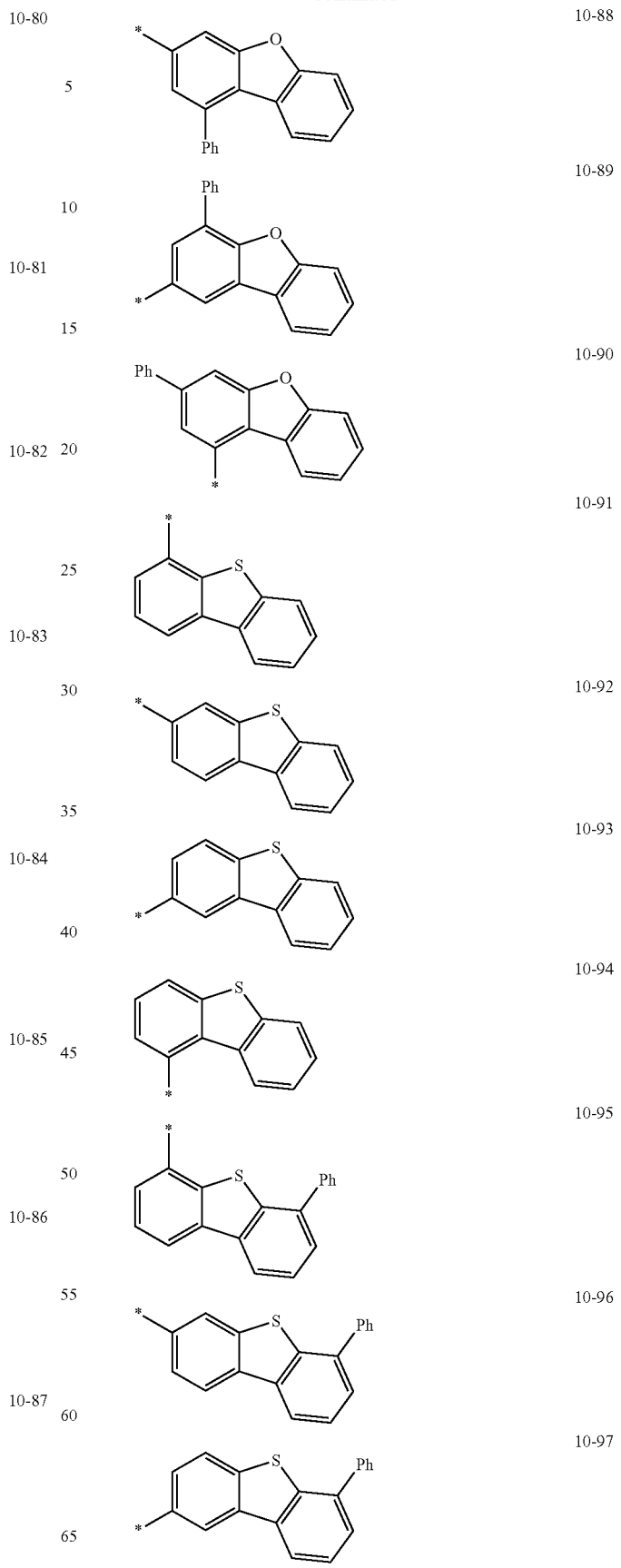

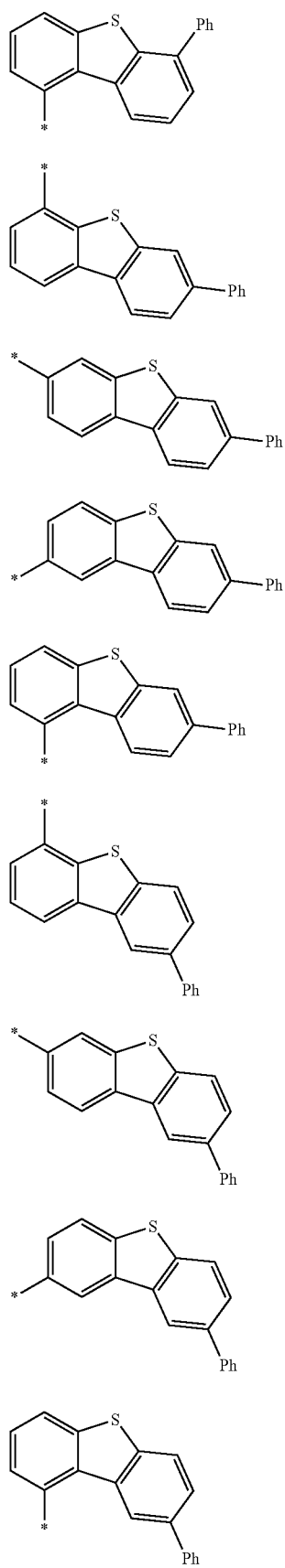
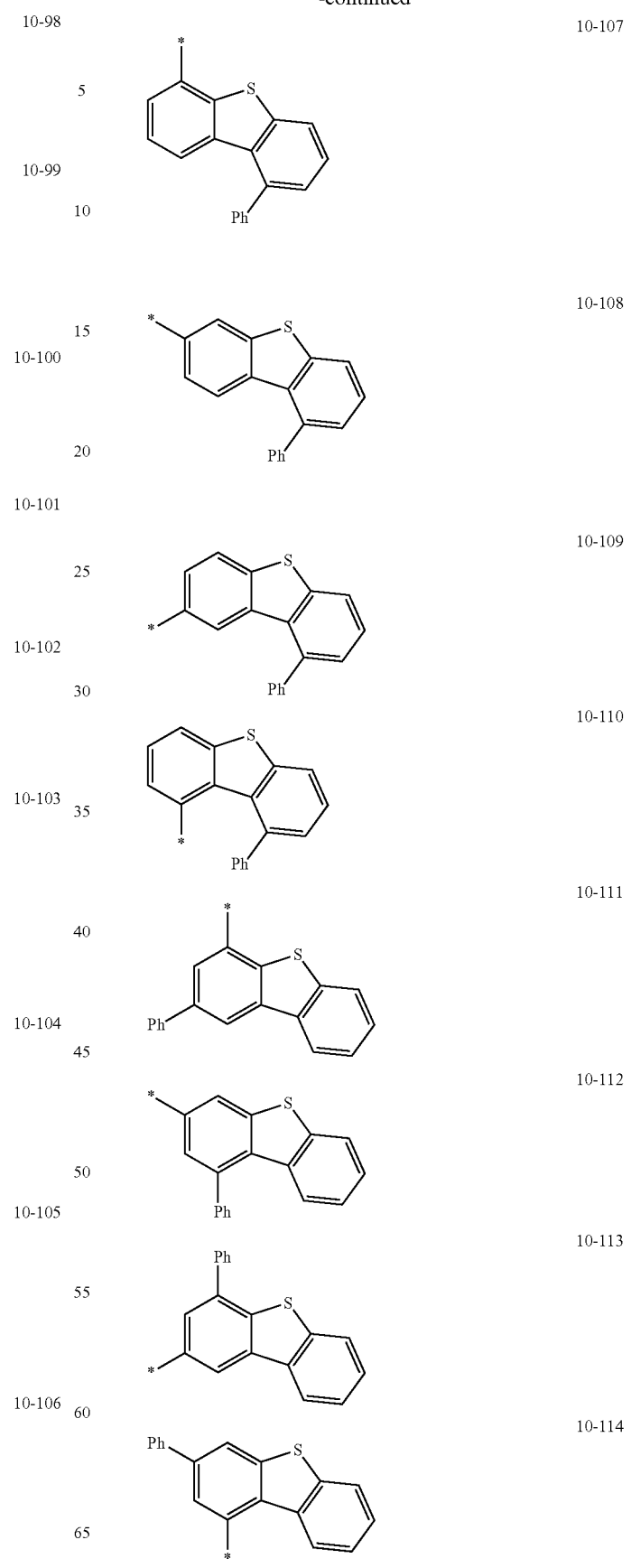

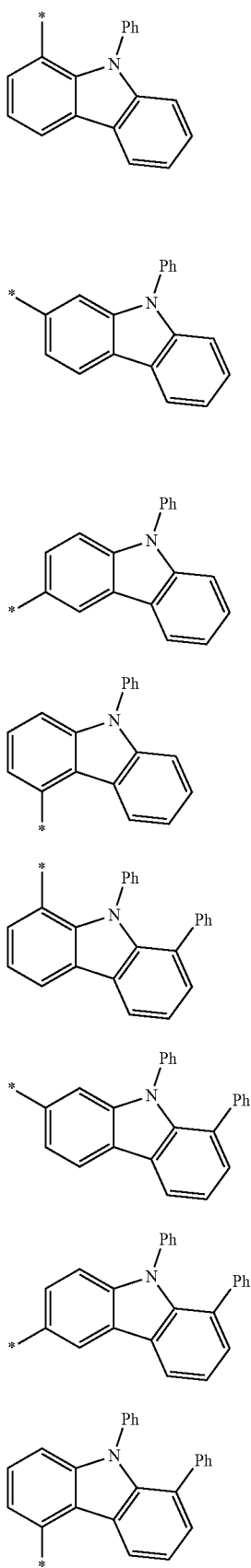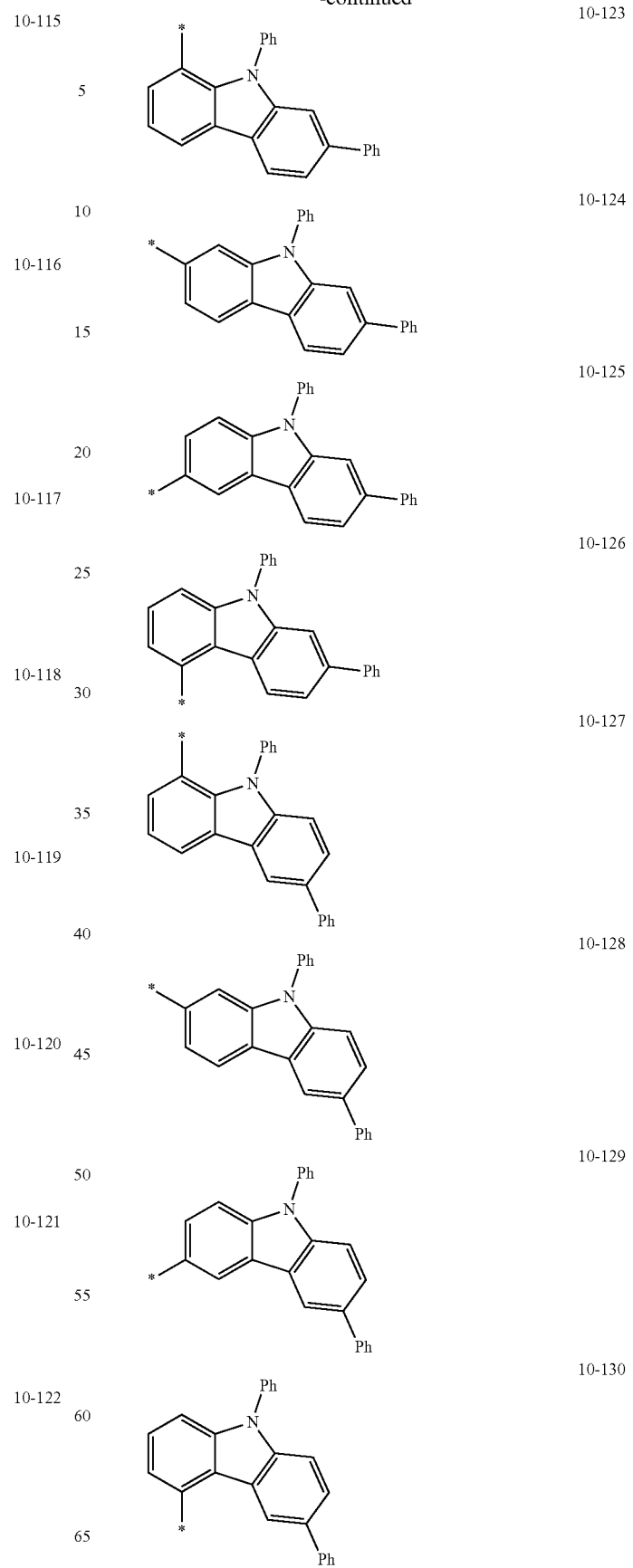

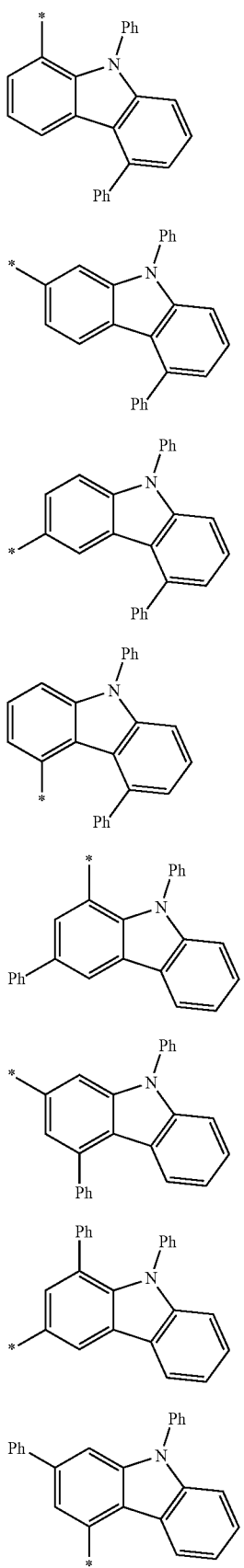
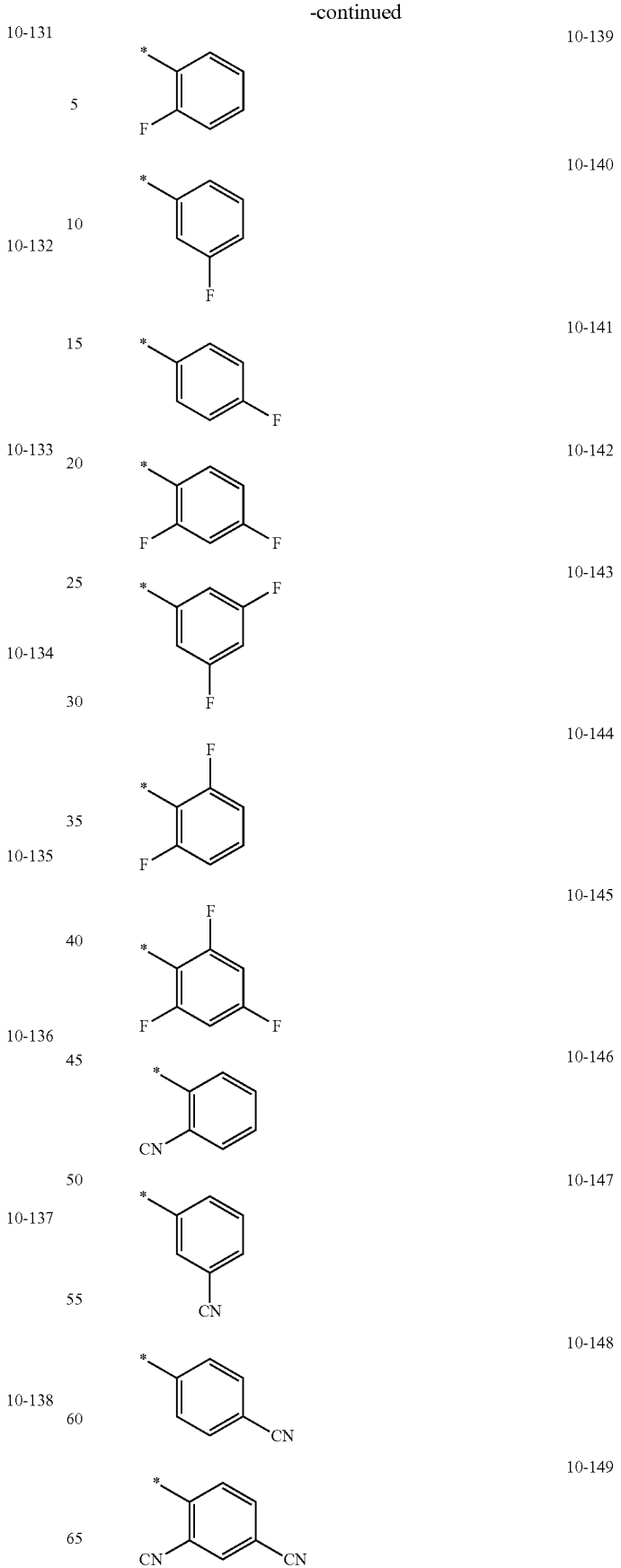

10-150 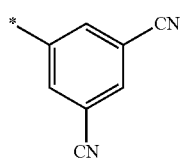
10-151 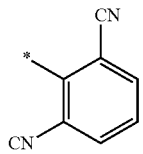
10-152 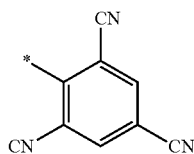
10-153 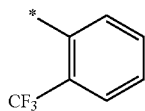
10-154 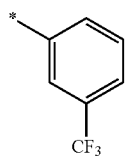
10-155 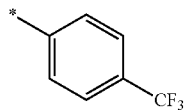
10-156 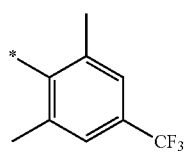
10-157 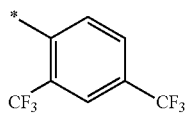
10-158 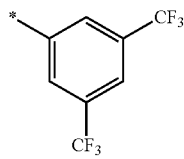
10-159 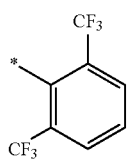
10-160 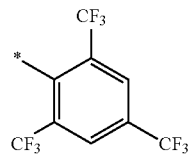
10-161 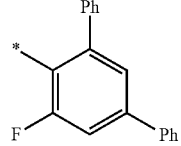
10-162 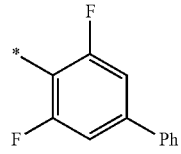
10-163 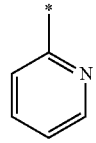
10-164 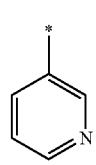
10-165 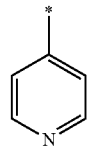
10-166 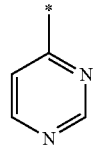
10-167 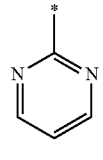
10-168 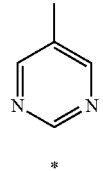
10-169 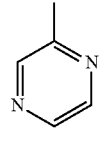

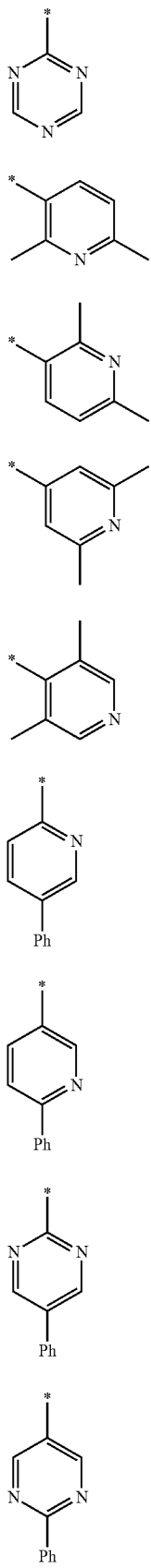
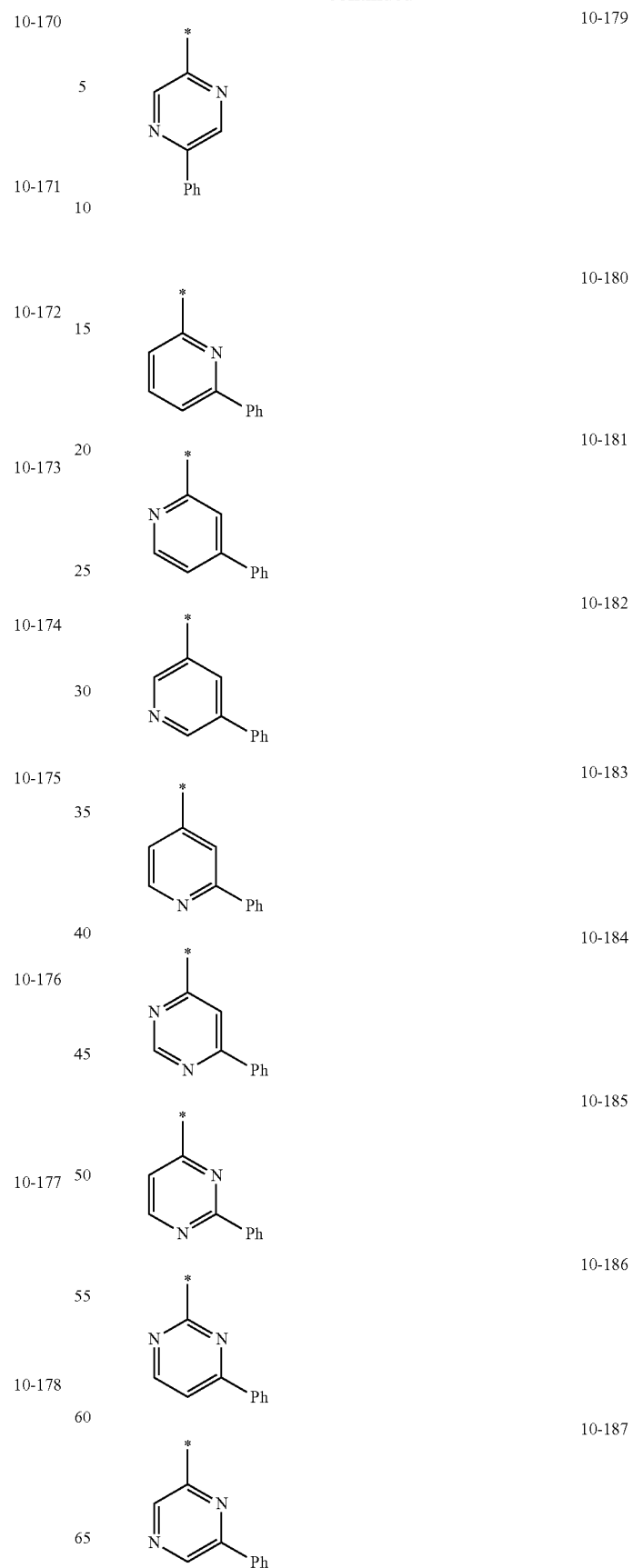

-continued
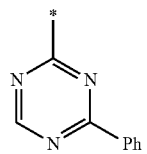 10-188
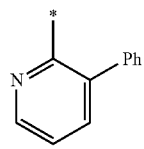 10-189
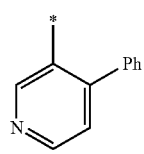 10-190
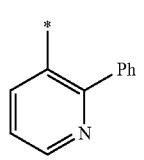 10-191
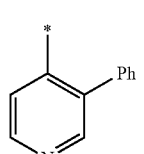 10-192
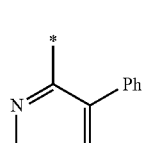 10-193
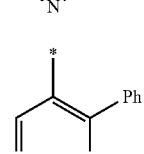 10-194
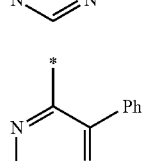 10-195
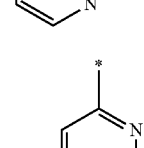 10-196
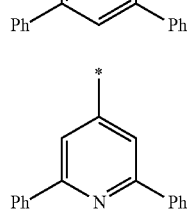 10-197
-continued
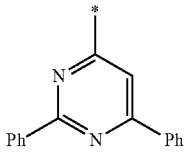 10-198
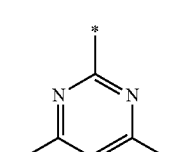 10-199
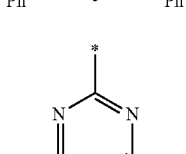 10-200
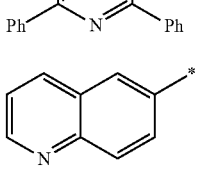 10-201
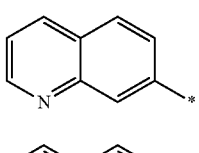 10-202
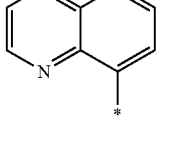 10-203
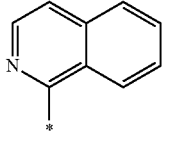 10-204
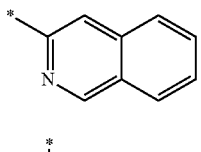 10-205
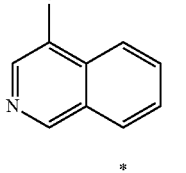 10-206
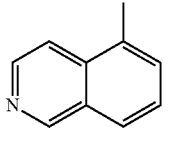 10-207
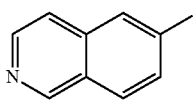 10-208

-continued
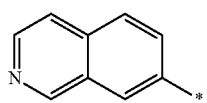 
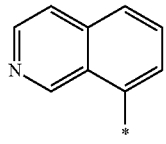 
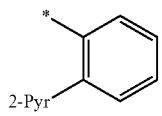 2-Pyr
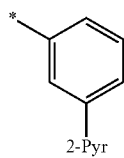 2-Pyr
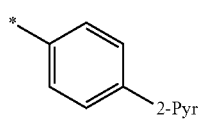 2-Pyr
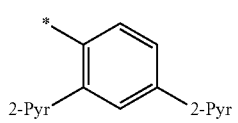 2-Pyr, 2-Pyr
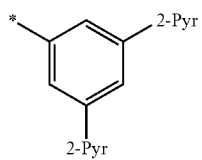 2-Pyr, 2-Pyr
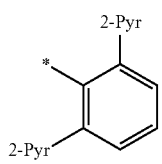 2-Pyr, 2-Pyr
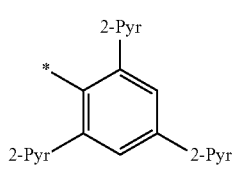 2-Pyr, 2-Pyr, 2-Pyr
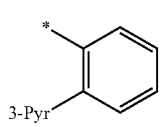 3-Pyr
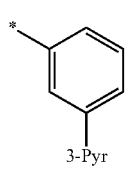 3-Pyr
-continued
10-209 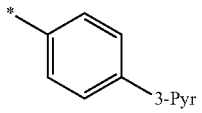 3-Pyr
10-210 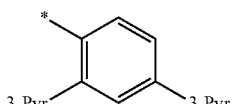 3-Pyr, 3-Pyr
10-211 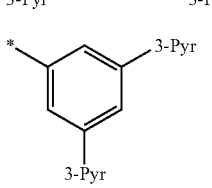 3-Pyr, 3-Pyr
10-212 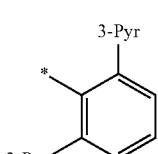 3-Pyr, 3-Pyr
10-213 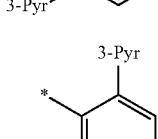 3-Pyr, 3-Pyr
10-214 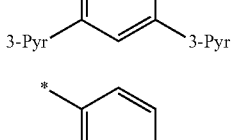 3-Pyr, 3-Pyr, 3-Pyr
10-215 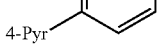 4-Pyr
10-216 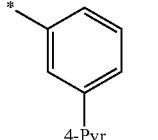 4-Pyr
10-217 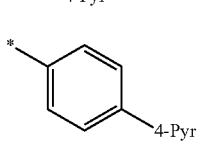 4-Pyr
10-218 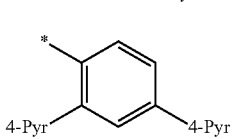 4-Pyr, 4-Pyr
10-219 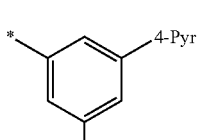 4-Pyr, 4-Pyr
10-220
10-221
10-222
10-223
10-224
10-225
10-226
10-227
10-228
10-229
10-230 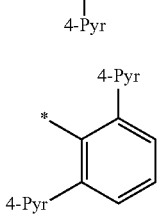 4-Pyr, 4-Pyr

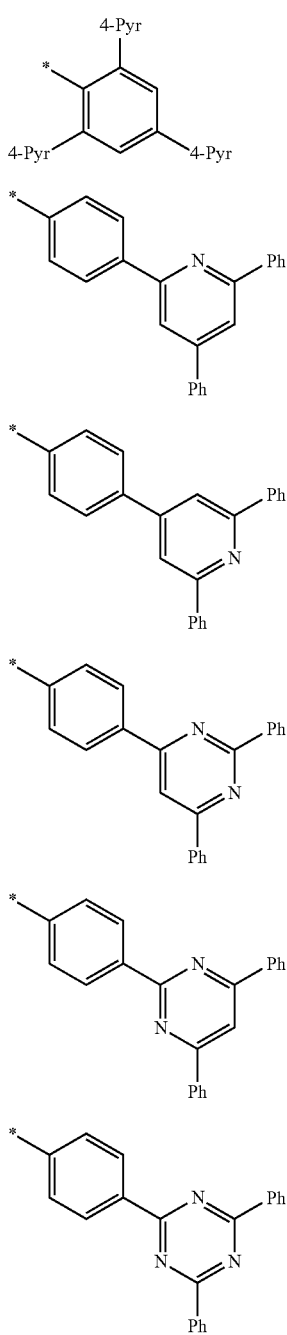

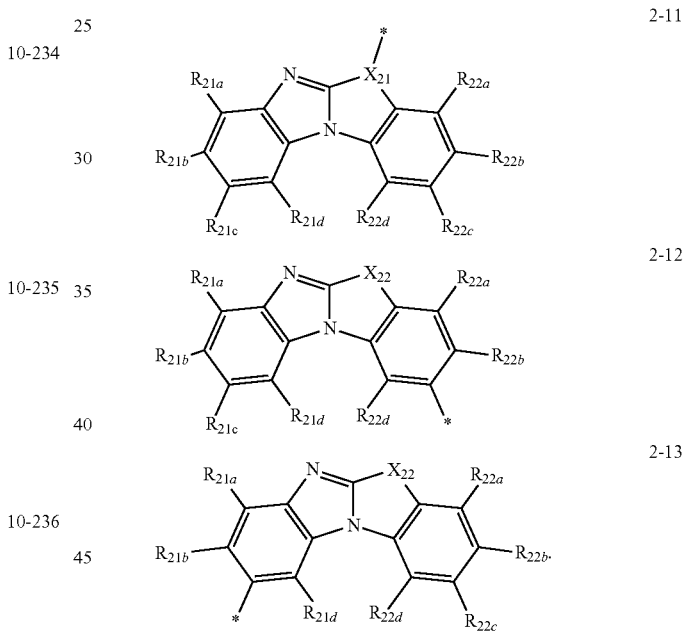

In Formulae 9-1 to 9-27 and 10-1 to 10-236,
* indicates a binding site to a neighboring atom,
i-Pr indicates an isopropyl group, t-Bu indicates a tert-butyl group,
Ph indicates a phenyl group,
1-Nph indicates a 1-naphthyl group, 2-Nph indicates a 2-naphthyl group,
2-Pyr indicates a 2-pyridyl group, 3-Pyr indicates a 3-pyridyl group, 4-Pyr indicates a 4-pyridyl group, and
$Q_1$ to $Q_3$ may each independently be:
a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a phenyl($C_1$-$C_{20}$ alkyl) group, or a naphthyl group; or a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group, each substituted with deuterium, a phenyl group, or a combination thereof.

In Formulae 2-1 to 2-3, b21 indicates the number of substitutions of $R_{21}$, and b22 indicates the number of substitutions of $R_{22}$, wherein b21 and b22 may each independently be 1, 2, 3, 4, 5, 6, 7, 8, 9, or 10. When b21 is 2 or more, a plurality of $R_{21}$(s) may be identical to or different from each other, and when b22 is 2 or more, a plurality of $R_{22}$(s) may be identical to or different from each other.

In one embodiment, $A_{11}$ may be a group represented by any of Formulae 2-11 to 2-13, but embodiments of the present disclosure are not limited thereto:

In Formulae 2-11 to 2-13,
$X_{21}$ and $X_{22}$ may each independently be the same as defined in connection with Formulae 2-1 to 2-3,
$R_{21a}$ to $R_{21d}$ may each independently be the same as defined in connection with $R_{21}$ in Formula 2-1,
$R_{22a}$ to $R_{22d}$ may each independently be the same as defined in connection with $R_{22}$, and
* indicates a binding site to a neighboring atom.

In Formula 1, k11 indicates the number of substitutions of $A_{11}$, and may be an integer from 1 to 5. When k11 is 2 or more, a plurality of $A_{11}$(s) may be identical to or different from each other.

For example, k11 in Formula 1 may be 1, 2, or 3, but embodiments of the present disclosure are not limited thereto.

In one embodiment, k11 in Formula 1 may be 2, but embodiments of the present disclosure are not limited thereto.

In Formula 1, $A_{12}$ may be a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_7$-$C_{60}$ alkylaryl group, a substituted or unsubstituted $C_1$-$C_{60}$ heteroaryl group, a substituted or unsubstituted $C_2$-$C_{60}$ alkylheteroaryl group, a substituted or unsubstituted monovalent non-aromatic condensed polycyclic group, or a substituted or unsubstituted monovalent non-aromatic condensed heteropolycyclic group.

For example, $A_{12}$ in Formula 1 may be:

a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group; or a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each substituted with deuterium, —F, —Cl, —Br, —I, —$CD_3$, —$CD_2H$, —$CDH_2$, —$CF_3$, —$CF_2H$, —$CFH_2$, a hydroxyl group, a nitro group, a cyano group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a phenyl ($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyridinyl group substituted with a phenyl group, a pyrazinyl group, a pyrazinyl group substituted with a phenyl group a pyrimidinyl group, a pyrimidinyl group substituted with a phenyl group, a pyridazinyl group, a pyridazinyl group substituted with a phenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a triazinyl group substituted with a phenyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si($Q_{11}$)($Q_{12}$)($Q_{13}$), —B($Q_{11}$)($Q_{12}$), —N($Q_{11}$)($Q_{12}$), or a combination thereof, or $Q_{11}$ to $Q_{13}$ may each independently be:

a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a phenyl($C_1$-$C_{20}$ alkyl) group, or a naphthyl group; or a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group substituted with deuterium, a phenyl group, or a combination thereof, but embodiments of the present disclosure are not limited thereto.

In one embodiment, $A_{12}$ in Formula 1 may be a group represented by Formulae 10-1 to 10-236, but embodiments of the present disclosure are not limited thereto.

In one embodiment, $A_{12}$ in Formula 1 may be a group represented by Formulae 10-1 to 10-138, but embodiments of the present disclosure are not limited thereto.

In Formula 1, k12 indicates the number of $A_{12}$(s), and may be an integer from 0 to 5. When k12 is 2 or more, a plurality of $A_{12}$(s) may be identical to or different from each other.

For example, k12 in Formula 1 may be 0, 1, 2, or 3, but embodiments of the present disclosure are not limited thereto.

In one embodiment, k12 in Formula 1 may be 1 or 2, but embodiments of the present disclosure are not limited thereto.

The sum of k11 and k12 in Formula 1 may be 4 or 5.

For example, the sum of k11 and k12 in Formula 1 may be 4, but embodiments of the present disclosure are not limited thereto.

In Formula 1, $R_{11}$ may be hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$ ($Q_1$), —P(=O)($Q_1$)($Q_2$), or —P(=S)($Q_1$)($Q_2$), and $Q_1$ to $Q_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with deuterium, —F, a cyano group, a $C_1$-$C_{60}$ alkyl group, a $C_6$-$C_{60}$ aryl group, or a combination thereof, or a $C_6$-$C_{60}$ aryl group substituted with deuterium, —F, a cyano group, a $C_1$-$C_{60}$ alkyl group, a $C_6$-$C_{60}$ aryl group, or a combination thereof.

For example, $R_{11}$ in Formula 1 may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a pyridinyl group, a pyrimidinyl group, or a combination thereof;

a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each substituted with deuterium, —F, —Cl, —Br, —I, —CD$_3$, —CD$_2$H, —CDH$_2$, —CF$_3$, —CF$_2$H, —CFH$_2$, a hydroxyl group, a nitro group, a cyano group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyridinyl group substituted with a phenyl group, a pyrazinyl group, a pyrazinyl group substituted with a phenyl group a pyrimidinyl group, a pyrimidinyl group substituted with a phenyl group, a pyridazinyl group, a pyridazinyl group substituted with a phenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a triazinyl group substituted with a phenyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si($Q_{11}$)($Q_{12}$)($Q_{13}$), —B($Q_{11}$)($Q_{12}$), —N($Q_{11}$)($Q_{12}$), or a combination thereof; or —Si($Q_1$)($Q_2$)($Q_3$), —B($Q_1$)($Q_2$), or —N($Q_1$)($Q_2$), and $Q_1$ to $Q_3$ and $Q_{11}$ to $Q_{13}$ may each independently be:

a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a phenyl($C_1$-$C_{20}$ alkyl) group, or a naphthyl group; or a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group substituted with deuterium, a phenyl group, or a combination thereof, but embodiments of the present disclosure are not limited thereto.

In one embodiment, $R_{11}$ in Formula 1 may be hydrogen, deuterium, —F, a cyano group, a nitro group, —$CH_3$, —$CD_3$, —$CD_2H$, —$CDH_2$, —$CF_3$, —$CF_2H$, —$CFH_2$, groups represented by Formulae 9-1 to 9-27, groups represented by Formulae 9-1 to 9-27 in which a hydrogen is substituted with deuterium, groups represented by Formulae 10-1 to 10-226, —Si($Q_1$)($Q_2$)($Q_3$), —B($Q_1$)($Q_2$), or —N($Q_1$)($Q_2$), but embodiments of the present disclosure are not limited thereto:

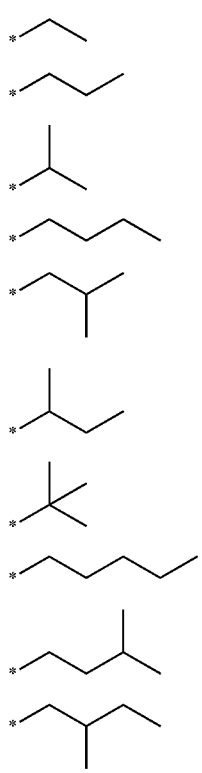

9-1

9-2

9-3

9-4

9-5

9-6

9-7

9-8

9-9

9-10

-continued

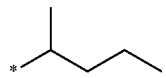

9-11

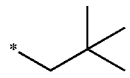

9-12

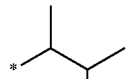

9-13

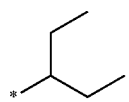

9-14

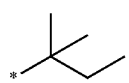

9-15

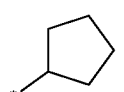

9-16

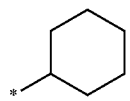

9-17

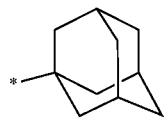

9-18

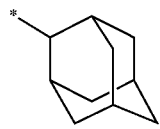

9-19

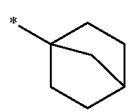

9-20

9-21

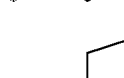

9-22

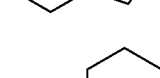

9-23

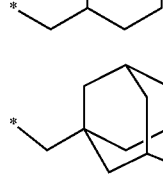

9-24

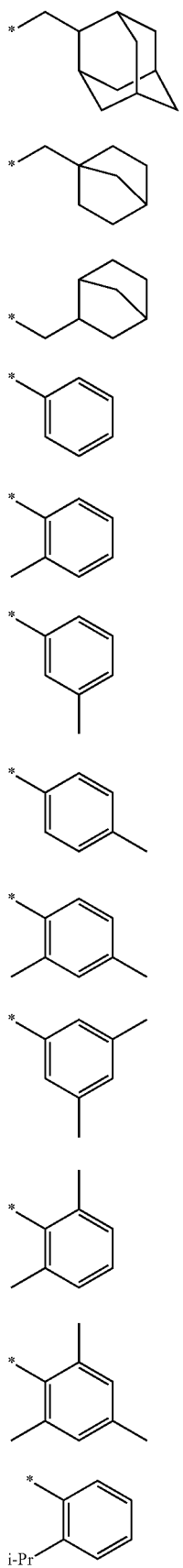
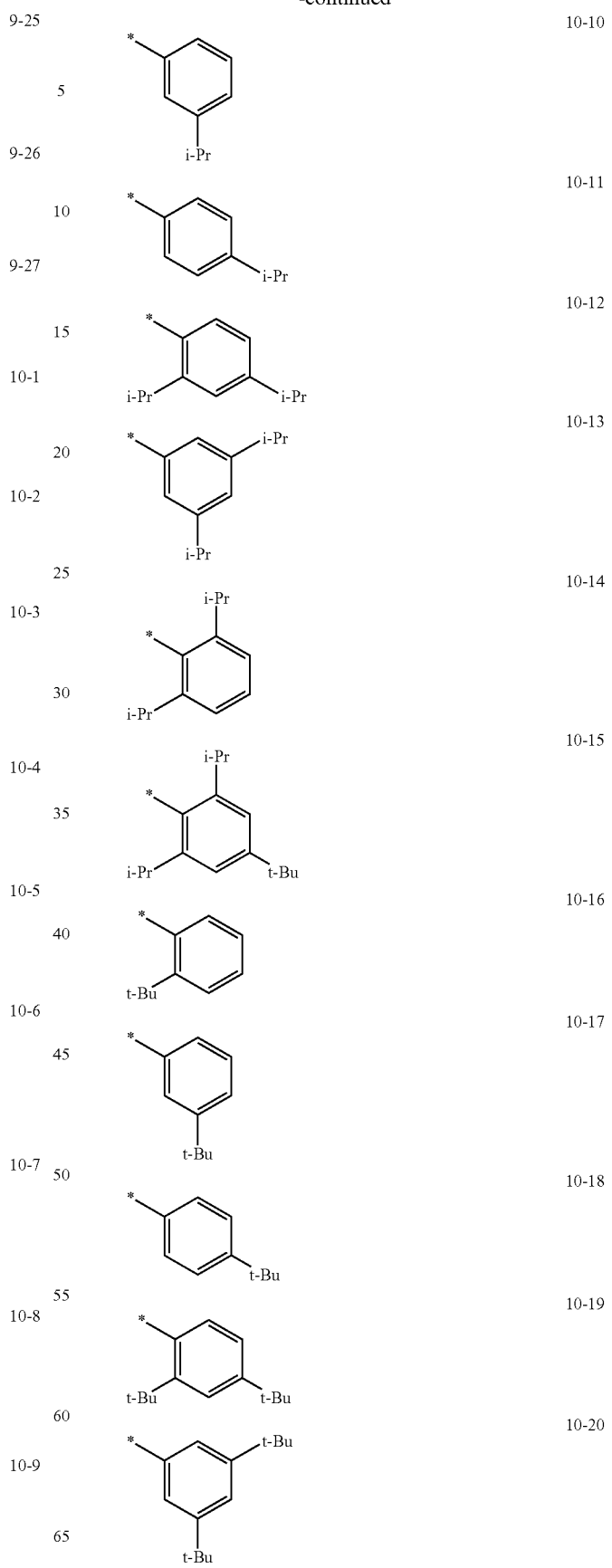

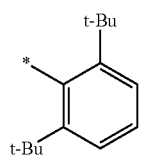
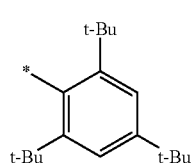
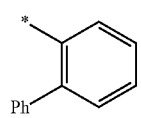
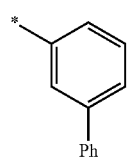
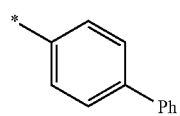
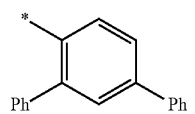
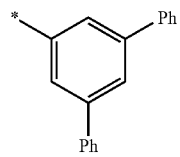
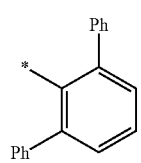
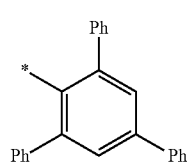
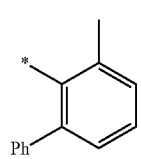
10-21
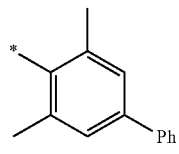
10-22
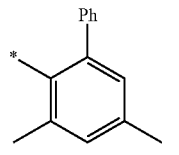
10-23
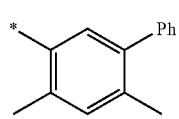
10-24
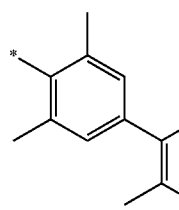
10-25
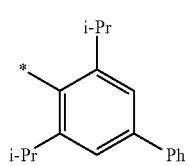
10-26
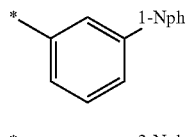
10-27
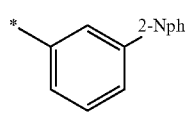
10-28
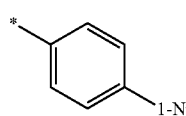
10-29
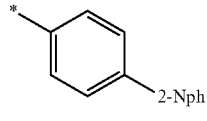
10-30
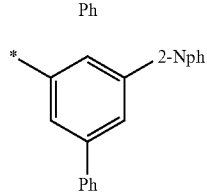

-continued
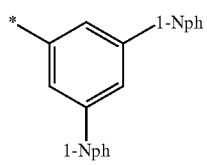
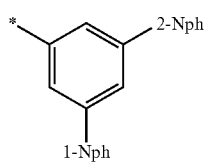
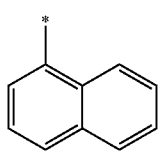
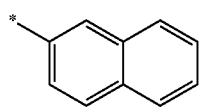
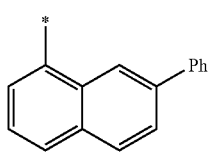
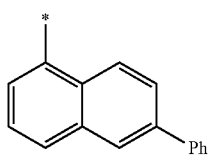
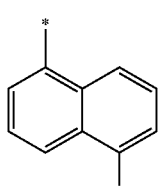
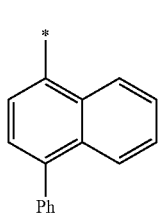
-continued
10-42
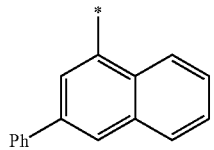
10-43
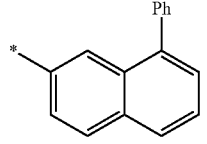
10-44
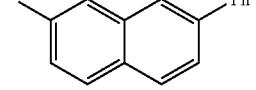
10-45
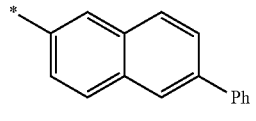
10-46
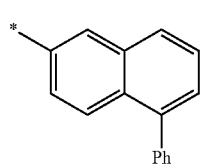
10-47
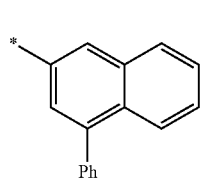
10-48
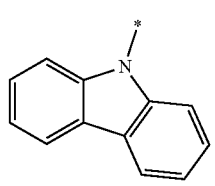
10-49
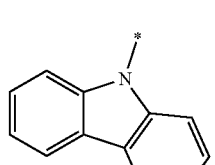
10-50
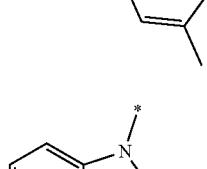
10-51
10-52
10-53
10-54
10-55
10-56
10-57
10-58
10-59
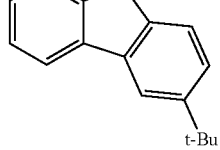

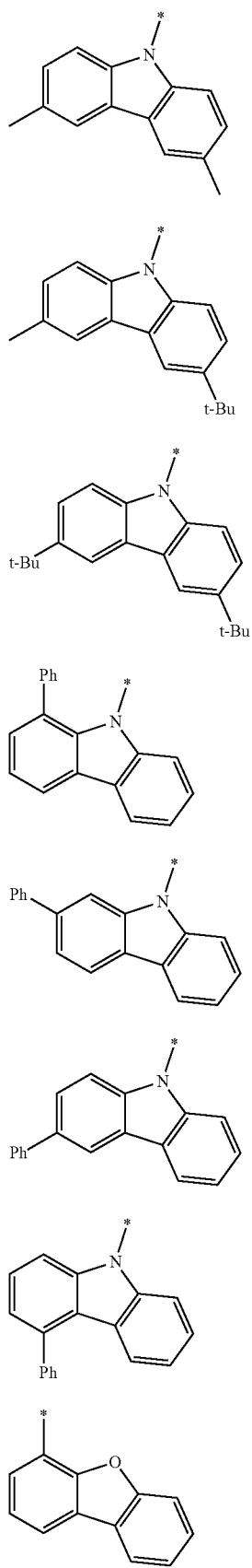
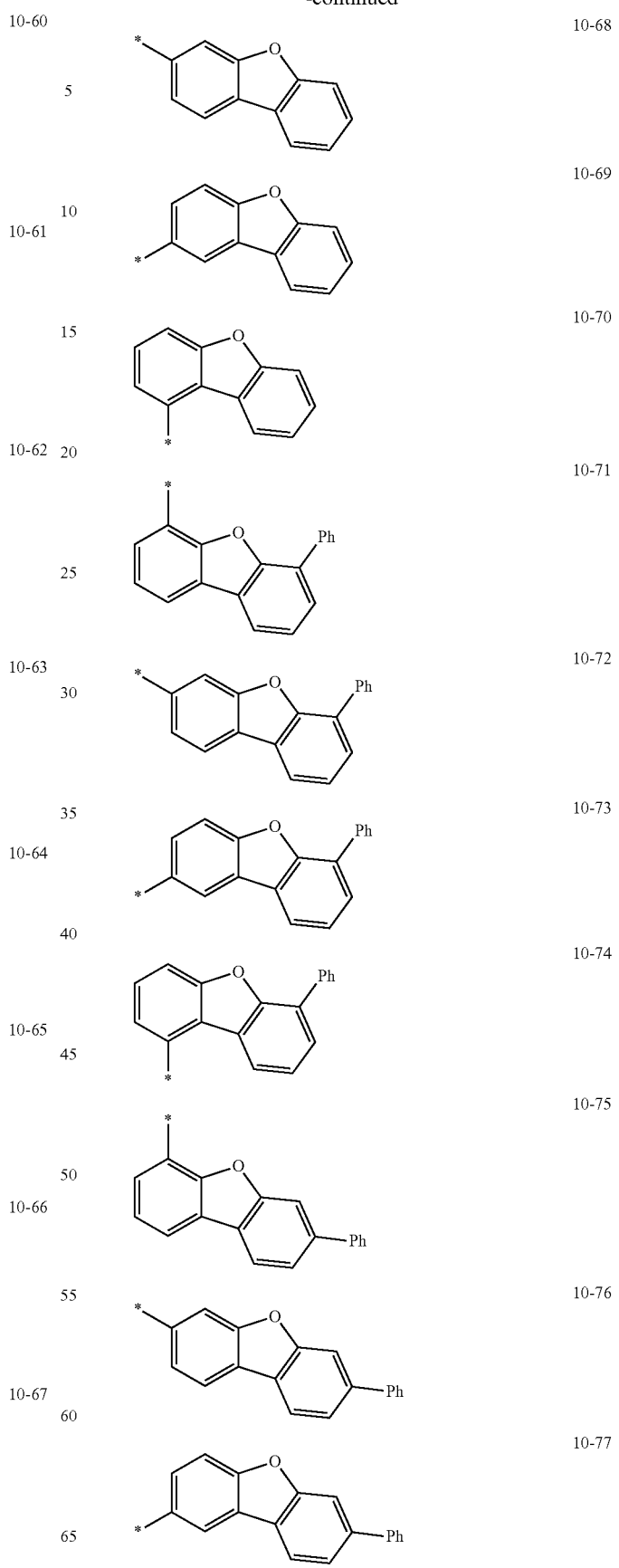

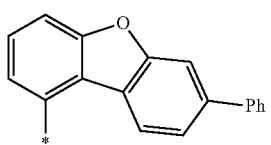
10-78
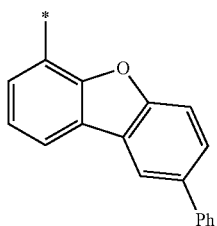
10-79
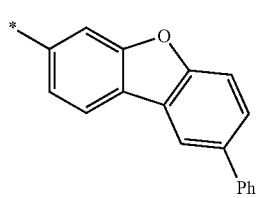
10-80
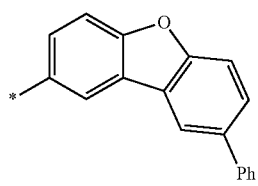
10-81
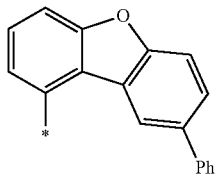
10-82
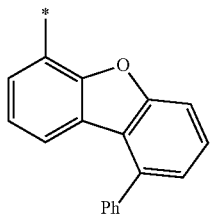
10-83
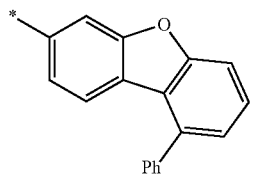
10-84
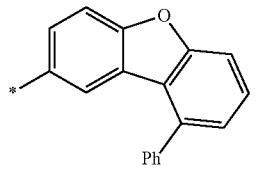
10-85
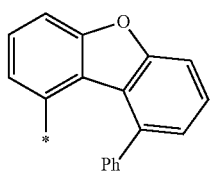
10-86
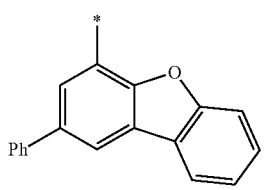
10-87
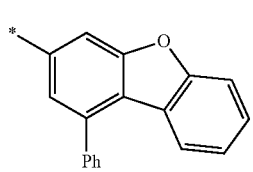
10-88
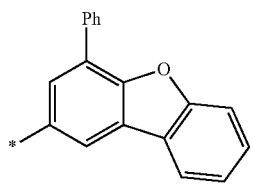
10-89
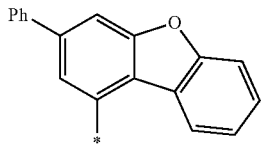
10-90
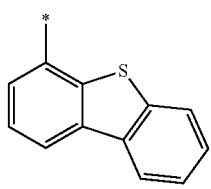
10-91
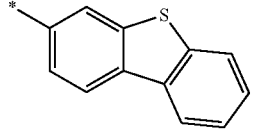
10-92
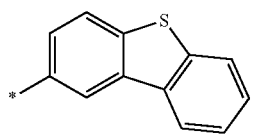
10-93
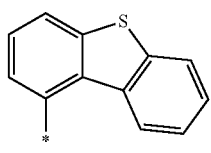
10-94

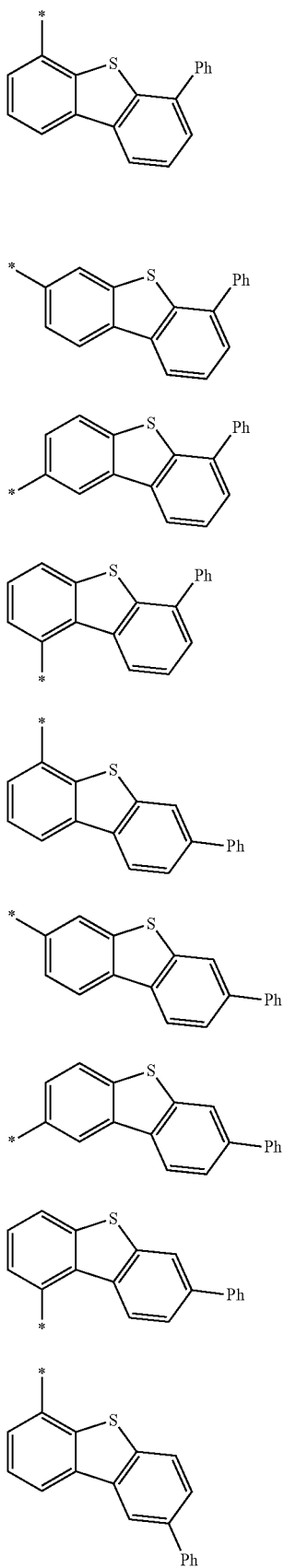
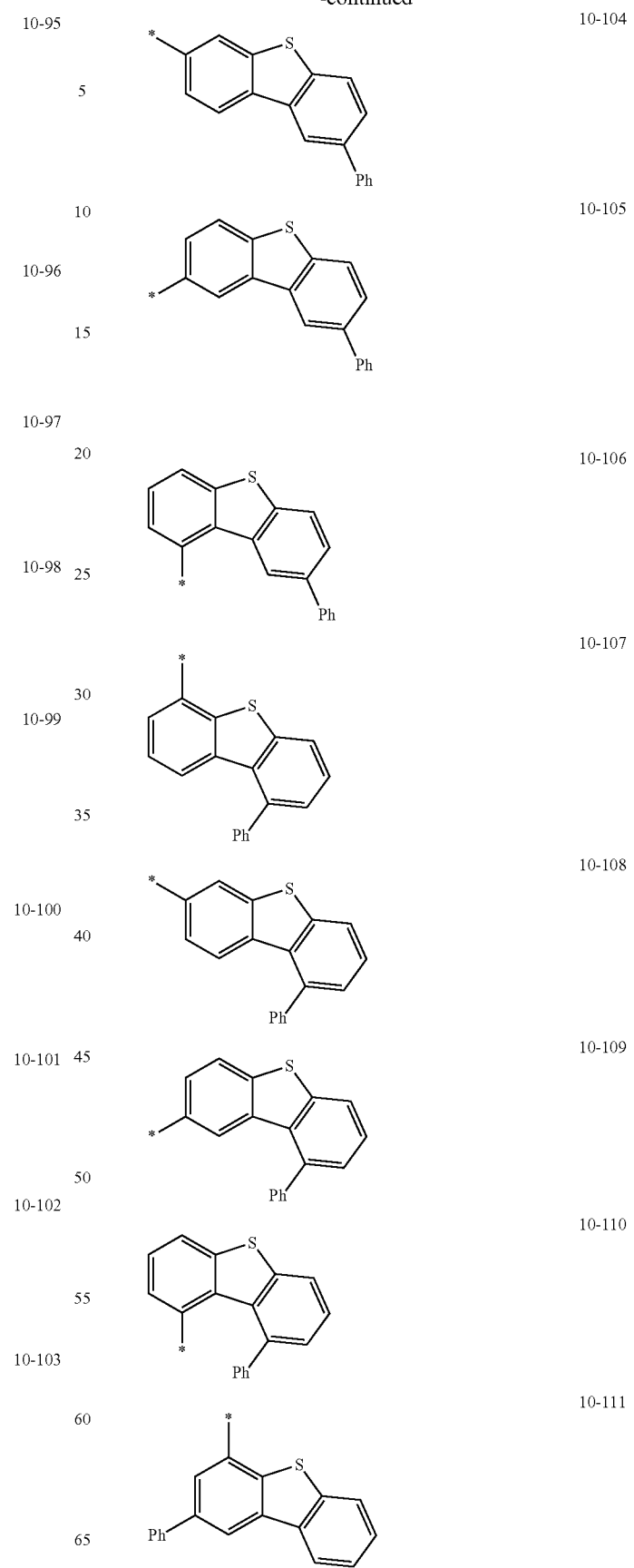

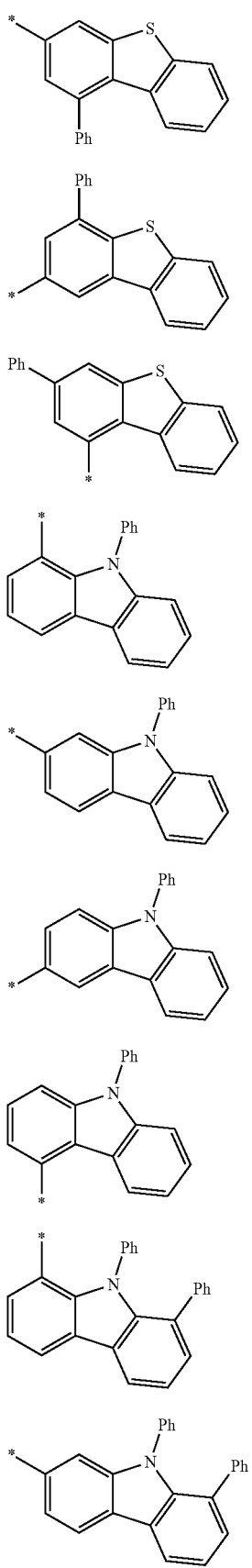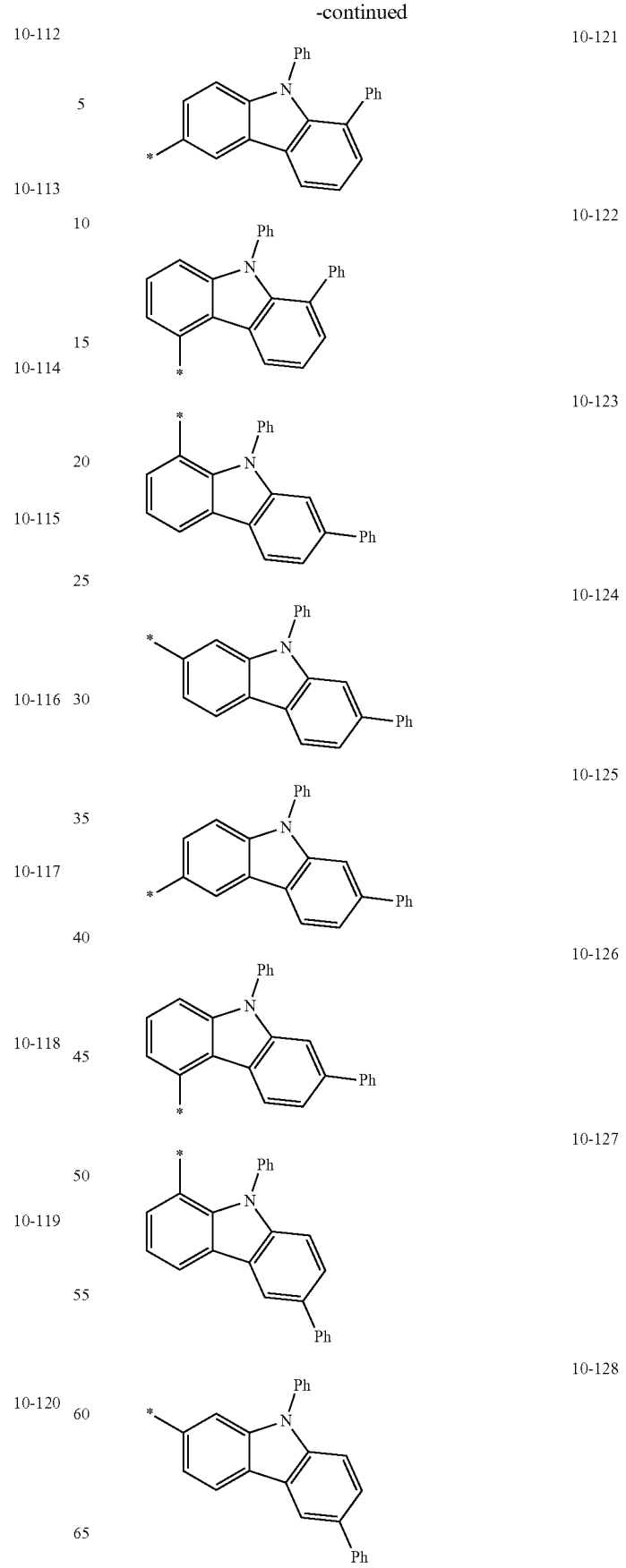

-continued
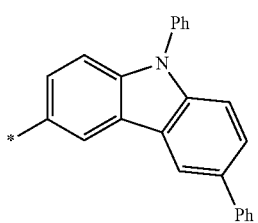
10-129
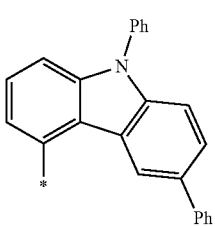
10-130
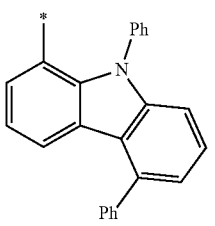
10-131
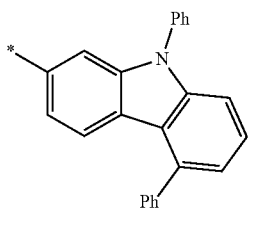
10-132
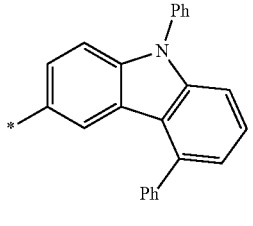
10-133
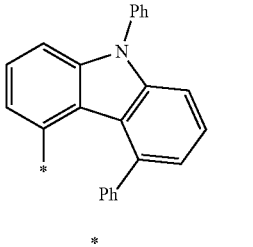
10-134
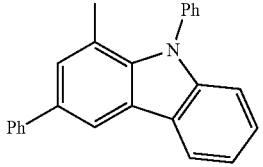
10-135
-continued
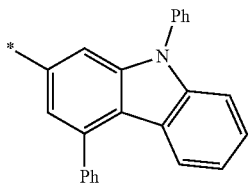
10-136
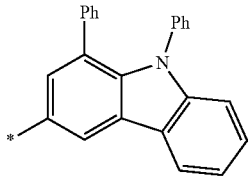
10-137
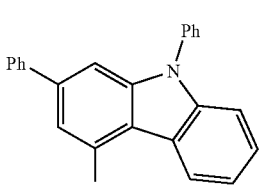
10-138
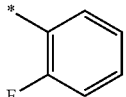
10-139
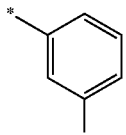
10-140
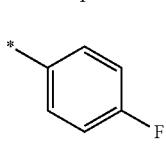
10-141
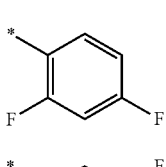
10-142
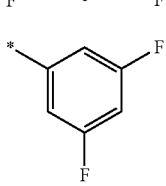
10-143
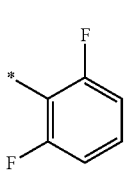
10-144
10-145

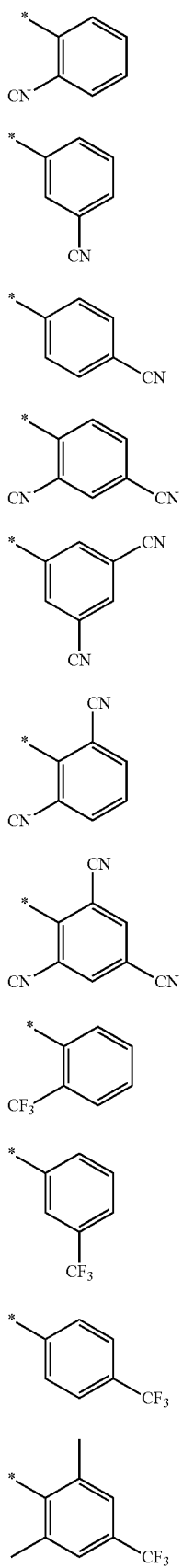
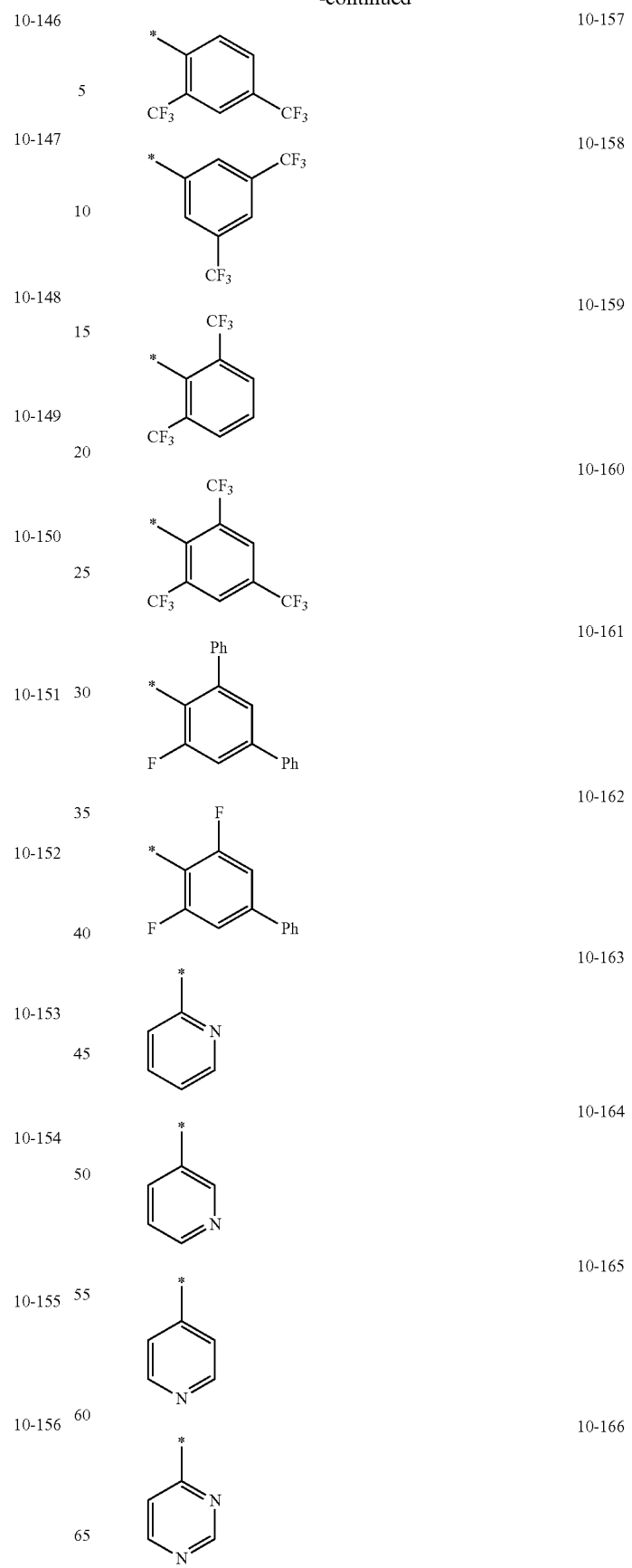

-continued
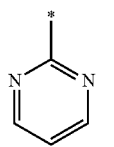
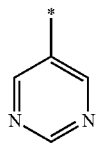
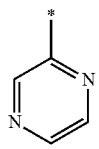
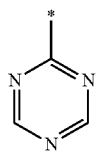
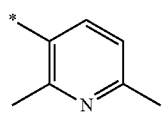
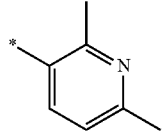
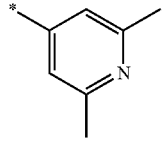
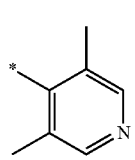
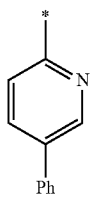
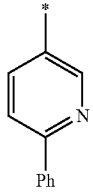
-continued
10-167
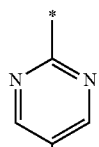
10-168
10-169
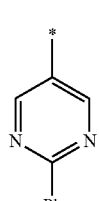
10-170
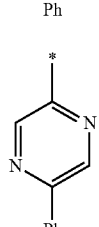
10-171
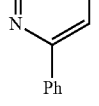
10-172
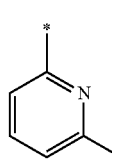
10-173
10-174
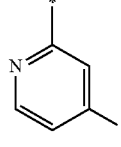
10-175
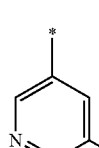
10-176
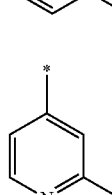
10-177
10-178
10-179
10-180
10-181
10-182
10-183
10-184
10-185
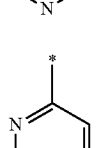
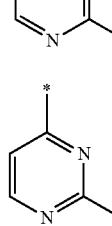

| | |
|---|---|
| 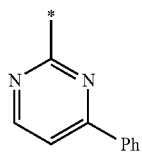 | 10-186 |
| 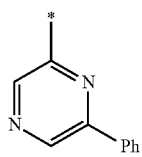 | 10-187 |
| 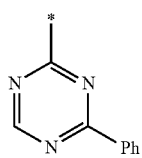 | 10-188 |
| 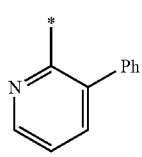 | 10-189 |
| 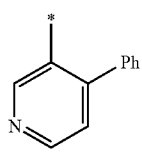 | 10-190 |
| 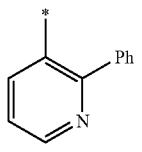 | 10-191 |
| 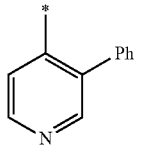 | 10-192 |
| 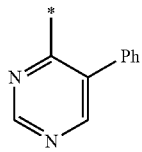 | 10-193 |
| 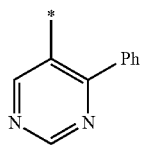 | 10-194 |
| 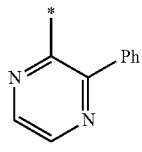 | 10-195 |
| | |
|---|---|
| 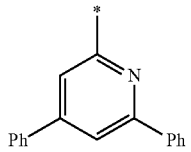 | 10-196 |
| 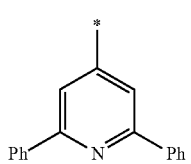 | 10-197 |
| 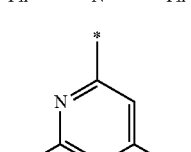 | 10-198 |
| 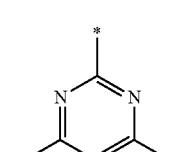 | 10-199 |
| 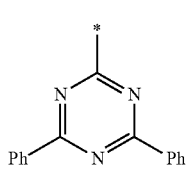 | 10-200 |
| 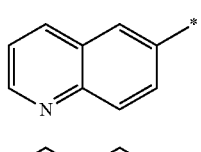 | 10-201 |
| 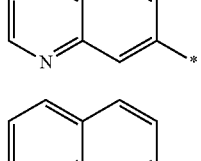 | 10-202 |
| 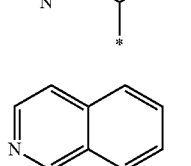 | 10-203 |
| 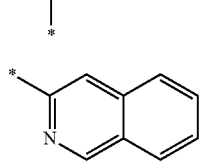 | 10-204 |
| 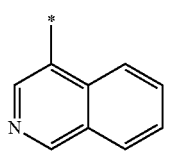 | 10-205 |

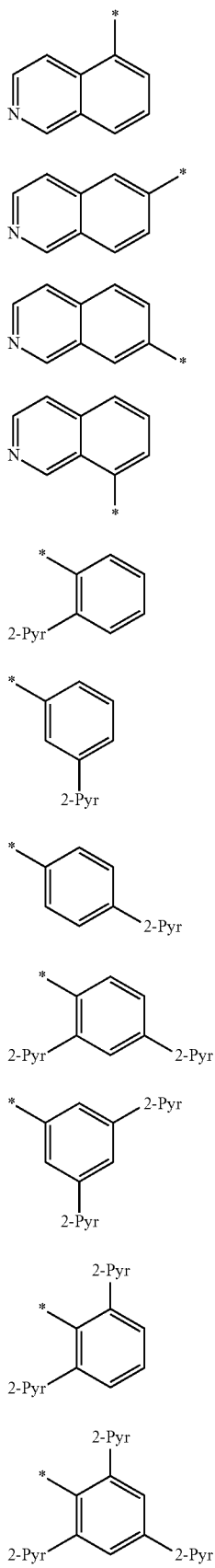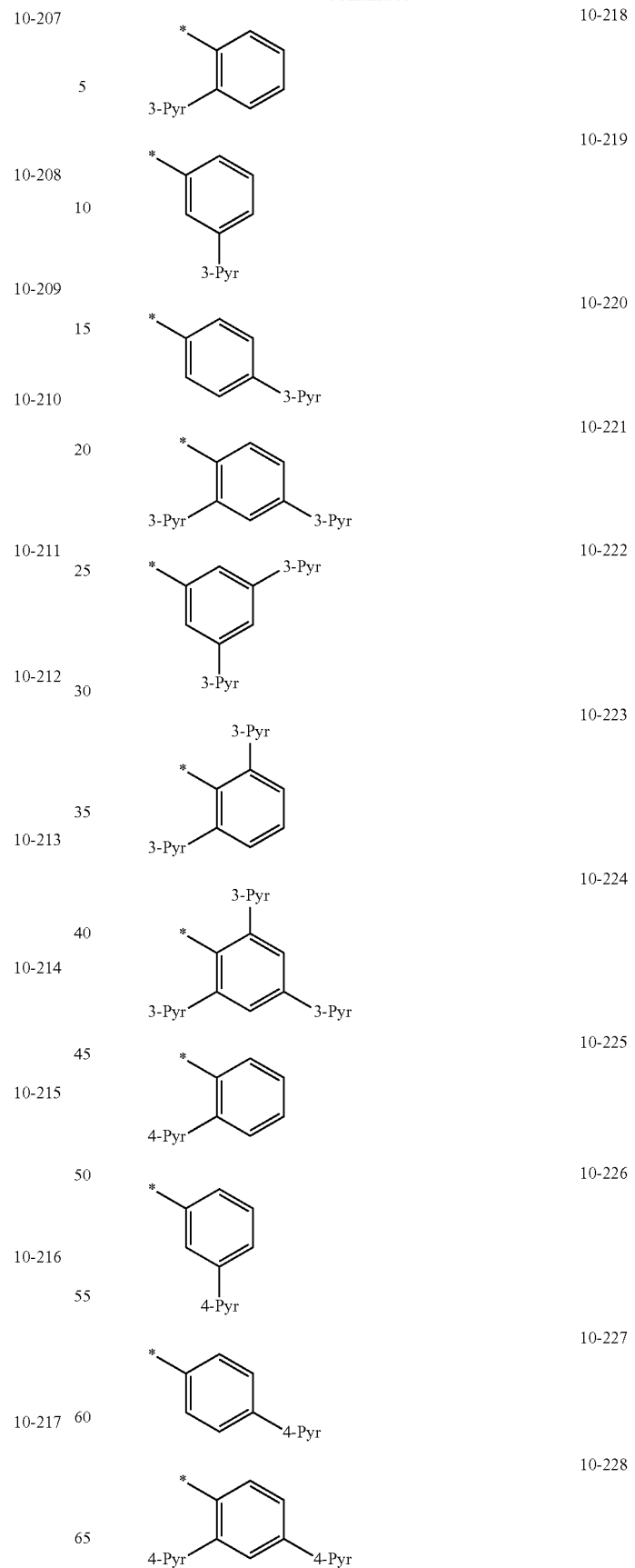

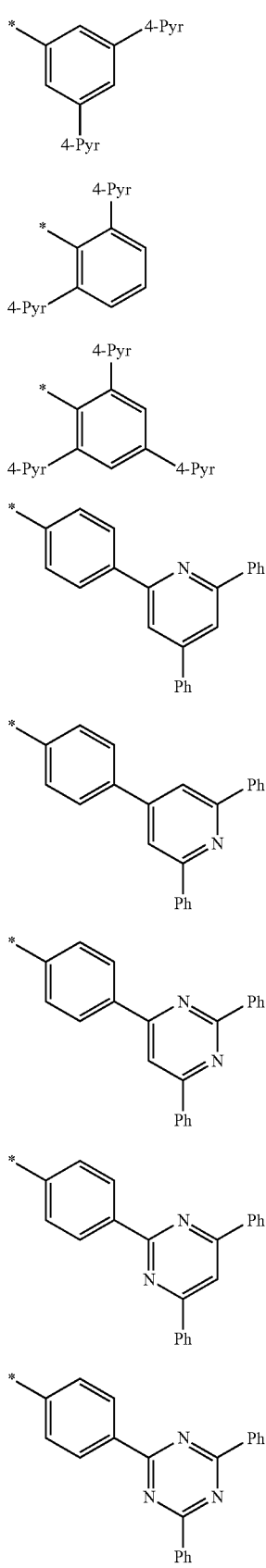

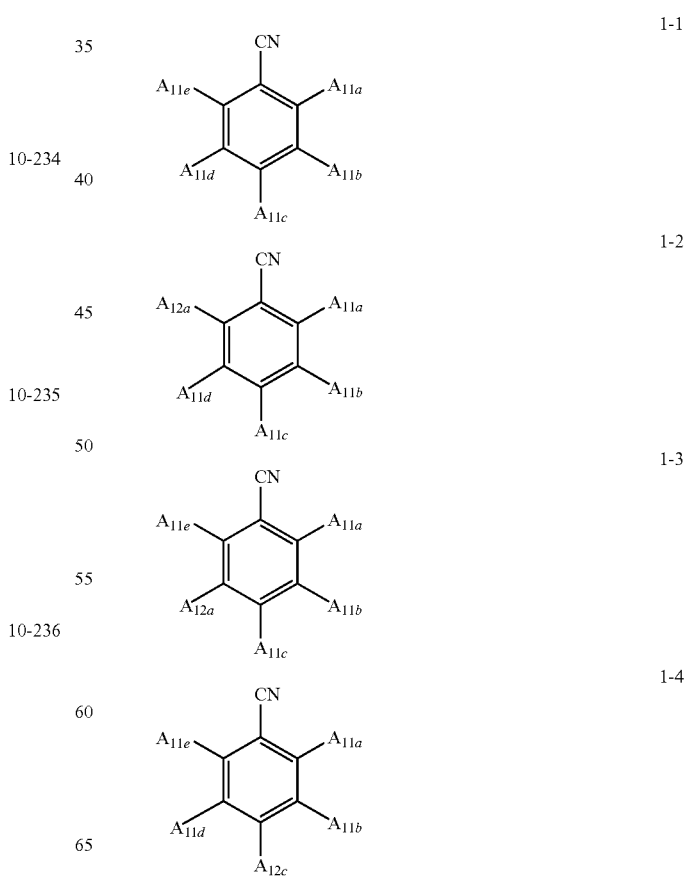

In Formulae 9-1 to 9-27 and 10-1 to 10-236,

* indicates a binding site to a neighboring atom, i-Pr indicates an isopropyl group, t-Bu indicates a tert-butyl group, Ph indicates a phenyl group, 1-Nph indicates a 1-naphthyl group, 2-Nph indicates a 2-naphthyl group, 2-Pyr indicates a 2-pyridyl group, 3-Pyr indicates a 3-pyridyl group, 4-Pyr indicates a 4-pyridyl group, and $Q_1$ to $Q_3$ may each independently be:

a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a phenyl($C_1$-$C_{20}$ alkyl) group, or a naphthyl group; or a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group substituted with deuterium, a phenyl group, or a combination thereof.

In one embodiment, the condensed-cyclic compound represented by Formula 1 may be a group represented by any of Formulae 1-1 to 1-58, but embodiments of the present disclosure are not limited thereto:

1-5
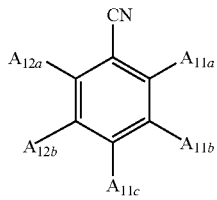
1-6
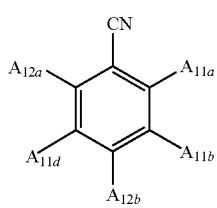
1-7
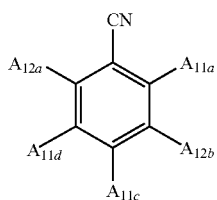
1-8
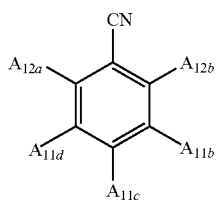
1-9
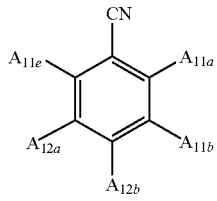
1-10
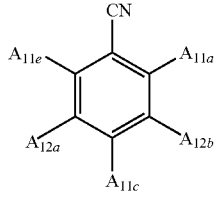
1-11
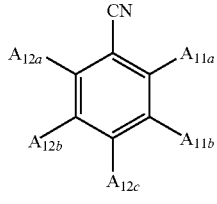
1-12
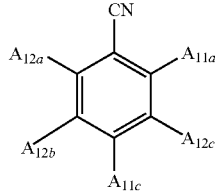
1-13
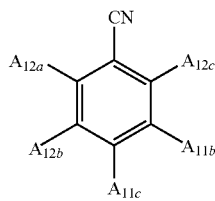
1-14
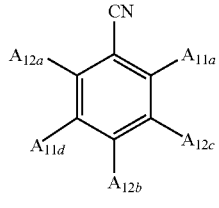
1-15
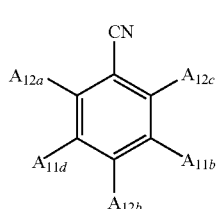
1-16
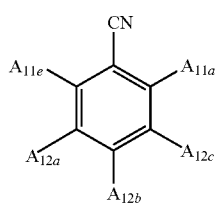
1-17
1-18
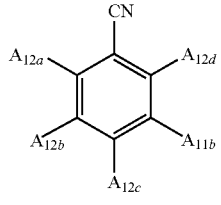

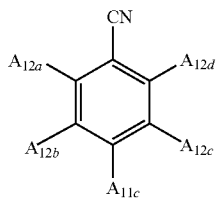
1-19
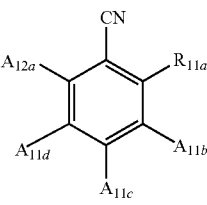
1-26
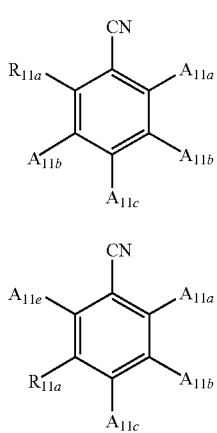
1-20
1-21
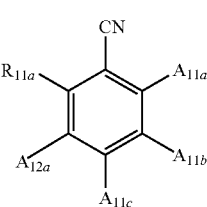
1-27
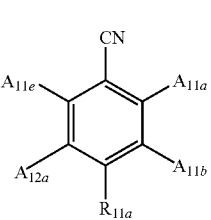
1-28
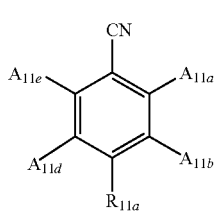
1-22
1-23
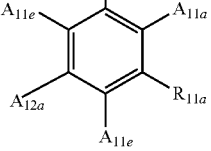
1-29
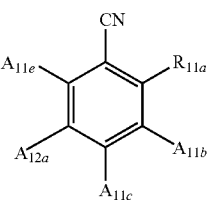
1-30
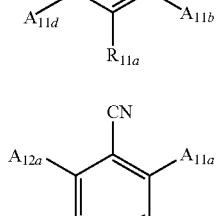
1-24
1-25
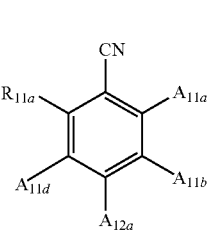
1-31
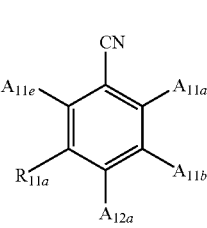
1-32

-continued
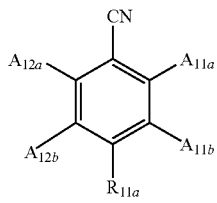
1-33
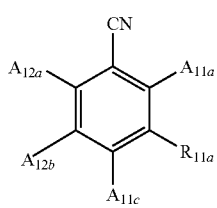
1-34
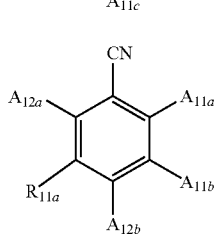
1-35
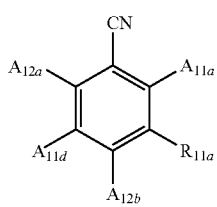
1-36
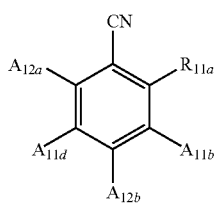
1-37
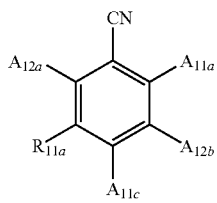
1-38
1-39
-continued
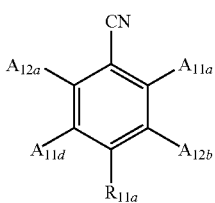
1-40
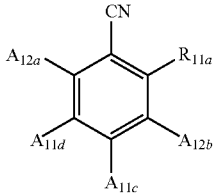
1-41
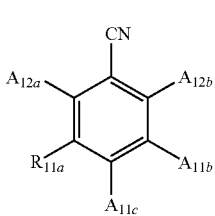
1-42
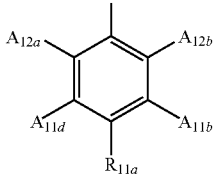
1-43
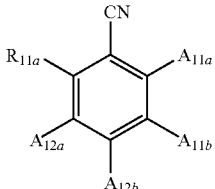
1-44
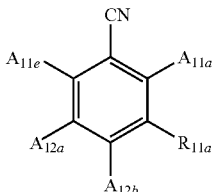
1-45
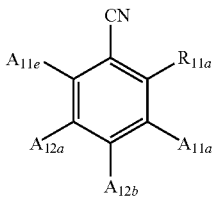
1-46

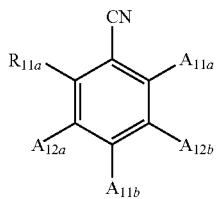

1-47

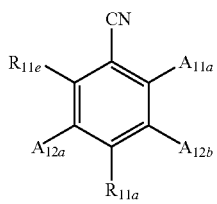

1-48

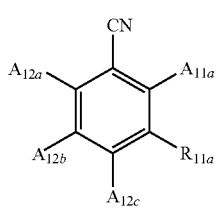

1-49

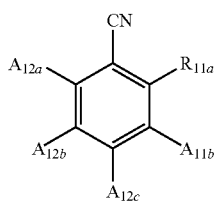

1-50

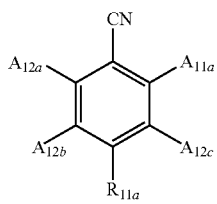

1-51

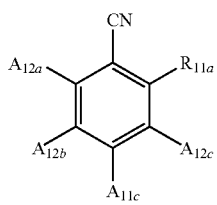

1-52

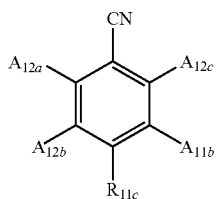

1-53

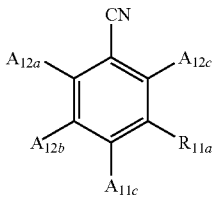

1-54

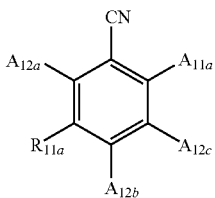

1-55

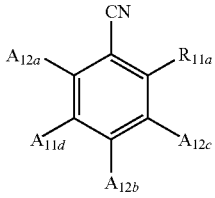

1-56

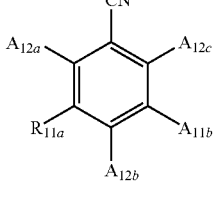

1-57

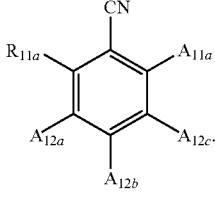

1-58

In Formulae 1-1 to 1-58, $A_{11a}$ to $A_{11d}$ may each independently be the same as defined in connection with $A_{11}$ in Formula 1;

$A_{12a}$ to $A_{12d}$ may each independently be the same as defined in connection with $A_{12}$ in Formula 1;

$R_{11a}$ may be hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$ ($Q_1$), —P(=O)($Q_1$)($Q_2$), or —P(=S)($Q_1$)($Q_2$), and $Q_1$ to $Q_3$ may each independently be hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with deuterium, —F, a cyano group, a $C_1$-$C_{60}$ alkyl group, a $C_6$-$C_{60}$ aryl group, or a combination thereof, or a $C_6$-$C_{60}$ aryl group substituted with deuterium, —F, a cyano group, a $C_1$-$C_{60}$ alkyl group, a $C_6$-$C_{60}$ aryl group, or a combination thereof.

For example, $R_{11a}$ in Formulae 1-1 to 1-58 may be hydrogen, deuterium, —F, —Cl, —Br, —I, or a cyano group, but embodiments of the present disclosure are not limited thereto.

In one embodiment, the condensed-cyclic compound may be represented by any of Formulae 1-1 to 1-19, 1-21 to 1-25, 1-28, 1-29, 1-32 to 1-34, 1-36, 1-37, 1-39, 1-40, 1-42, 1-43, 1-45, 1-48, 1-49, 1-51, 1-53 to 1-55, or 1-57, but embodiments of the present disclosure are not limited thereto.

In one or more embodiments, the condensed-cyclic compound of formula 1 may be of Compounds 1 to 39, but embodiments of the present disclosure are not limited thereto:

1

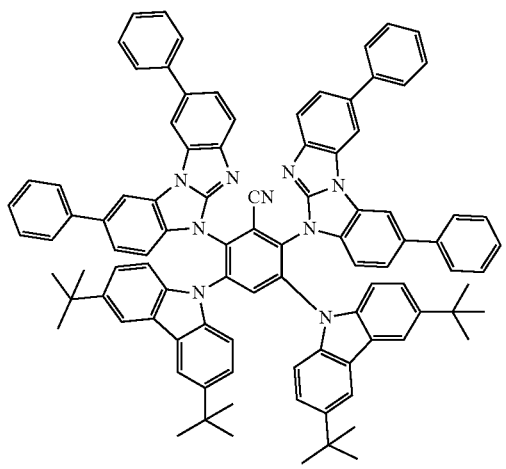

2

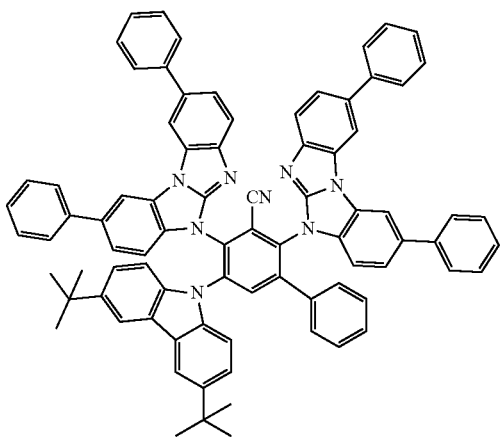

3

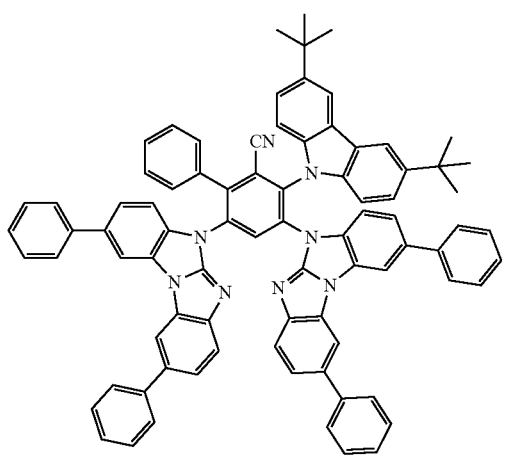

4

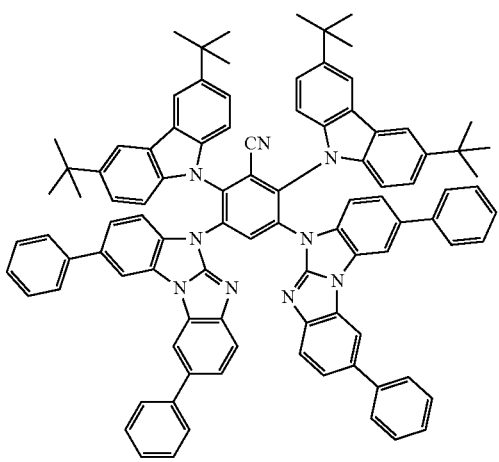

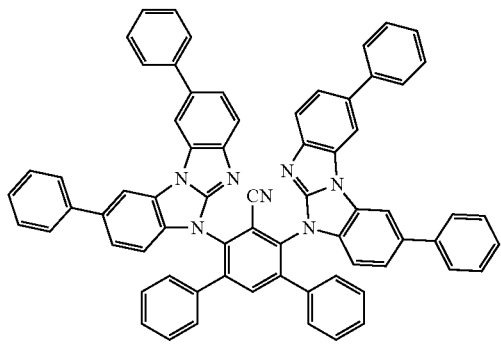
5
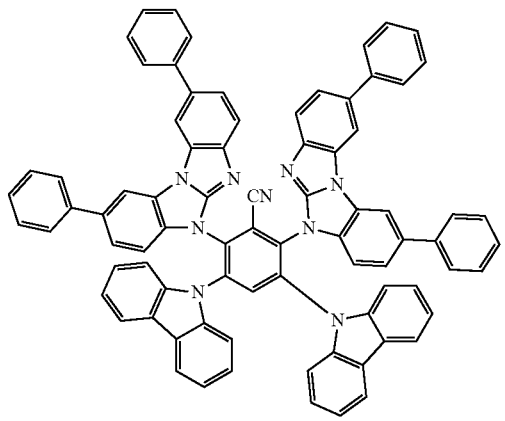
6
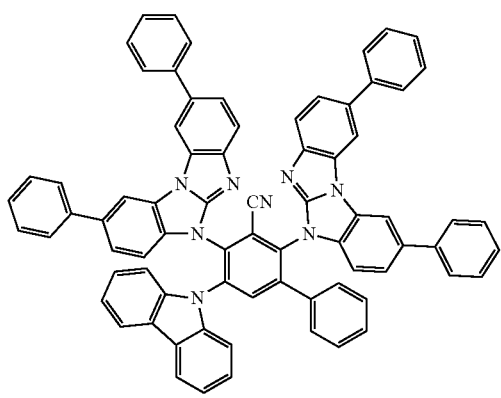
7
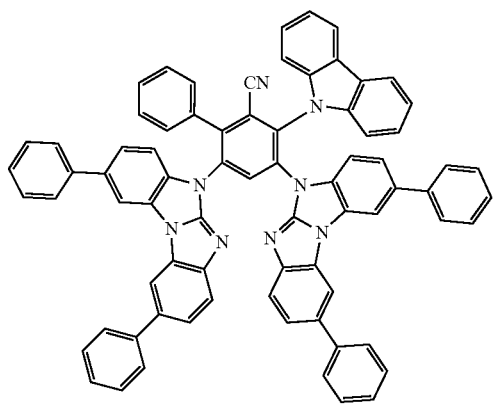
8
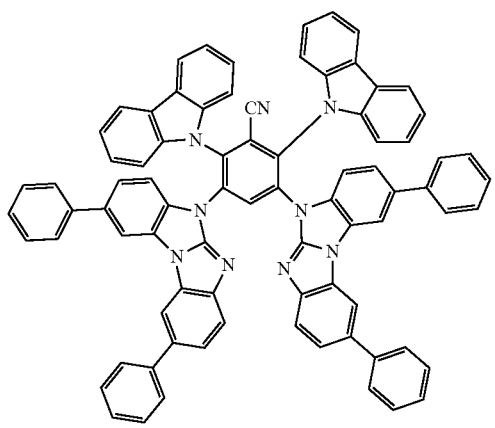
9
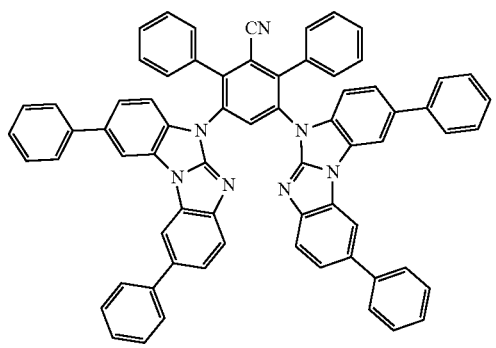
10

-continued
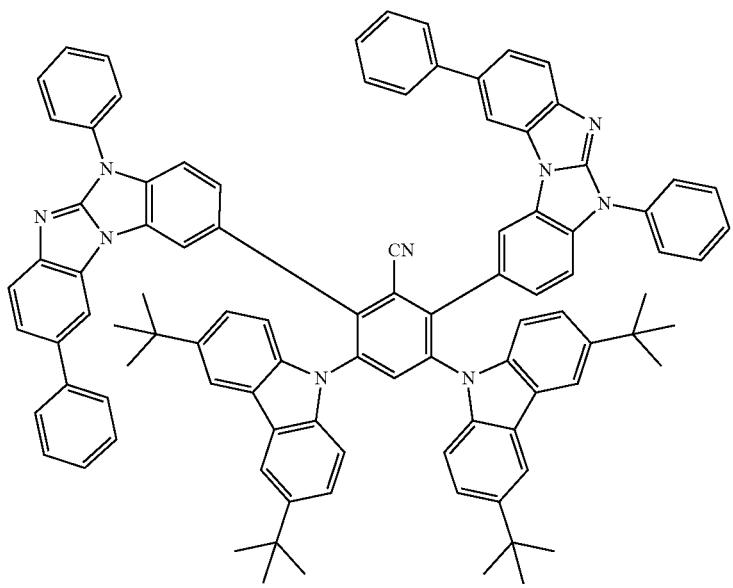
11
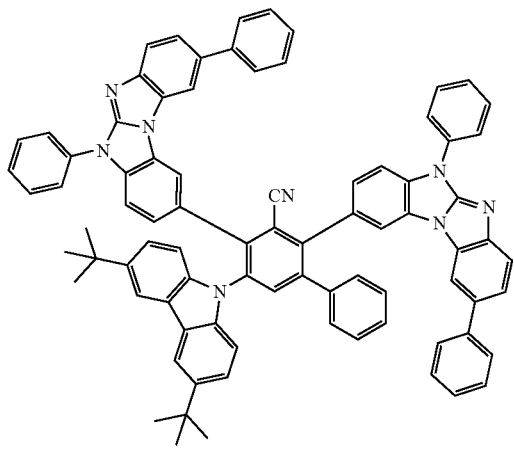
12
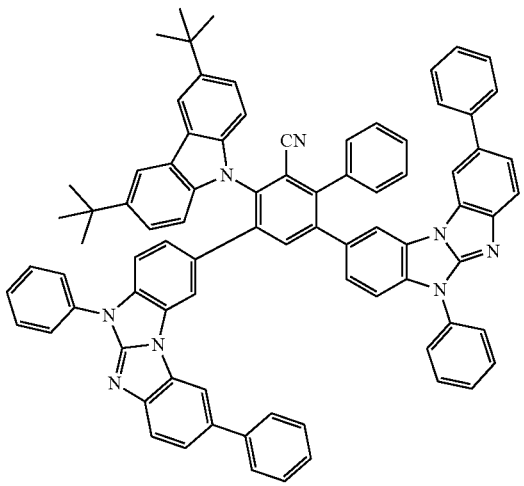
13
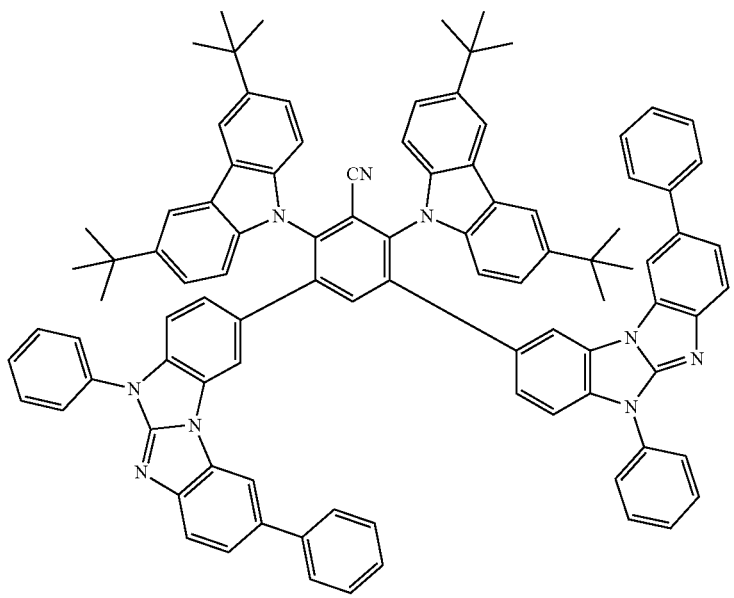
14

-continued
15
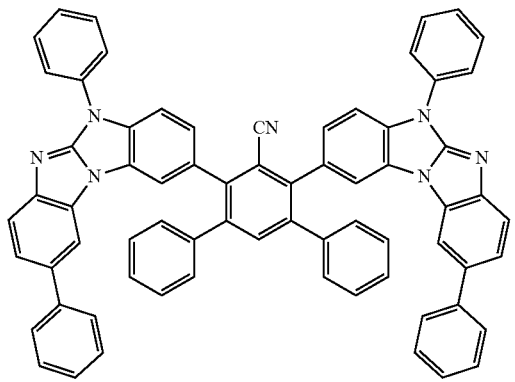
16
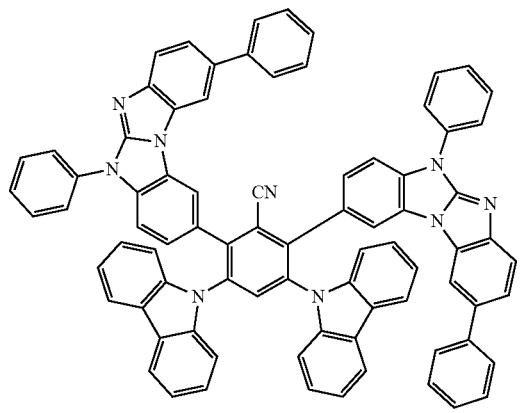
17
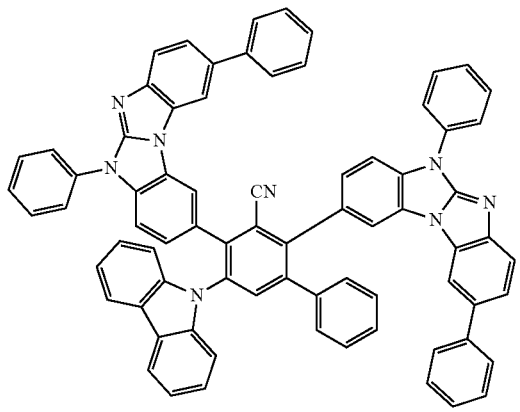
18
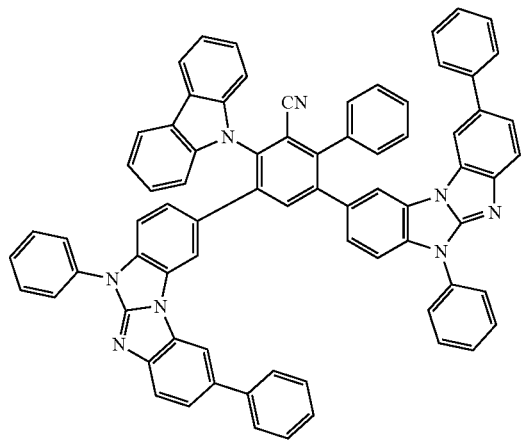
19
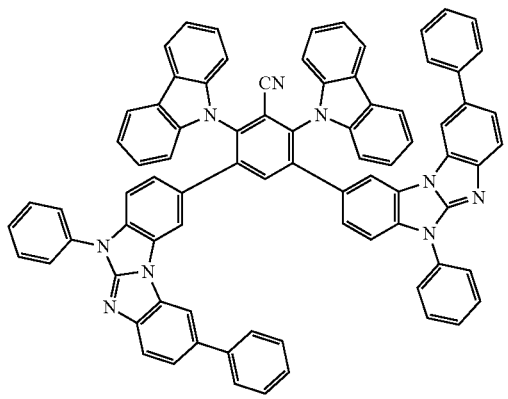
20
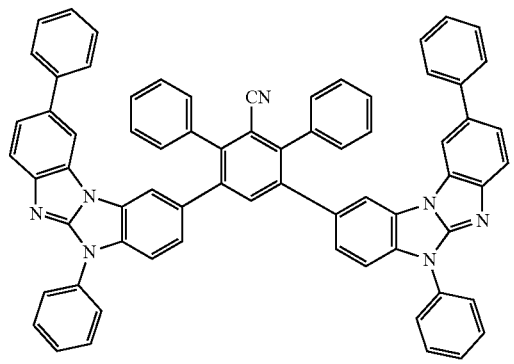

21
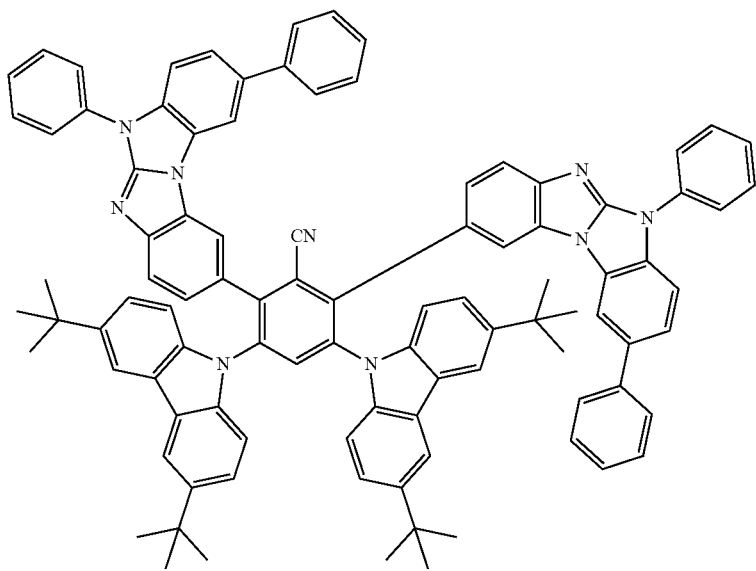
22
23
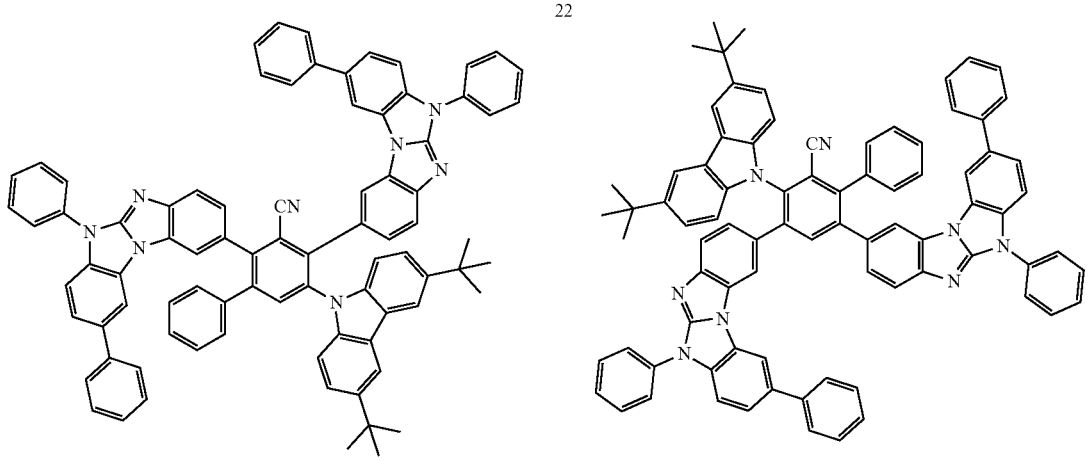
24
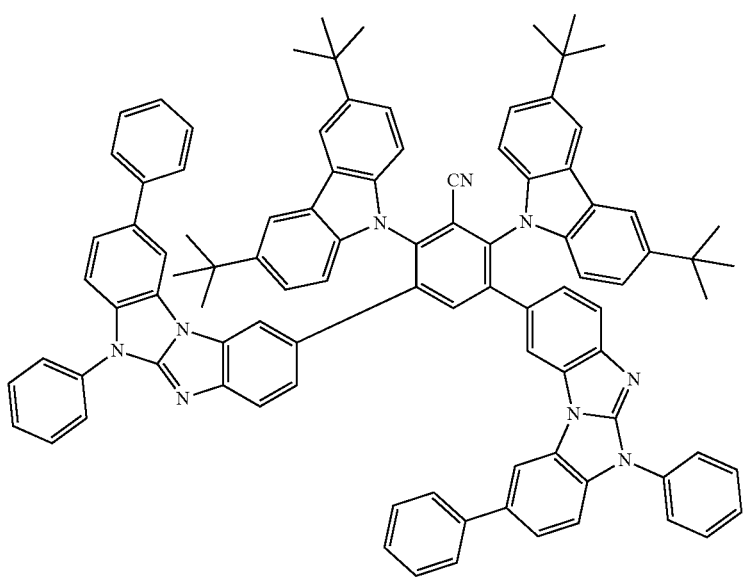

-continued
25
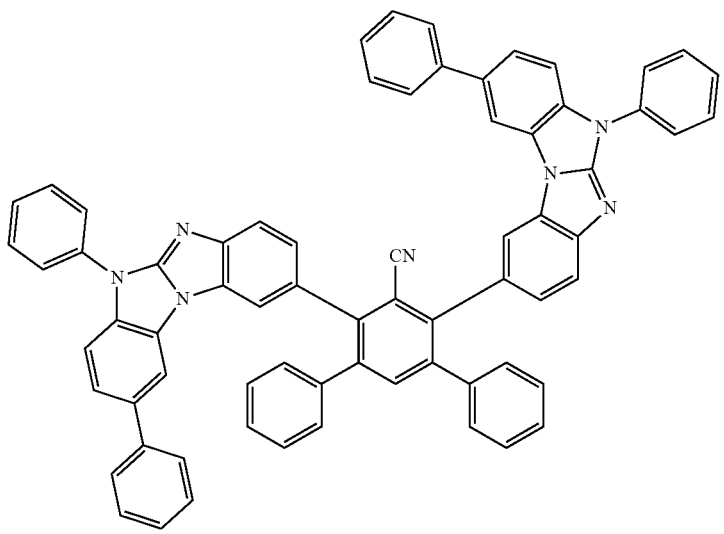
26
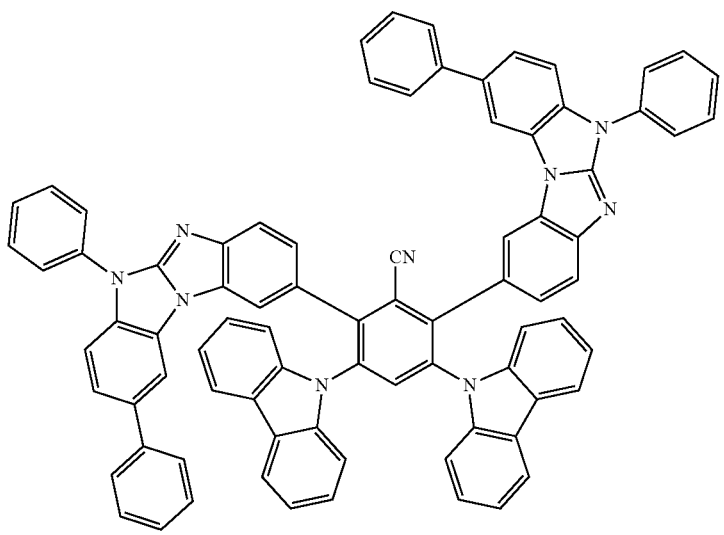
27
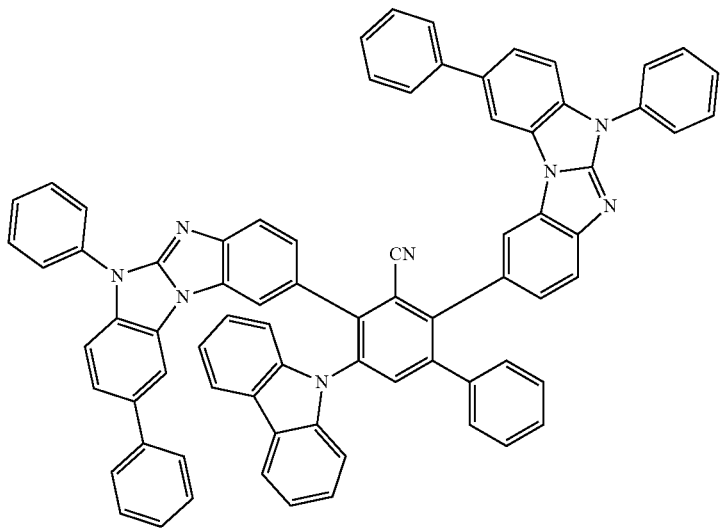

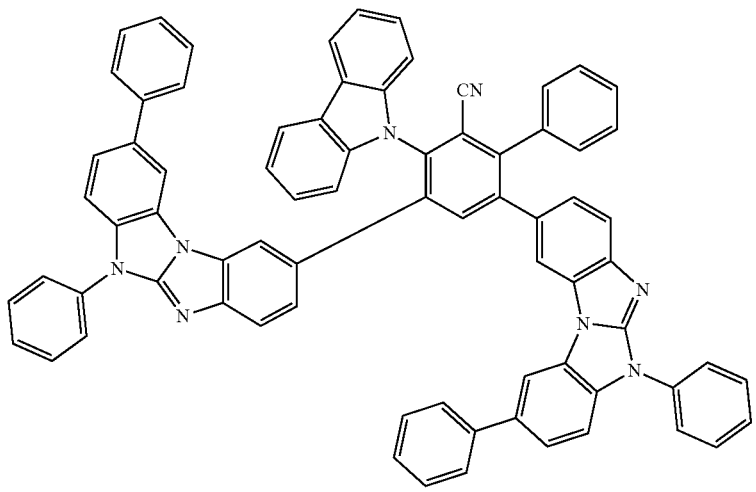
28
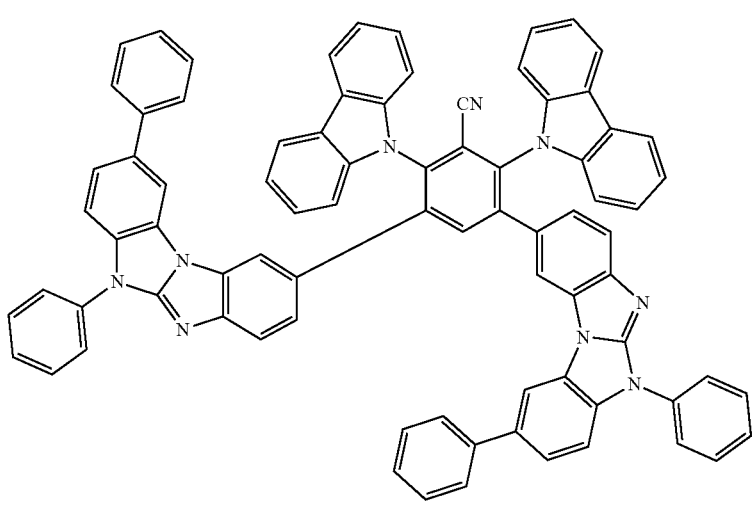
29
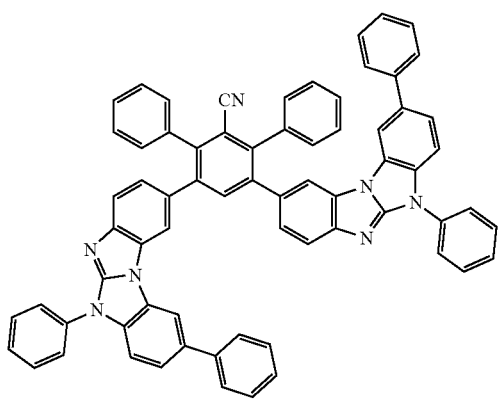
30
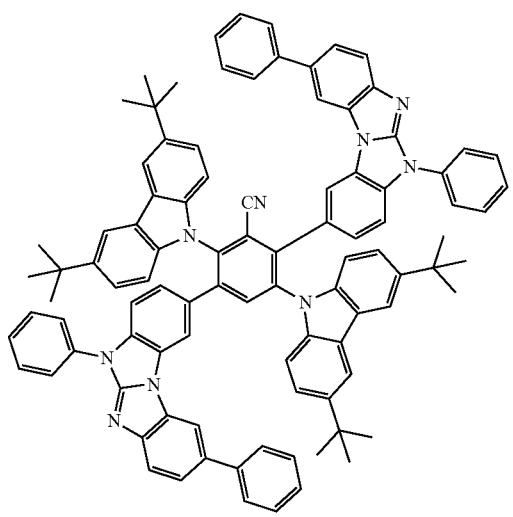
31

32
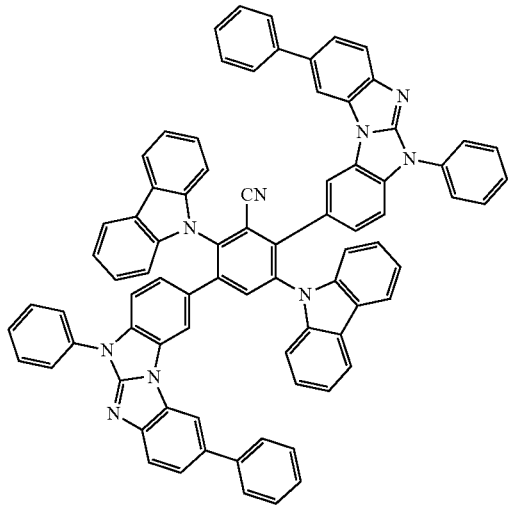
33
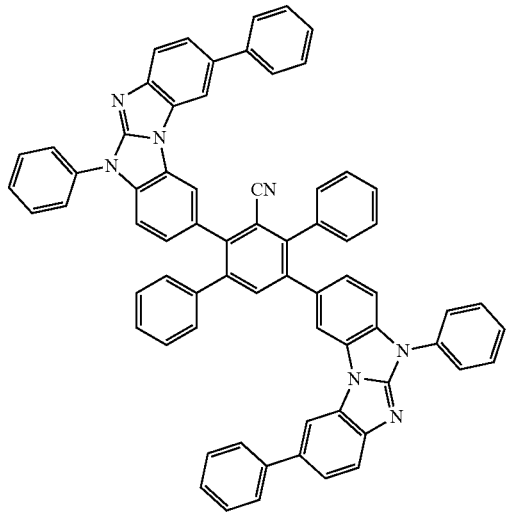
34
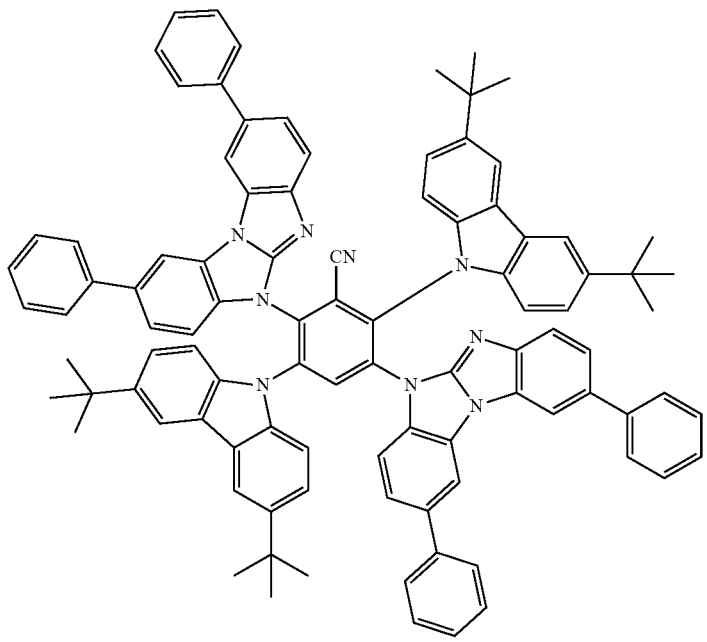

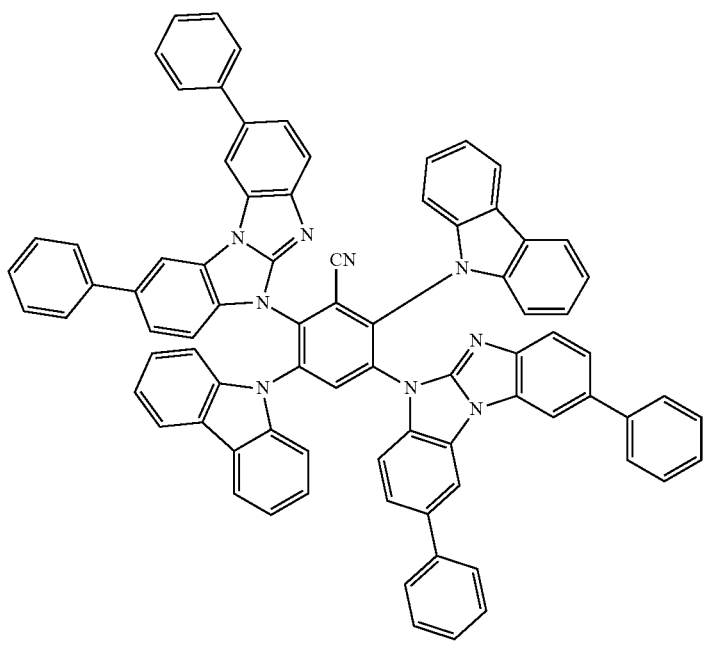
35
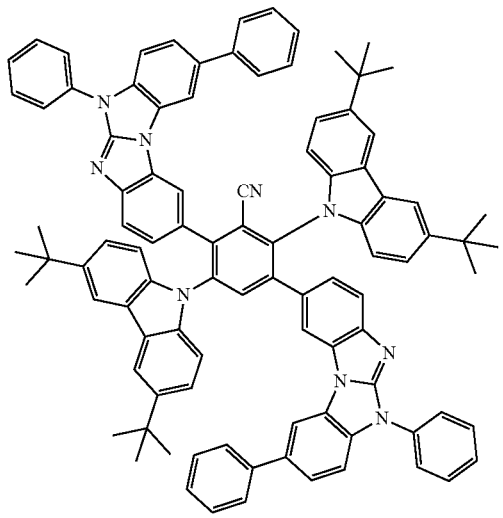
36
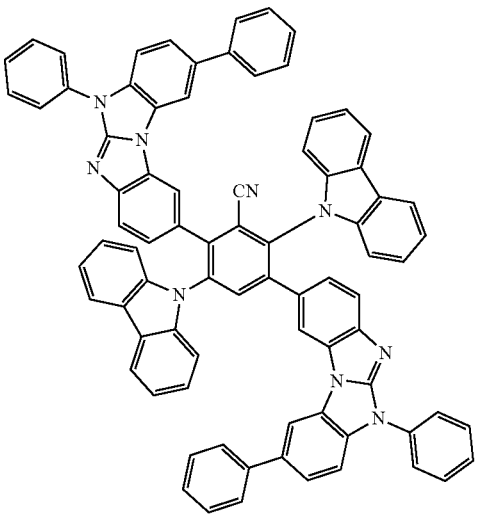
37
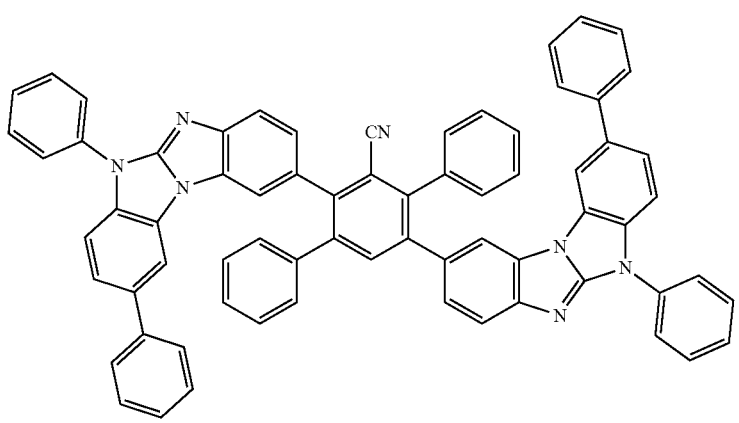
38

-continued

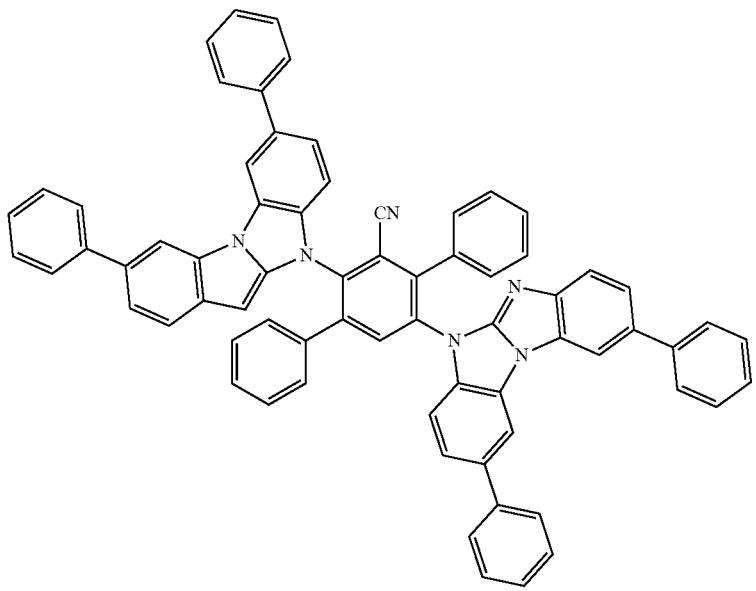

In the case of the condensed-cyclic compound represented by Formula 1, a benzene ring is substituted with four or more substituents having a large steric hindrance. Accordingly, the condensed-cyclic compound may have increased thermal stability and/or material stability.

In the case of the condensed-cyclic compound represented by Formula 1, CN and $A_{11}$ may be substituted at the same time, and may each act as an electron-withdrawing group and an electron-donating group, respectively. Accordingly, regarding the condensed-cyclic compound represented by Formula 1, a highest occupied molecular orbit (HOMO) and a lowest unoccupied molecular orbit (LUMO) may be spatially separated, and therefore, $\Delta E_{ST}$ (herein, $\Delta E_{ST}$ is the difference between a lowest excited singlet energy level ($E_{S1}$) and a lowest excited triplet energy level ($E_{T1}$)) is reduced. Therefore, the condensed-cyclic compound represented by Formula 1 may experience reverse intersystem crossing even at low temperatures (for example, room temperature).

In addition, in the case of the condensed-cyclic compound represented by Formula 1, CN and $A_{11}$ may be positioned adjacent to each other, and in this regard, an electron-withdrawing group may be electronically masked with an electron-donating group. Accordingly, the condensed-cyclic compound represented by Formula 1 may have increased electron stability as well as increased thermal stability and/or increased material stability, thereby improving a lifespan of an organic light-emitting device including the condensed-cyclic compound represented by Formula 1.

The condensed-cyclic compound represented by Formula 1 may satisfy Equation 1:

$$0 \text{ eV} < \Delta E_{ST} \leq 0.5 \text{ eV} \qquad \text{Equation 1}$$

In Equation 1, $\Delta E_{ST}$ is the difference between the lowest excited singlet energy level ($E_{S1}$) of the condensed-cyclic compound represented by Formula 1 and the lowest excited triplet energy level ($E_{T1}$) of the condensed-cyclic compound represented by Formula 1. $E_{T1}$ and $E_{S1}$ are evaluated by using a DFT method of Gaussian program that is structurally optimized at the level of B3LYP/6-31G(d,p).

In particular, the condensed-cyclic compound represented by Formula 1 may satisfy the following Equation 1-1, but embodiments are not limited thereto:

$$0.01 \text{ eV} < \Delta E_{ST} \leq 0.3 \text{ eV} \qquad \text{Equation 1-1}$$

The lowest excited singlet energy level of the condensed-cyclic compound represented by Formula 1 may exceed 2.5 eV and may be less than 3.0 eV, but embodiments are not limited thereto.

For example, the HOMO, LUMO, $T_1$ energy level, $S_1$ energy level, photoluminescence (PL) maximum emission wavelength and oscillator intensity of some of the compounds were evaluated by using a DFT method of Gaussian program (optimized at the level of B3LYP, 6-31G(d,p)), and the obtained results are shown in Table 1.

TABLE 1

| Compound No. | HOMO (eV) | LUMO (eV) | $S_1$ (eV) | $T_1$ (eV) | $S_1$—$T_1$ (eV) | Oscillator strength (f) |
|---|---|---|---|---|---|---|
| 5 | −5.273 | −1.954 | 2.744 | 2.733 | 0.011 | 0.0002 |
| A | −5.346 | −2.087 | 2.773 | 2.701 | 0.072 | 0.0359 |
| B | −5.403 | −2.041 | 2.768 | 2.675 | 0.093 | 0.0239 |

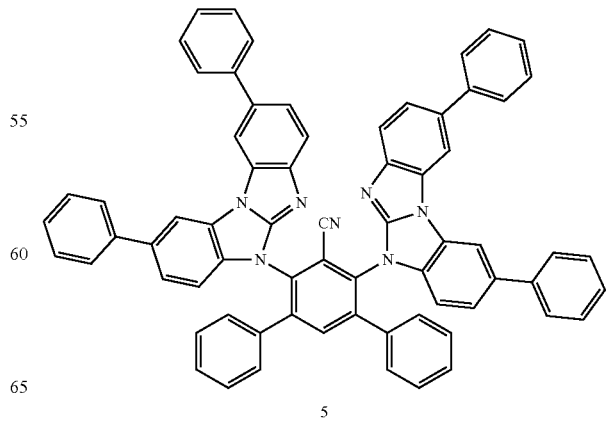

5

TABLE 1-continued

| Compound No. | HOMO (eV) | LUMO (eV) | S$_1$ (eV) | T$_1$ (eV) | S$_1$—T$_1$ (eV) | Oscillator strength (f) |
|---|---|---|---|---|---|---|

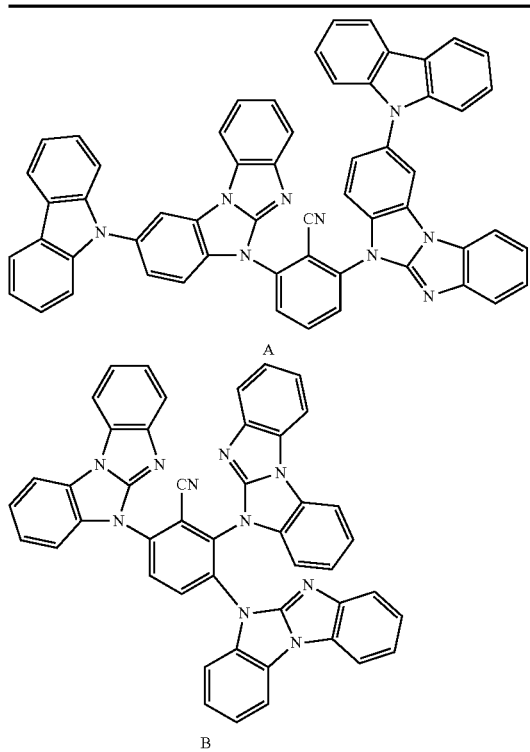

From Table 1, it can be seen that the compound represented by Formula 1 has a relatively small difference between a singlet energy level and a triplet energy level and a low LUMO energy level. Therefore, it can be seen that electronic devices, for example, organic light-emitting devices, employing the compound represented by Formula 1 have improved hole mobility as well as a low driving voltage and high luminescence efficiency.

Synthesis methods of the condensed-cyclic compound represented by Formula 1 may be understood by one of ordinary skill in the art by referring to Synthesis Examples provided below.

The condensed-cyclic compound represented by Formula 1 may be used as a material for electronic devices, for example, organic light-emitting devices. According to one or more embodiments, an organic light-emitting device includes a first electrode; a second electrode; and an organic layer including an emission layer between the first electrode and the second electrode, wherein the organic layer includes the condensed-cyclic compound represented by Formula 1.

When an organic layer including the condensed-cyclic compound represented by Formula 1 is included in an organic light-emitting device, the obtained organic light-emitting device may have low driving voltage, high efficiency, high luminance, high quantum luminance efficiency, and/or long lifespan.

The condensed-cyclic compound of Formula 1 may be used between a pair of electrodes of an organic light-emitting device. For example, the condensed-cyclic compound may be included in an emission layer, a hole transport region between a first electrode and an emission layer (for example, the hole transport region includes a hole injection layer, a hole transport layer, an electron blocking layer, or a combination thereof), an electron transport region between the emission layer and the second electrode (for example, the electron transport region includes a hole blocking layer, an electron transport layer, an electron injection layer, or a combination thereof), or a combination thereof.

Depending on the use of the condensed-cyclic compound represented by Formula 1, the emission layer of the organic light-emitting device may be embodied according to a first embodiment, a second embodiment, and a third embodiment.

First Embodiment

The first embodiment is an embodiment in which the condensed-cyclic compound of Formula 1 included in the emission layer is used as a fluorescent emitter, that is, the condensed-cyclic compound is a fluorescent emitter.

According to the first embodiment, the emission layer consists of the condensed-cyclic compound of Formula 1 alone; or the emission layer may further include a host (hereinafter referred to as 'host A', and the host A is not the same as the condensed-cyclic compound).

Accordingly, according to the first embodiment, the ratio of an emission component emitted from the condensed-cyclic compound of Formula 1 to the total emission components emitted from the emission layer may be 80% or more, for example, 90% or more. For example, the ratio of the emission component emitted from the condensed-cyclic compound to the total emission components emitted from the emission layer may be 95% or more. Herein, the condensed-cyclic compound emits fluorescence and/or delayed fluorescent light, and the emission component of the condensed-cyclic compound may be the sum of prompt emission component of the condensed-cyclic compound and delayed fluorescence component due to reverse intersystem crossing of the condensed-cyclic compound.

In the first embodiment, when the emission layer further includes host A in addition to the condensed-cyclic compound of Formula 1, the amount of the condensed-cyclic compound may be, based on 100 parts by weight of the emission layer, 50 parts by weight or less, for example, 30 parts by weight or less, and the amount of host A in the emission layer may be, based on 100 parts by weight of the emission layer, 50 parts by weight or more, for example, 70 parts by weight or more, but embodiments are not limited thereto.

In the first embodiment, when the emission layer further includes the host A in addition to the condensed-cyclic compound of Formula 1, the host A and the condensed-cyclic compound represented by Formula 1 may satisfy Equation 2:

$$E(H_A)_{S1} > E_{S1} \qquad \text{Equation 2}$$

In Equation 2, $E(H_A)_{S1}$ is the lowest excitation singlet energy level of the host A; and $E_{S1}$ is the lowest excitation singlet energy level of the condensed-cyclic compound represented by Formula 1. $E(H_A)_{S1}$ and $E_{S1}$ are evaluated by using a DFT method of Gaussian program that is structurally optimized at the level of B3LYP/6-31G(d,p).

When the condensed-cyclic compound represented by Formula 1 satisfies Equation 1 and the condensed-cyclic compound represented by Formula 1 and the host A satisfy Equation 2, the condensed-cyclic compound represented by Formula 1 may emit fluorescent light and/or delayed fluorescent light. Therefore, the luminance efficiency of an organic light-emitting device including the condensed-cyclic compound represented by Formula 1 and the host A may be increased.

For example, the host A may be a host material to be described later, but embodiments are not limited thereto.

Second Embodiment

The second embodiment is an embodiment in which the condensed-cyclic compound contained in the emission layer is used as a host.

According to the second embodiment, the emission layer includes a host and a dopant, and the host may include the condensed-cyclic compound represented by Formula 1. That is, the host may consist of the condensed-cyclic compound represented by Formula 1 alone, or may include other known hosts. The dopant may be, for example, a fluorescent dopant, a phosphorescent dopant, or a thermal activation delayed fluorescent dopant.

Therefore, according to the second embodiment, the ratio of the light of the dopant in the total emission components emitted from the emission layer may be 80% or more, for example, 90% or more (as another example, 98% or more).

In the second embodiment, the amount of dopant in the emission layer may be, based on 100 parts by weight of the emission layer, 50 parts by weight or less, for example, 30 parts by weight or less, and the amount of the host in the emission layer may be, based on 100 parts by weight of the emission layer, 50 parts by weight or more, for example, 70 parts by weight or more, but embodiments are not limited thereto.

For example, in the second embodiment, when the dopant is a fluorescent dopant (hereinafter 'fluorescent dopant A'), the condensed-cyclic compound represented by Formula 1 and the fluorescent dopant A may satisfy Equation 3:

$$E_{S1} > E(F_A)_{S1} \quad \quad \text{Equation 3}$$

In Equation 3, $E_{S1}$ is the lowest excitation singlet energy level of the condensed-cyclic compound represented by Formula 1; and $E(F_A)_{S1}$ is the lowest excitation singlet energy level of the fluorescent dopant A.

$E_{S1}$ and $E(F_A)_{S1}$ are evaluated by using a DFT method of Gaussian program that is structurally optimized at the level of B3LYP/6-31G(d,p)

When the condensed-cyclic compound represented by Formula 1 and the fluorescent dopant A satisfy Equation 3, Forster energy transfer from the condensed-cyclic compound represented by Formula 1 to the fluorescent dopant A may be promoted. Therefore, the luminance efficiency of an organic light-emitting device including the condensed-cyclic compound represented by Formula 1 and the fluorescent dopant A may be increased For example, the dopant may be a dopant material to be described later, but embodiments are not limited thereto.

When the host contains other known hosts, the other known hosts may be the host materials described below, but not necessarily limited thereto.

Third Embodiment

The third embodiment is an embodiment in which the condensed-cyclic compound represented by Formula 1 contained in the emission layer is used as an auxiliary dopant.

According to the third embodiment, the emission layer includes a host, an auxiliary dopant, and a dopant, and the auxiliary dopant may include the condensed-cyclic compound. The dopant may be, for example, a fluorescent dopant, a phosphorescent dopant, or a thermal activation delayed fluorescent dopant.

Therefore, according to the third embodiment, the ratio of the light emission component of the dopant in the total light emission components emitted from the may be 80% or more, for example, 90% or more (as another example, 95% or more).

In the third embodiment, the amount of dopant in the emission layer may be, based on 100 parts by weight of the emission layer, 50 parts by weight or less, for example, 30 parts by weight or less, the amount of the host in the emission layer may be, based on 100 parts by weight of the emission layer, 50 parts by weight or more, for example, 70 parts by weight or more, and the amount of the auxiliary dopant may be, based on 100 parts by weight of the emission layer, 30 parts by weight or less, for example, 20 parts by weight or less, but embodiments are not limited thereto.

For example, in the third embodiment, when the dopant is a fluorescent dopant (hereinafter, referred to as 'fluorescent dopant B'), the host (hereinafter referred to as 'host B), the condensed-cyclic compound represented by Formula 1 and the fluorescent dopant B may satisfy Equation 4:

$$E(H_B)_{S1} > E_{S1} > E(F_B)_{S1} \quad \quad \text{Equation 4}$$

In Equation 4, $E(H_B)_{S1}$ is the lowest excitation singlet energy level of the host B;

$E_{S1}$ is the lowest excitation singlet energy level of the condensed-cyclic compound represented by Formula 1; and;

$E(F_B)_{S1}$ is the lowest excitation singlet energy level of the fluorescent dopant B.

$E(H_B)_{S1}$, $E_{S1}$, and $E(F_B)_{S1}$ are evaluated by using a DFT method of Gaussian program that is structurally optimized at the level of B3LYP/6-31G(d,p).

When the host B, the condensed-cyclic compound represented by Formula 1 and the fluorescent dopant B satisfy Equation 4, Forster energy transfer from the condensed-cyclic compound represented by Formula 1 to the fluorescent dopant B may be promoted. Therefore, the luminance efficiency of an organic light-emitting device including host B, the condensed-cyclic compound represented by Formula 1 and the fluorescent dopant B may be increased The host B and the condensed-cyclic compound represented by Formula 1 may satisfy Equation 5:

$$E(H_B)_{T1} - E_{T1} > 0.05 \text{ eV} \quad \quad \text{Equation 5}$$

In Equation 5, $E(H_B)_{T1}$ is the lowest excitation triplet energy level of the host B; and $E_{T1}$ is the lowest excitation triplet energy level of the condensed-cyclic compound represented by Formula 1.

$E(H_B)_{T1}$ and $E_{T1}$ are evaluated by using a DFT method of Gaussian program that is structurally optimized at the level of B3LYP/6-31G(d,p).

In the third embodiment, due to the satisfaction of Equation 5 (for example, $E(H_B)_{T1} - E_{T1}$ is 0.10 eV or more and 0.65 eV or less), the energy of the triplet exciton generated in the auxiliary dopant in the emission layer may not be transferred to the host B in the emission layer. Accordingly, the probability of the triplet exciton being lost in a path other than the light emission path is reduced. As a result, the organic light-emitting device may have high efficiency.

The condensed-cyclic compound represented by Formula 1 and the fluorescent dopant B may satisfy Equation 6:

$$E(F_B)_{S1} - E_{S1} < 0 \text{ eV} \quad \quad \text{Equation 6}$$

In Equation 6,

E(F$_B$)$_{S1}$ is the lowest excitation singlet energy level of the fluorescent dopant, and E$_{S1}$ is the lowest excitation triplet energy level of the condensed-cyclic compound represented by Formula 1.

E(F$_B$)$_{S1}$ and E$_{S1}$ are evaluated by using a DFT method of Gaussian program that is structurally optimized at the level of B3LYP/6-31G(d,p).

In the third embodiment, due to the satisfaction of Equation 6 (for example, E$_{S1(FD)}$-E$_{S1(AD)}$ is -0.4 eV or more and -0.05 eV or less), the energy of singlet exciton generated in the auxiliary dopant in the emission layer may quickly move toward the fluorescent dopant B. Thus, substantially, only the fluorescent dopant B in the emission layer of the organic light-emitting device emits light, thereby realizing a fluorescence emission spectrum of excellent color purity based on the fluorescent dopant B. In addition, a fluorescence emission having a relatively short exciton lifespan may occur. Accordingly, the efficiency transfer phenomenon under high luminosity (that is, a roll-off phenomenon), which may occur due to the interaction among a plurality of excitons (exciton-exciton interaction) or exciton-charge (hole or electron) interaction (exciton-polaron interaction) may be suppressed, thereby leading to the embodiment of an organic light-emitting device having high efficiency. Furthermore, since the auxiliary dopant has a short exciton lifespan, the probability in which the auxiliary dopant experiences chemical or physical deterioration when in the exciton state may be reduced. Thus, an organic light-emitting device satisfying Equation 6 has increased durability.

In the third embodiment, the host may be a host material to be described later, but embodiments are not limited thereto In the third embodiment, the dopant may be a dopant material to be described later, but embodiments are not limited thereto.

For example, the host may have 2.9 eV or more of triplet energy level, for example, 2.9 eV or more and 4.5 eV or less of triplet energy level. As a result, energy transfer from the host to a fluorescent dopant, a phosphorescent dopant and/or a delayed fluorescent dopant may be effectively performed, and the organic light-emitting device may have high efficiency.

For example, the host may include a fluorene-containing compound, a carbazole-containing compound, a dibenzothiophene-containing compound, a dibenzothiophene-containing compound, an indenocarbazole-containing compound, an indolocarbazole-containing compound, a benzofurocarbazole-containing compound, a benzothienocarbazole-containing compound, an acridine-containing compound, a dihydroacridine-containing compound, a triindolobenzene-containing compound, a pyridine-containing compound, a pyrimidine-containing compound, a triazine-containing compound, a silicon-containing compound, a cyano-containing compound, a phosphine oxide-containing compound, a sulfoxide-containing compound, or a combination thereof, but embodiments are not limited thereto.

In one embodiment, the host may include a compound including a carbazole ring and a cyano group For example, the host may include compounds represented by Formulae 11-1 to 11-3, but embodiments are not limited thereto:

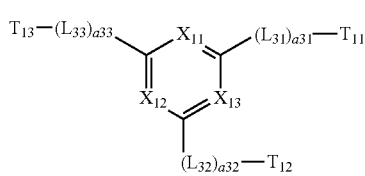

Formula 11-1

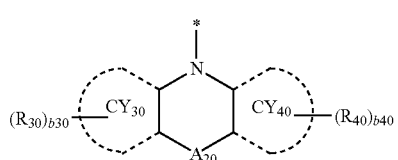

Formula 11-2

Formula 11-3

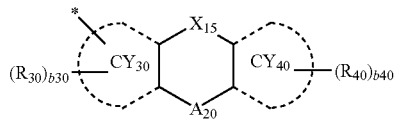

Formula 13

Formula 14

In Formulae 11-1 to 11-3, 13, and 14,

Ar$_{11}$ and Ar$_{12}$ may each independently be group represented by Formulae 13 or 14, X$_{15}$ may be N(R$_{200}$), O, or S, X$_{11}$ may be N or C(T$_{14}$), X$_{12}$ may be N or C(T$_{15}$), and X$_{13}$ may be N or C(T$_{16}$), wherein at least one of X$_{11}$ to X$_{13}$ may be N, T$_{21}$ and T$_{22}$ may each independently be *-(L$_{21}$)$_{a21}$-Si(Q$_{41}$)(Q$_{42}$)(Q$_{43}$) or *-(L$_{21}$)$_{a21}$-P(=O)(Q$_{51}$)(Q$_{52}$), L$_{21}$ and L$_{31}$ to L$_{33}$ may each independently be:

a single bond, O, S, Si(Q$_{61}$)(Q$_{62}$), a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, or a dibenzothiophenylene group; or a phenylene group, a pyridinylene group, a pyrimidinylene group, a pyrazinylene group, a pyridazinylene group, a triazinylene group, a naphthylene group, a fluorenylene group, a carbazolylene group, a dibenzofuranylene group, or a dibenzothiophenylene group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a C$_1$-C$_{10}$ alkoxy group, —CF$_3$, —CF$_2$H, —CFH$_2$, a phenyl group, a phenyl group represented by a cyano group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, —Si(Q$_{71}$)(Q$_{72}$)(Q$_{73}$), or a combination thereof, a21 and a31 to a33 may each independently be an integer from 0 to 5, when a21 is 2 or more, two or more L$_{21}$(s) may be identical to or different from each other, when a31 is 2 or more, two or more L$_{31}$(s) may be identical to or different from each other, when a32 is 2 or more, two or more L$_{32}$(s) may be identical to or different from each other, and when a33 is 2 or more, two or more L$_{33}$(s) may be identical to or different from each other, CY$_{30}$ and CY$_{40}$ may each independently be a benzene group, a naphthalene group, a fluorene group, a carbazole group, a benzocarbazole group, an indolocarbazole group, a dibenzofuran group, or a dibenzothiophene group, $A_{20}$ may be:

a single bond, a $C_1$-$C_4$ alkylene group, or a $C_2$-$C_4$ alkenylene group; or a $C_1$-$C_4$ alkylene group or a $C_2$-$C_4$ alkenylene group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a biphenyl group, a terphenyl group, a naphthyl group, a pyridinyl group, a pyrimidinyl group, a pyrazinyl group, a pyridazinyl group, a triazinyl group, a fluorenyl group, a carbazolyl group, a dibenzofuranyl group, a dibenzothiophenyl group, —Si($Q_{81}$)($Q_{82}$)($Q_{83}$), or a combination thereof, $T_{11}$ to $T_{16}$, $R_{200}$, $R_{30}$, and $R_{40}$ may each independently be hydrogen, deuterium, —F, —Cl, —Br, —I, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, or —Si($Q_{91}$)($Q_{92}$)($Q_{93}$), b30 and b40 may each independently be an integer from 0 to 10, c12 may be 0, 1, 2, or 3,

* indicates a binding site to a neighboring atom, a substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, or the substituted monovalent non-aromatic condensed heteropolycyclic group may be deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or —Si($Q_{101}$)($Q_{102}$)($Q_{103}$), and $Q_{41}$ to $Q_{43}$, $Q_{51}$ to $Q_{52}$, $Q_{61}$ to $Q_{62}$, $Q_{71}$ to $Q_{73}$, $Q_{81}$ to $Q_{83}$, $Q_{91}$ to $Q_9$, and $Q_{101}$ to $Q_{103}$ may each independently be hydrogen, deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group.

For example, the host may include Compounds H-1 to H-27, but embodiments of the present disclosure are not limited thereto:

H-1

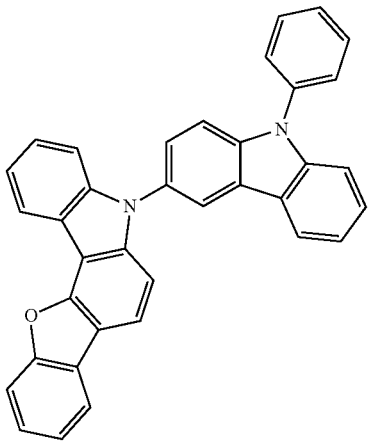

H-2

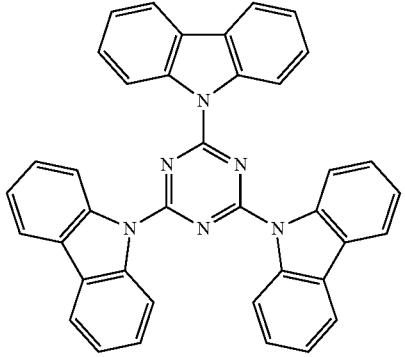

H-3

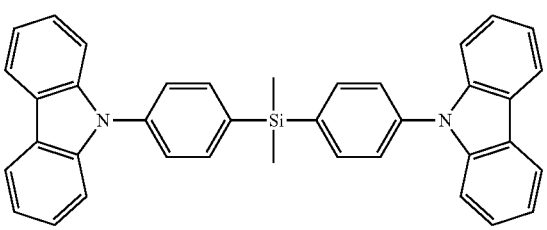

H-4

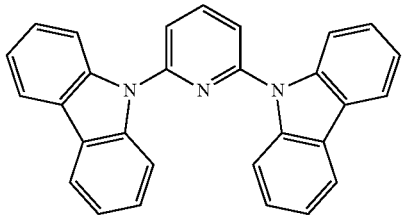

H-5
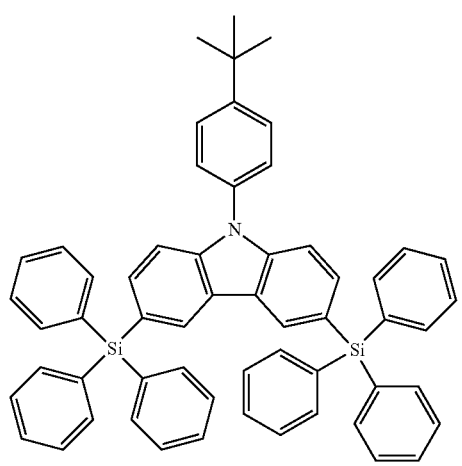
H-6
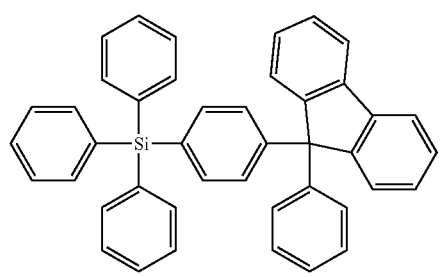
H-7
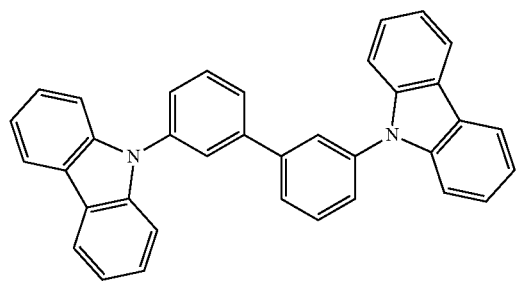
H-8
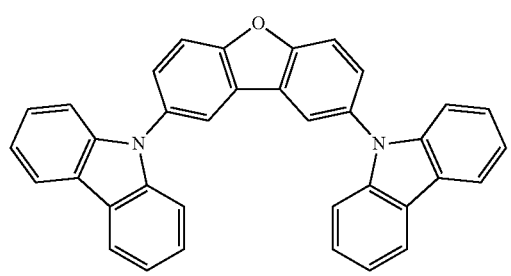
H-9
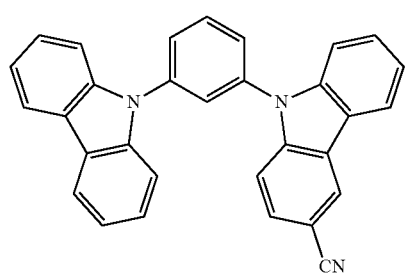
H-10
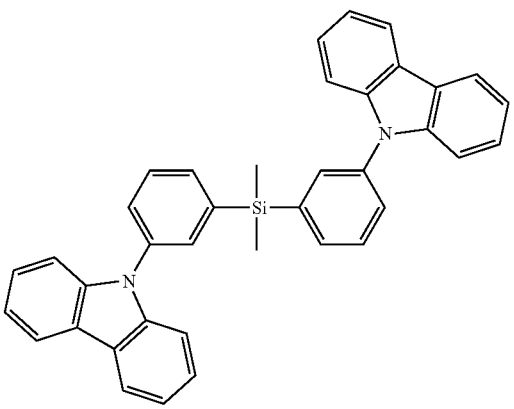
H-11
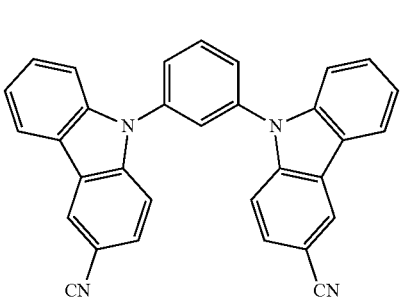
H-12
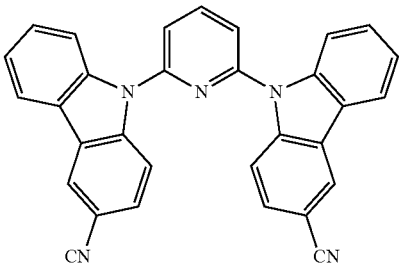
H-13
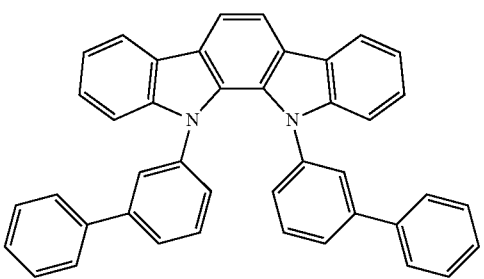
H-14
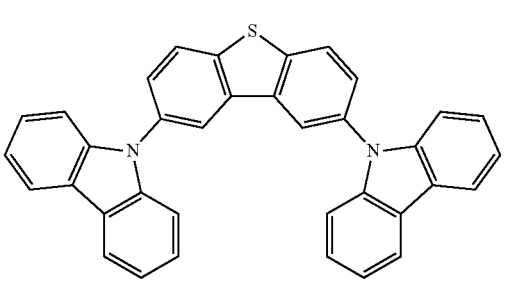

-continued
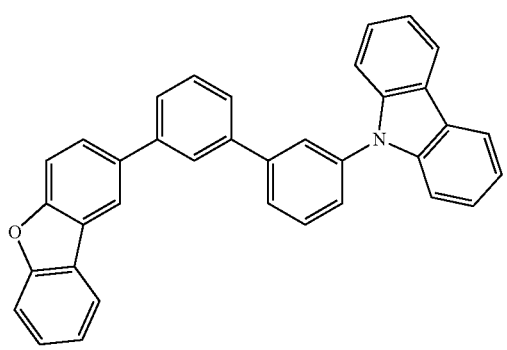
H-15
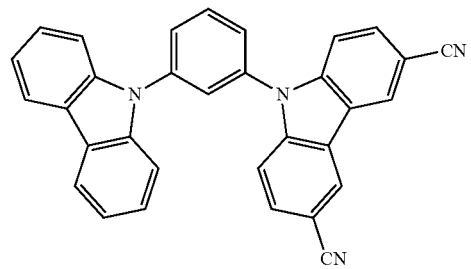
H-19
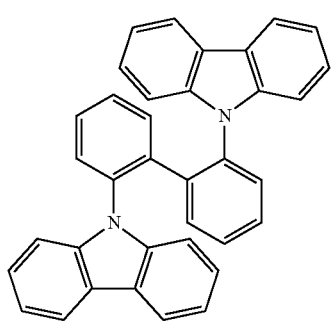
H-16
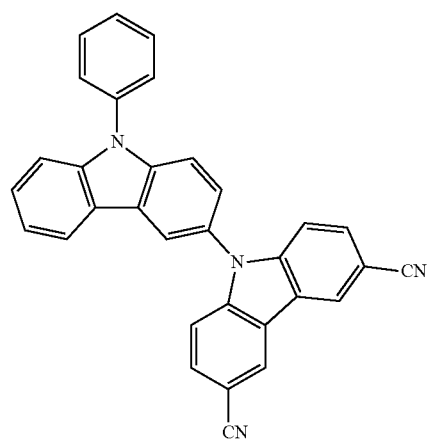
H-20
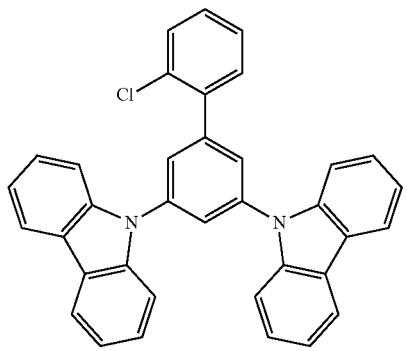
H-17
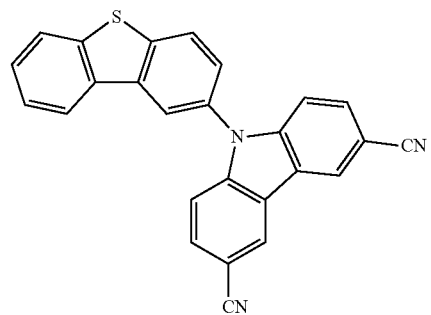
H-21
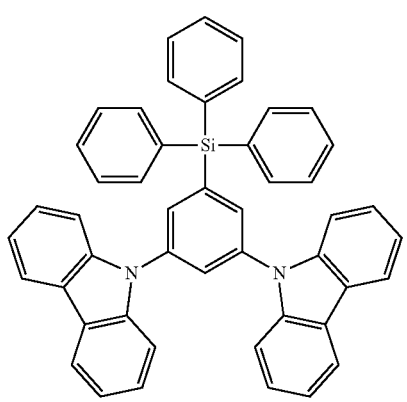
H-18
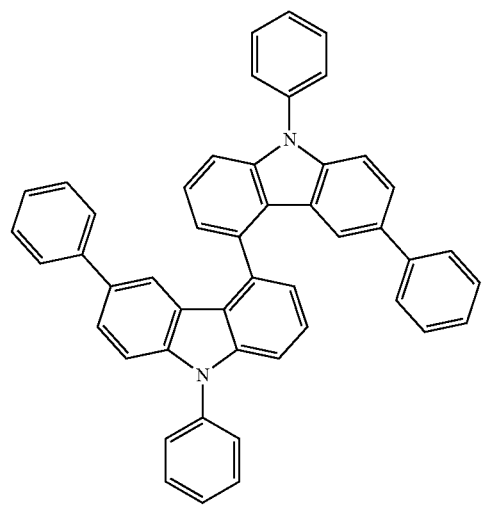
H-22

H-23
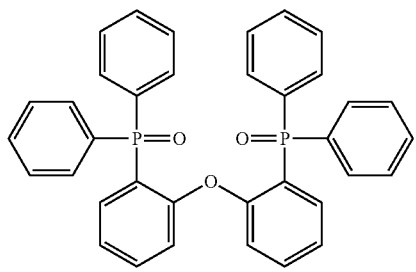

H-24
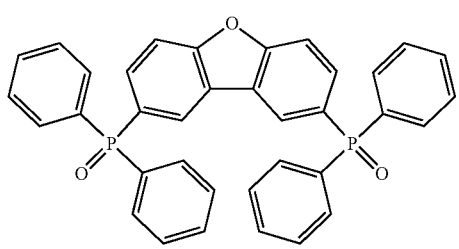

H-25
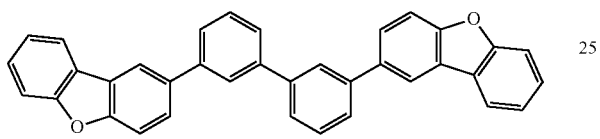

H-26
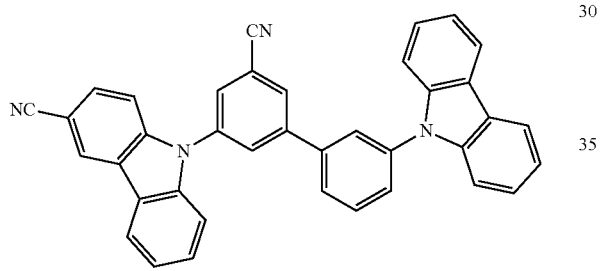

H-27
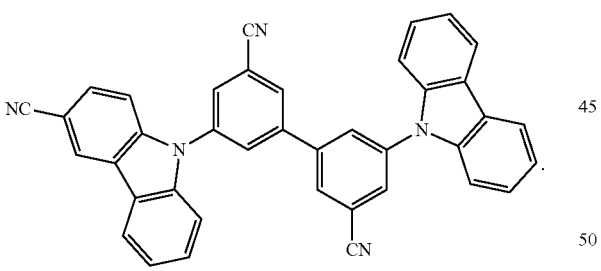

501-1
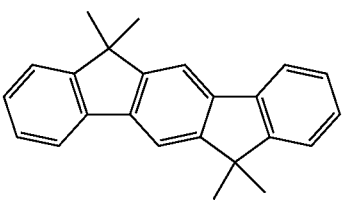

501-2
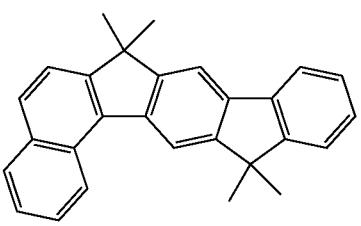

501-3
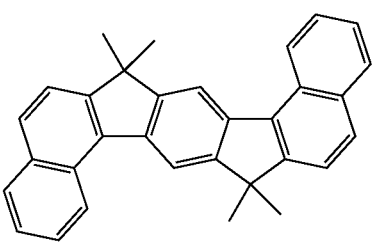

501-4
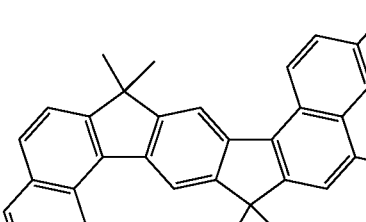

501-5
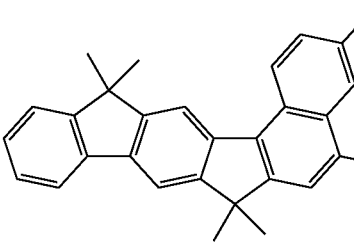

501-6
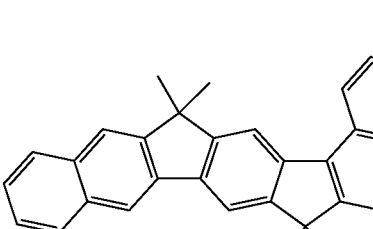

The fluorescent dopant may be a condensed polycyclic compound or a styryl compound.

For example, the fluorescent dopant may include a naphthalene-containing core, a fluorene-containing core, a spirobifluorene-containing core, a benzofluorene-containing core, a dibenzofluorene-containing core, a phenanthrene-containing core, an anthracene-containing core, a fluoranthene-containing core, a triphenylene-containing core, a pyrene-containing core, a chrysene-containing core, a naphthacene-containing core, a picene-containing core, a perylene-containing core, a pentaphene-containing core, an indenoanthracene-containing core, a tetracene-containing core, a bisanthracene-containing core, or a core represented by one of Formulae 501-1 to 501-18, but embodiments of the present disclosure are not limited thereto:

501-7
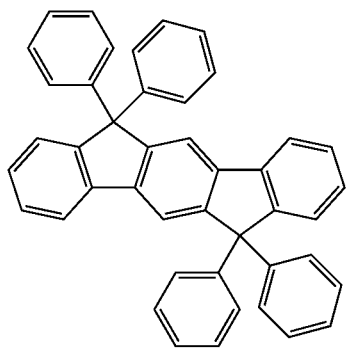
501-8
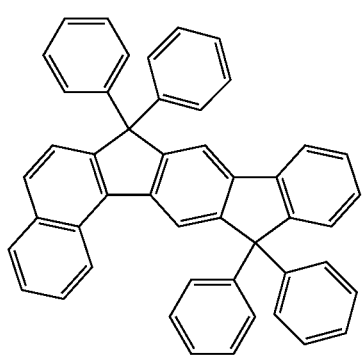
501-9
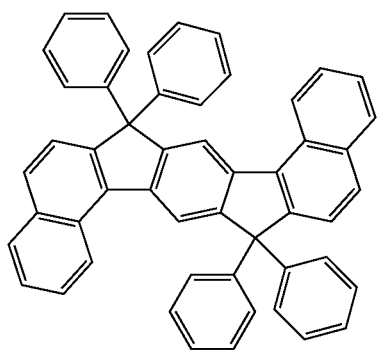
501-10
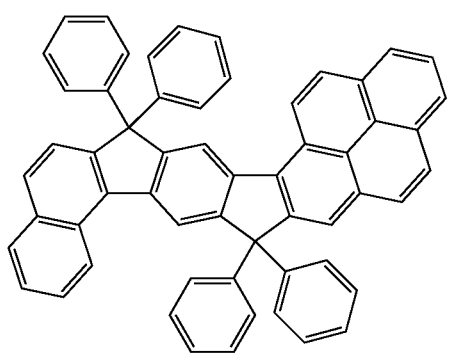
501-11
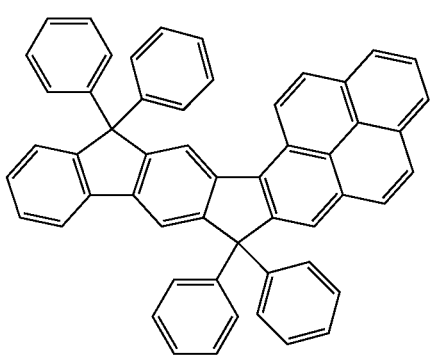
501-12
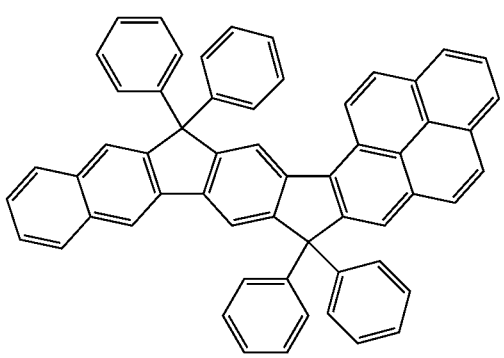
501-13
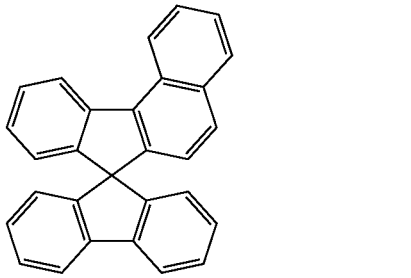
501-14
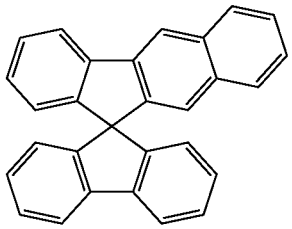
501-15
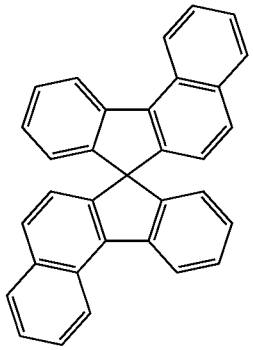

-continued

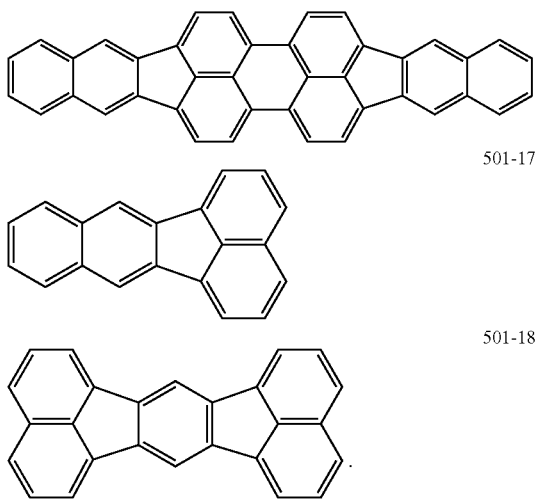

501-16

501-17

501-18

In one or more embodiments, the fluorescent dopant may be a styryl-amine-based compound or a styryl-carbazole-based compound, but embodiments of the present disclosure are not limited thereto.

In one embodiment, the fluorescent dopant may be a group represented by Formula 501:

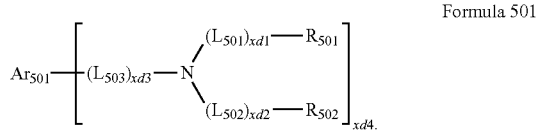

Formula 501

In Formula 501, $Ar_{501}$ may be:

a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, or a group represented by Formulae 501-1 to 501-18; or a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene an indenoanthracene group, a tetracene group, a bisanthracene, or a group represented by Formula 501-1 to 501-18, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{501})(Q_{502})(Q_{503})$ (wherein $Q_{501}$ to $Q_{503}$ may each independently be hydrogen, a $C_1$-$C_{60}$ alkyl group, a $C_1$-$C_{60}$ alkoxy group, a $C_6$-$C_{60}$ aryl group, a $C_1$-$C_{60}$ heteroaryl group, a monovalent non-aromatic condensed polycyclic group, or a monovalent non-aromatic condensed heteropolycyclic group), or a combination thereof, $L_{501}$ to $L_{503}$ may each independently be a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, or a substituted or unsubstituted divalent non-aromatic condensed heteropolycyclic group, $R_{501}$ and $R_{502}$ may each independently be:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, or a dibenzothiophenyl group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, or a combination thereof, xd1 to xd3 may each independently be 0, 1, 2, or 3, and xd4 may be 0, 1, 2, 3, 4, 5, or 6.

For example, in Formula 501, $Ar_{501}$ may be:

a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, or a group represented by one of Formulae 501-1 to 501-18; or a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a naphthacene group, a picene group, a perylene group, a pentaphene group, an indenoanthracene group, a tetracene group, a bisanthracene group, or a group represented by Formulae 501-1 to 501-18, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a dibenzofuranyl group, a dibenzothiophenyl group, a carbazolyl group, a pyridinyl group, a pyrimidinyl group, a triazinyl group, a quinolinyl group, an isoquinolinyl group, or —Si($Q_{501}$)($Q_{502}$)($Q_{503}$) (wherein $Q_{501}$ to $Q_{503}$ may each independently be hydrogen, a $C_1$-$C_{20}$ alkyl group, a $C_1$-$C_{20}$ alkoxy group, a phenyl group, a biphenyl group, a terphenyl group, or a naphthyl group), or a combination thereof, $L_{501}$ to $L_{503}$ may each independently be the same as defined in connection with $L_{21}$, xd1 to xd3 may each independently be 0, 1, or 2, and xd4 may be 0, 1, or 2, but embodiments of the present disclosure are not limited thereto.

In one or more embodiments, the fluorescent dopant may include a compound represented by Formulae 502-1 to 502-5:

Formula 502-1

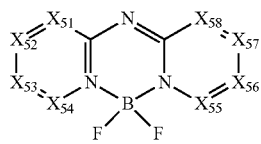

Formula 502-2

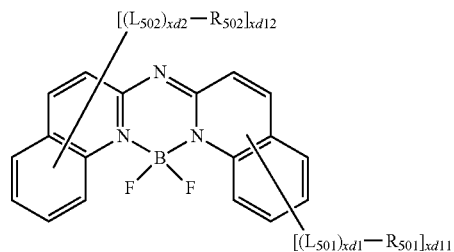

Formula 502-3

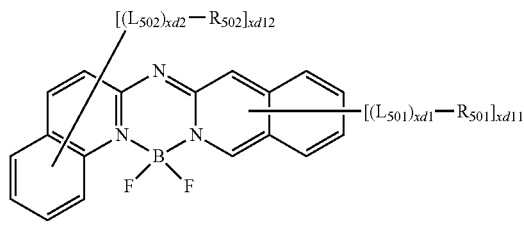

Formula 502-4

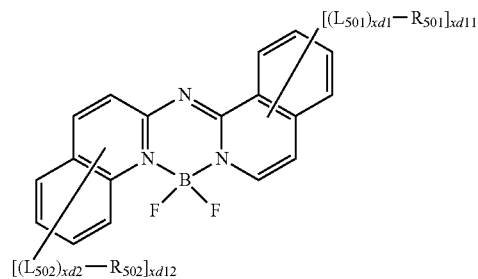

Formula 502-5

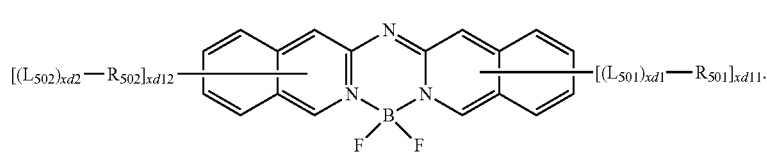

In Formulae 502-1 to 502-5, $X_{51}$ may be N or C-$[(L_{501})_{xd1}$-$R_{501}]$, $X_{52}$ may be N or C-$[(L_{502})_{xd2}$-$R_{502}]$, $X_{53}$ may be N or C-$[(L_{503})_{xd3}$-$R_{503}]$, $X_{54}$ may be N or C$[(L_{504})_{xd4}$-$R_{504}]$, $X_{55}$ may be N or C-$[(L_{505})_{xd5}$-$R_{505}]$, $X_{56}$ may be N or C-$[(L_{506})_{xd6}$-$R_{506}]$, $X_{57}$ may be N or C-$[(L_{507})_{xd7}$-$R_{507}]$, and $X_{58}$ may be N or C-$[(L_{508})_{xd8}$-$R_{508}]$, $L_{501}$ to $L_{508}$ may each independently be the same as defined in connection with $L_{501}$ in Formula 501, xd1 to xd8 may each independently be the same as defined in connection with xd1 in Formula 501.

$R_{501}$ to $R_{508}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, or a dibenzothiophenyl group; or a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, or a dibenzothiophenyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, a dibenzothiophenyl group, or a combination thereof, xd11 and xd12 may each independently be an integer from 0 to 5, two $R_{501}$ to $R_{504}$ may optionally be linked to form a saturated or unsaturated ring, and two $R_{505}$ to $R_{508}$ may optionally be linked to form a saturated or unsaturated ring The fluorescent dopant may include, for example, Compounds FD(1) to FD(16) or FD1 to FD13:

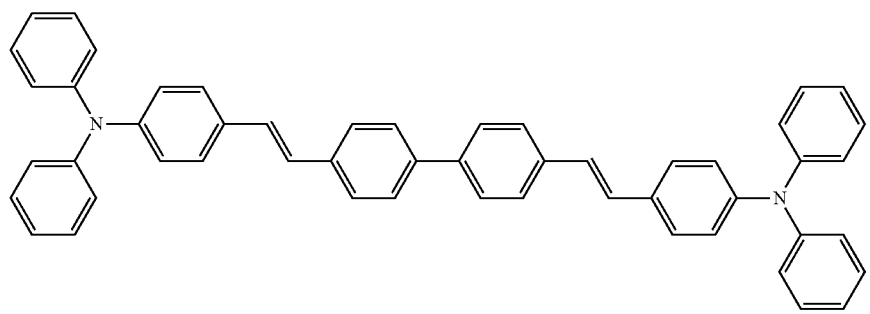

FD(1)

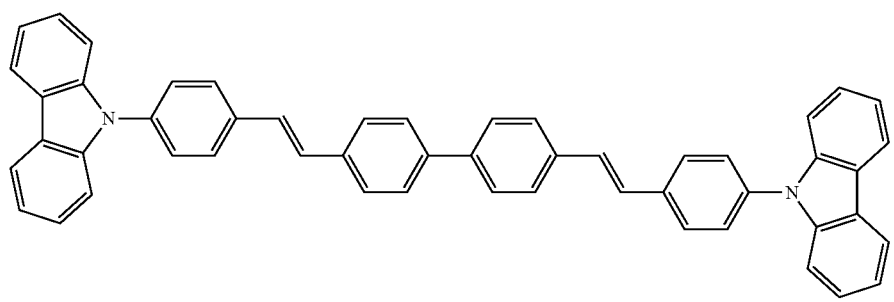

FD(2)

FD(3)
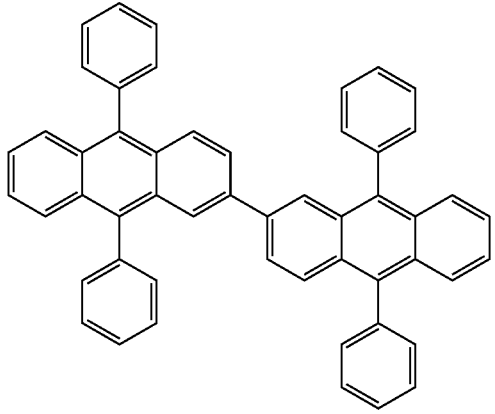
FD(4)
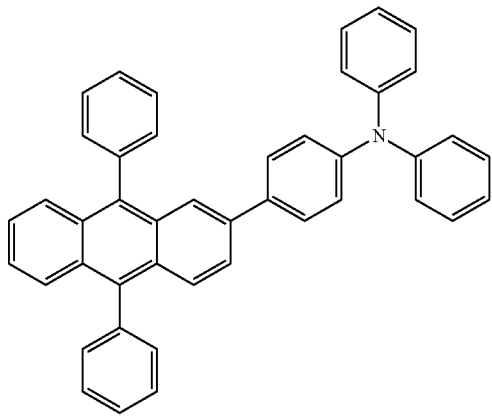
FD(5)
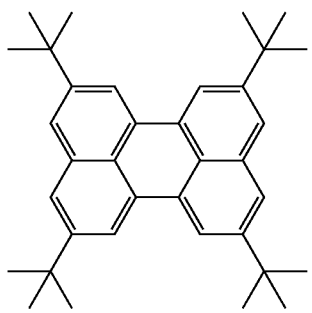
FD(6)
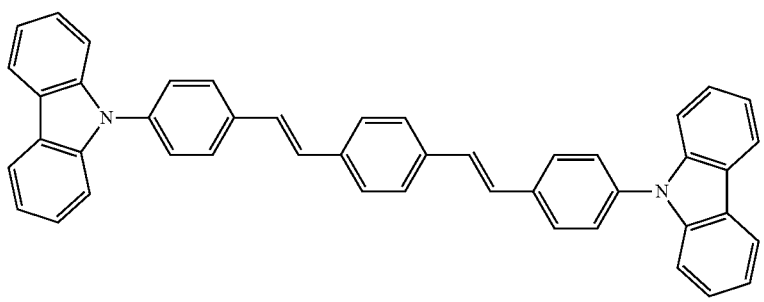
FD(7)
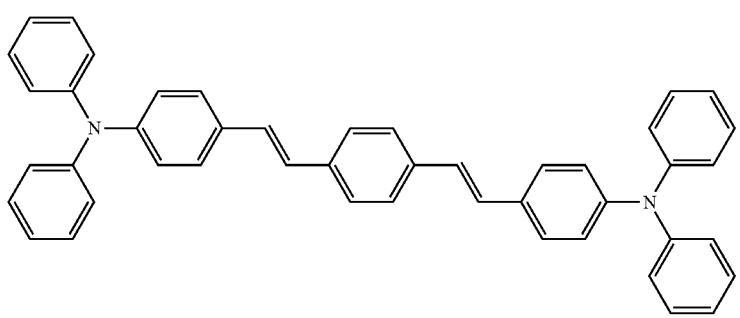

-continued
FD(8)
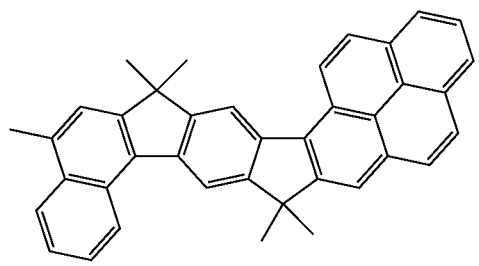
FD(9)
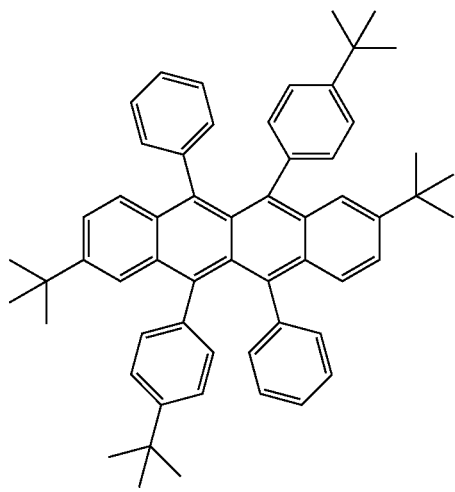
FD(10)
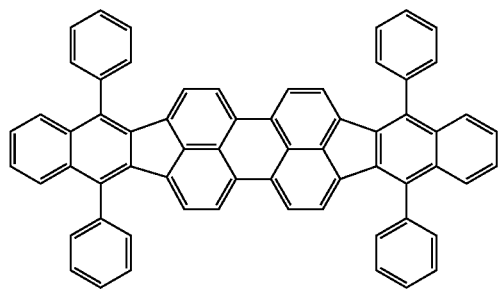
FD(11)
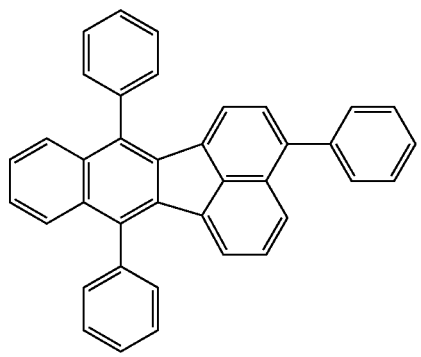
FD(12)
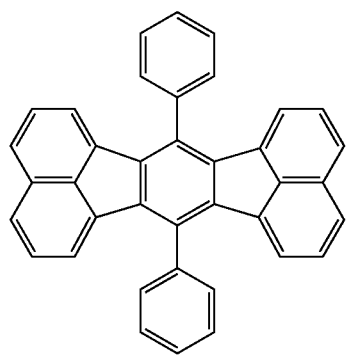
FD(13)
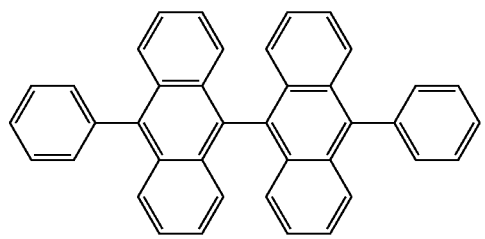
FD(14)
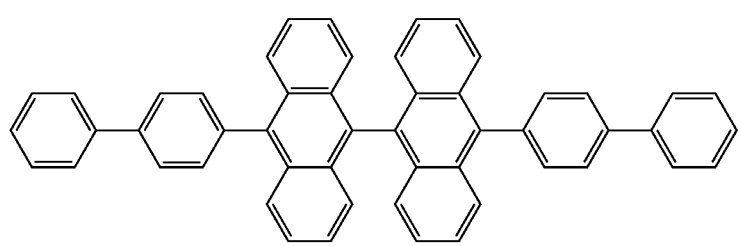

-continued
123 FD(15)
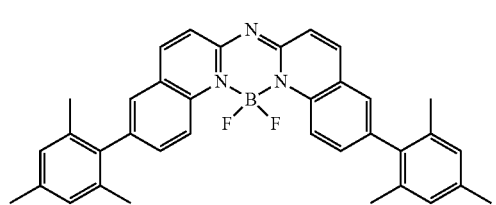
124 FD(16)
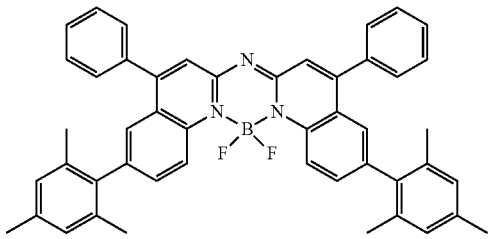
FD1
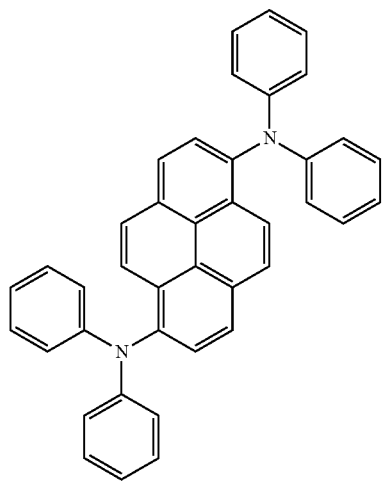
FD2
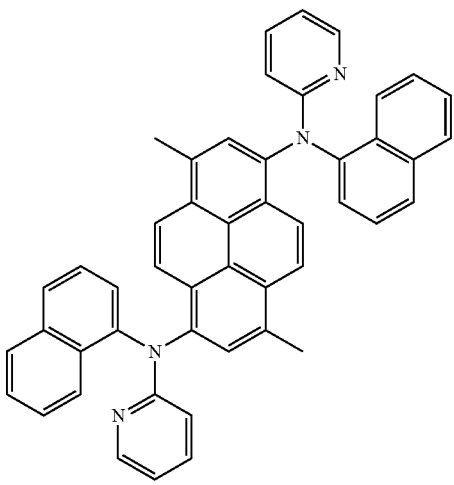
FD3
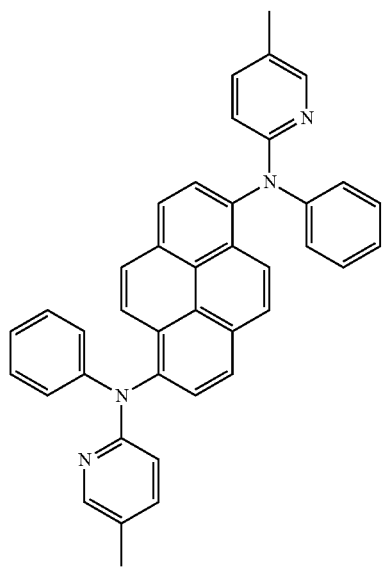
FD4
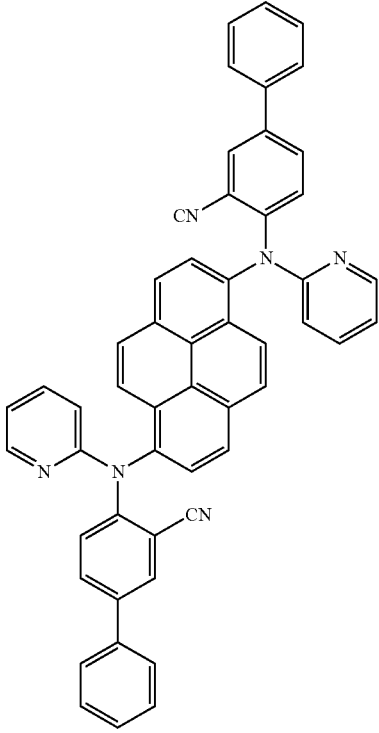

-continued
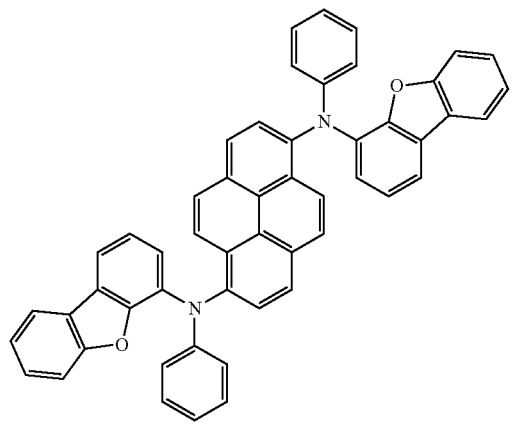
FD5
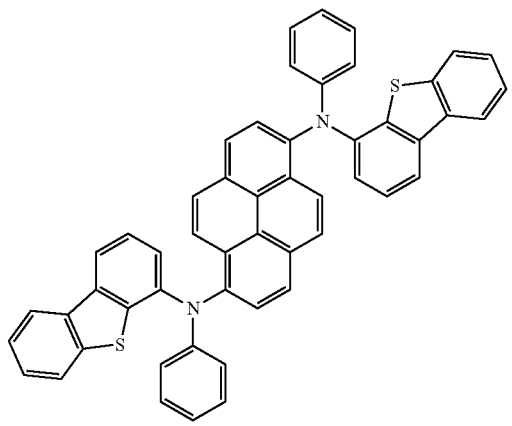
FD6
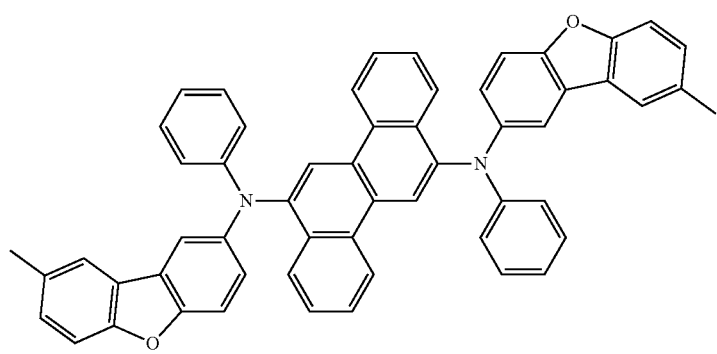
FD7
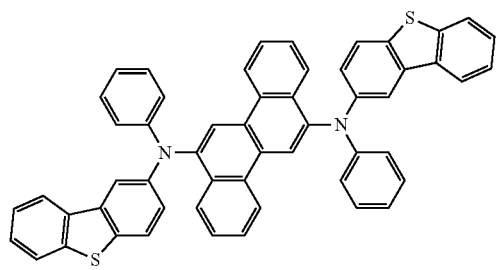
FD8
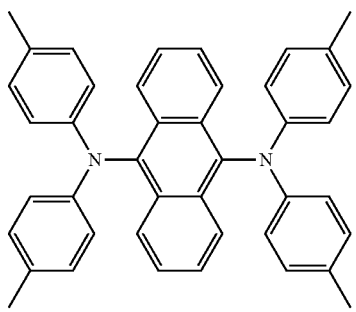
FD9
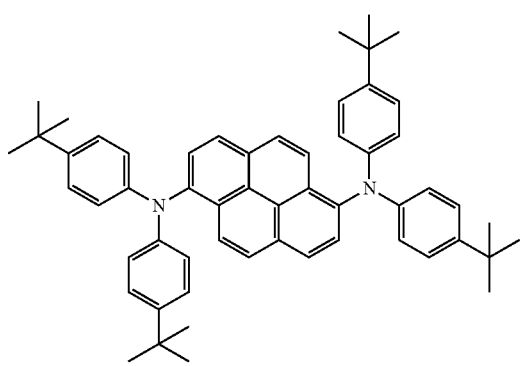
FD10 FD11

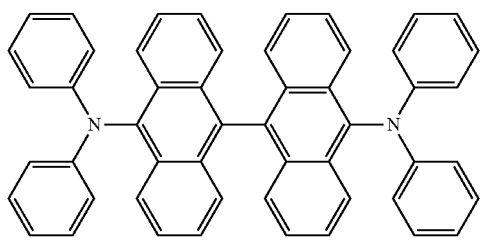
FD12

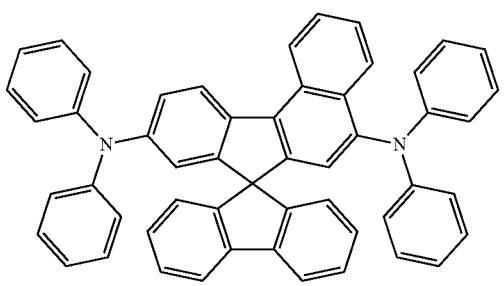
FD13

FIG. 1 is a schematic cross-sectional view of an organic light-emitting device 10 according to one embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked A substrate may be additionally located under the first electrode 11 or above the second electrode 19. For use as the substrate, any substrate that is used in organic light-emitting devices available in the art may be used, and the substrate may be a glass substrate or a transparent plastic substrate, each having excellent mechanical strength, thermal stability, transparency, surface smoothness, ease of handling, and water resistance.

The first electrode 11 may be formed by depositing or sputtering a material for forming the first electrode 11 on the substrate. The first electrode 11 may be an anode. The material for forming the first electrode 11 may be a material with a high work function to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), or zinc oxide (ZnO). In one or more embodiments, the material for forming the first electrode 11 may be metal or an alloy, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 11 is not limited thereto.

The organic layer 15 is located on the first electrode 11.
The organic layer 15 may include a hole transport region, an emission layer, and an electron transport region.

The hole transport region may be between the first electrode 11 and the emission layer.

The hole transport region may include a hole injection layer, a hole transport layer, an electron blocking layer, a buffer layer or a combination thereof.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer, the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100° C. to about 500° C., a vacuum pressure of about 10-8 to about 10-3 torr, and a deposition rate of about 0 Å/sec to about 100 Å/sec. However, the deposition conditions are not limited thereto, but embodiments of the present disclosure are not limited thereto.

When the hole injection layer is formed using spin coating, coating conditions may vary according to the material used to form the hole injection layer, and the structure and thermal properties of the hole injection layer. For example, a coating speed may be from about 2,000 rpm to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include, for example, m-MTDATA, TDATA, 2-TNATA, NPB, β-NPB, TPD, spiro-TPD, spiro-NPB, methylated-NPB, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) PANI/PSS), a compound represented by Formula 201, a compound represented by Formula 202, or a combination thereof, -continued
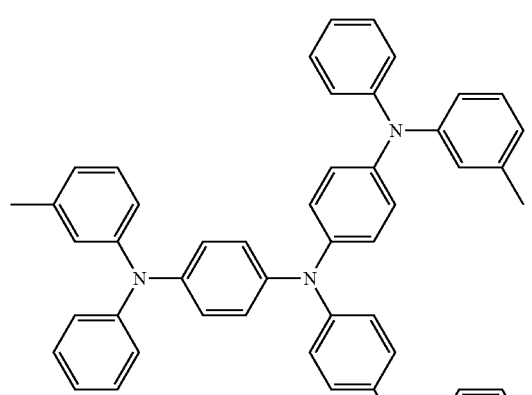
m-MTDATA
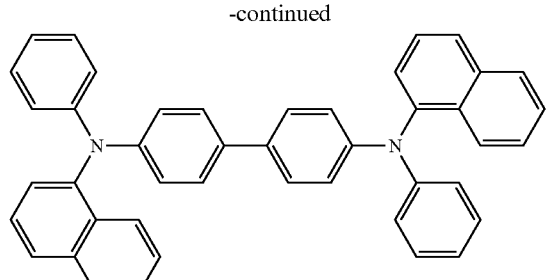
NPB
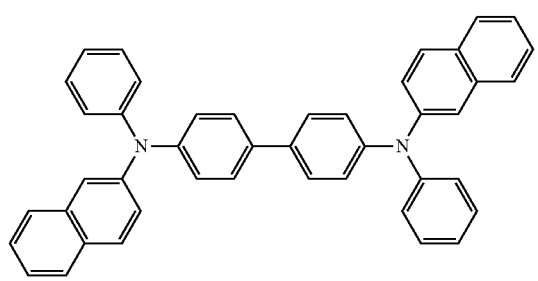
β-NPB
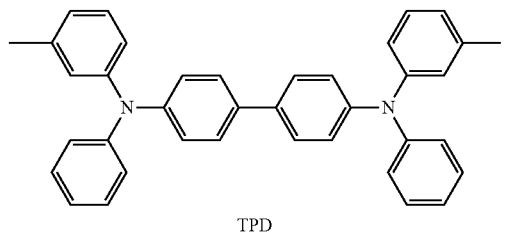
TPD
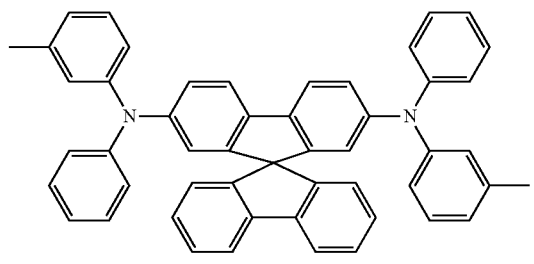
Spiro-TPD
TDATA
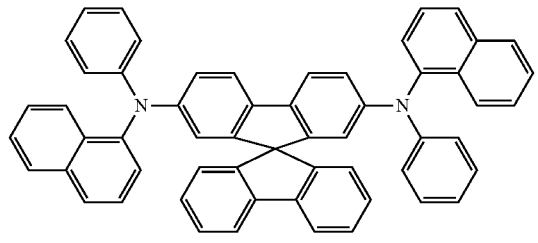
Spiro-NPB
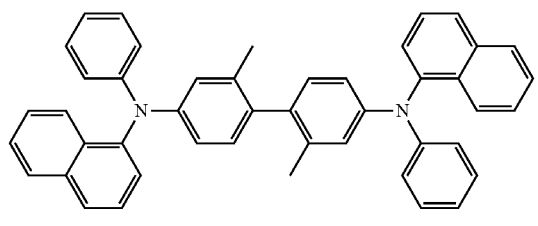
methylated NPB
2-TNATA

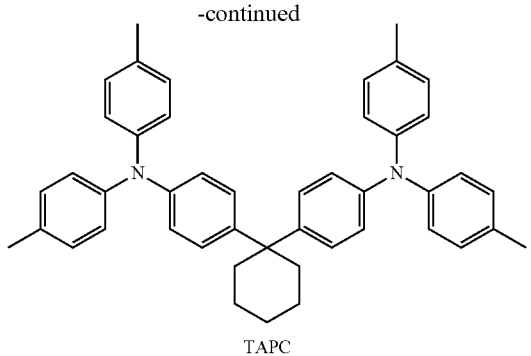

TAPC

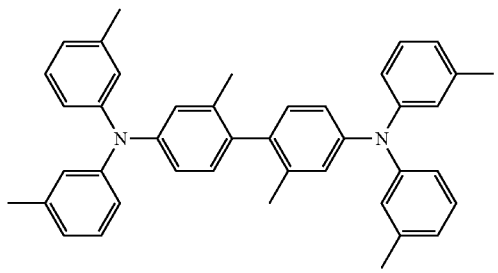

HMTPD

Formula 201

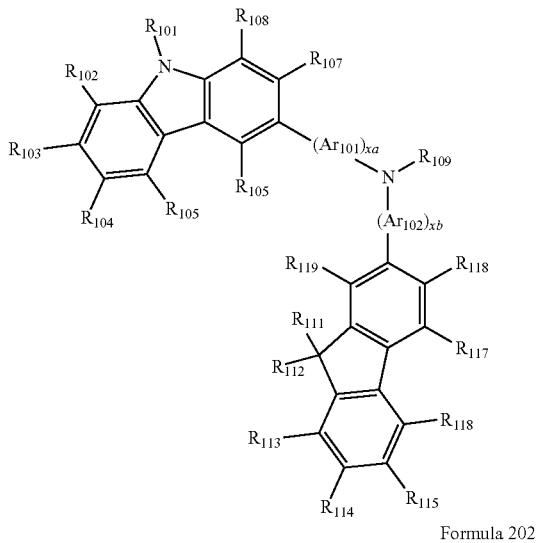

Formula 202

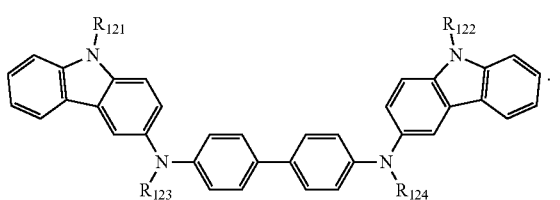

In Formula 201, $Ar_{101}$ and $Ar_{102}$ may each independently be:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, or a pentacenylene group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, or a combination thereof.

In Formula 201, xa and xb may each independently be an integer from 0 to 5, or may be 0, 1, or 2. For example, xa may be 1, and xb may be 0, but embodiments of the present disclosure are not limited thereto.

In Formulae 201 and 202, $R_{101}$ to $R_{108}$, $R_{111}$ to $R_{119}$, and $R_{121}$ to $R_{124}$ may each independently be:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, pentyl group, a hexyl group, and the like), or a $C_1$-$C_{10}$ alkoxy group (for example, a methoxy group, an ethoxy group, a propoxy group, a butoxy group, a pentoxy group, and the like);

a $C_1$-$C_{10}$ alkyl group or a $C_1$-$C_{10}$ alkoxy group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, or a combination thereof;

a phenyl group, a naphthyl group, an anthracenyl group, a fluorenyl group, or a pyrenyl group; or a phenyl group, a naphthyl group, an anthracenyl group, a fluorenyl group, or a pyrenyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, or a combination thereof.

but embodiments of the present disclosure are not limited thereto.

In Formula 201, $R_{109}$ may be:

a phenyl group, a naphthyl group, an anthracenyl group, or a pyridinyl group; or a phenyl group, a naphthyl group, an anthracenyl group, or a pyridinyl group, each substituted with deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, a pyridinyl group, or a combination thereof.

In one embodiment, the compound represented by Formula 201 may be represented by Formula 201A, but embodiments of the present disclosure are not limited thereto:

Formula 201A

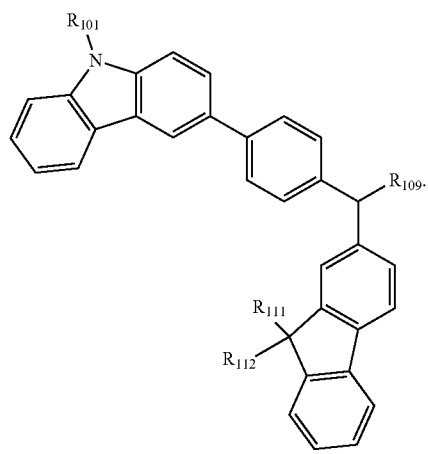

Detailed descriptions of $R_{101}$, $R_{111}$, $R_{112}$, and $R_{109}$ in Formula 201A are the same as described above.

For example, the compound represented by Formula 201 and the compound represented by Formula 202 may include Compounds HT1 to HT20 but are not limited thereto:

HT1

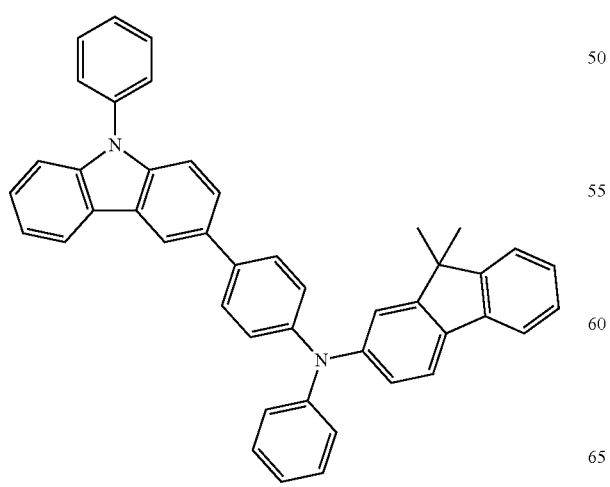

HT2

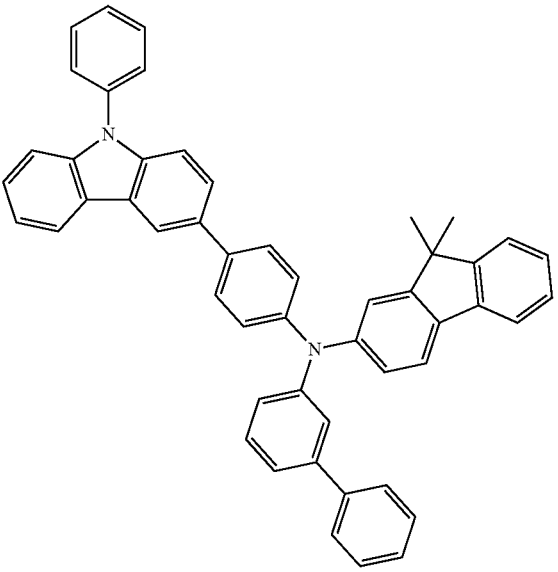

HT3

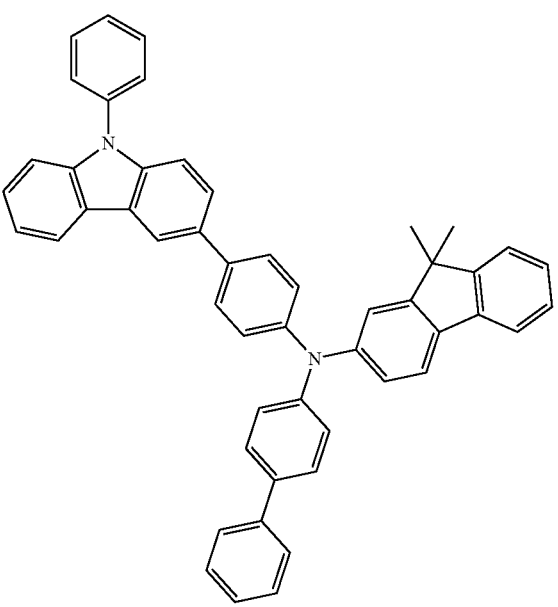

135
-continued
HT4
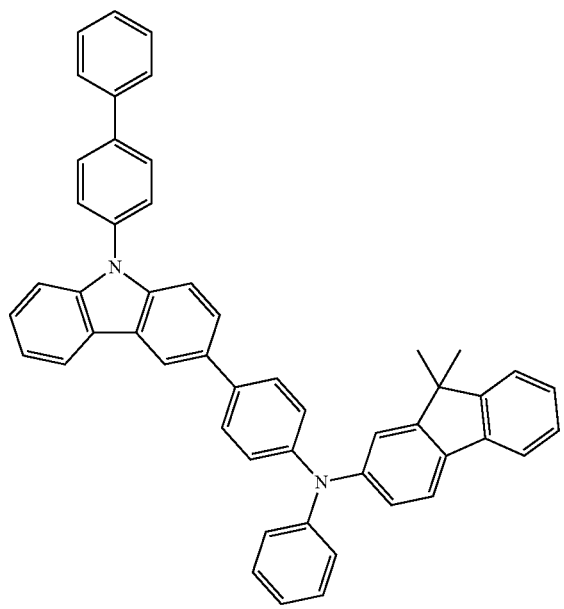
136
-continued
HT6
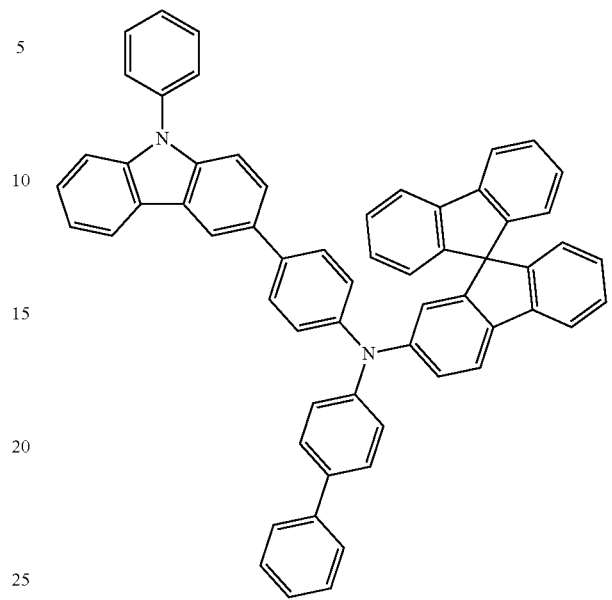
HT5
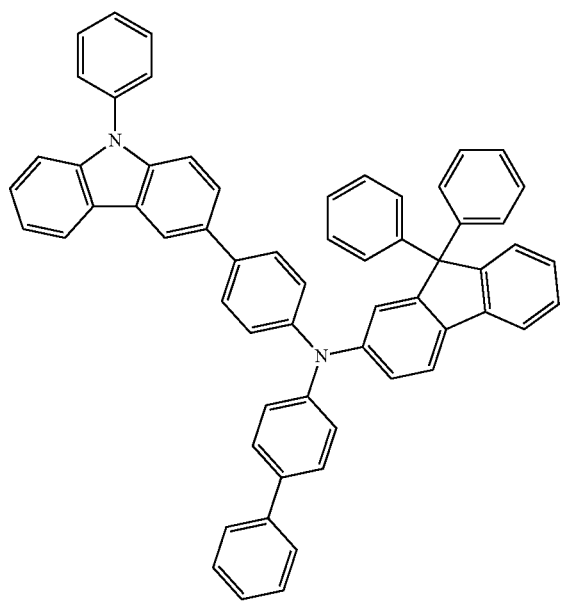
HT7
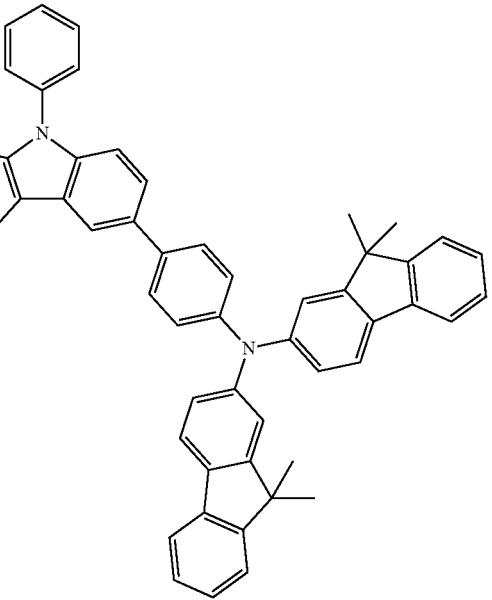

HT8
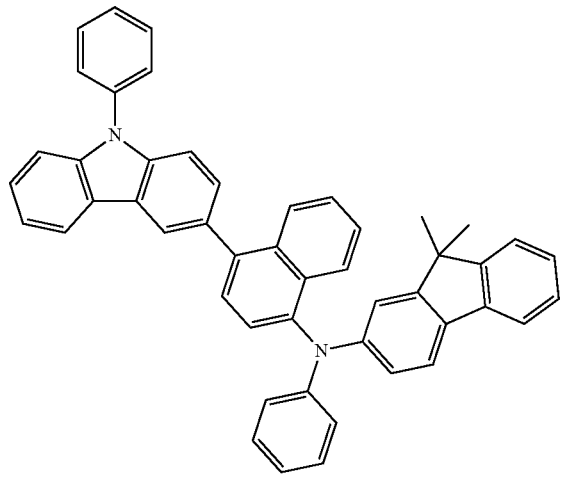
HT9
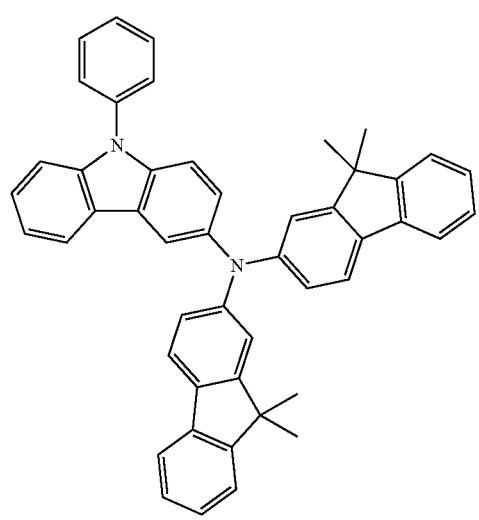
HT10
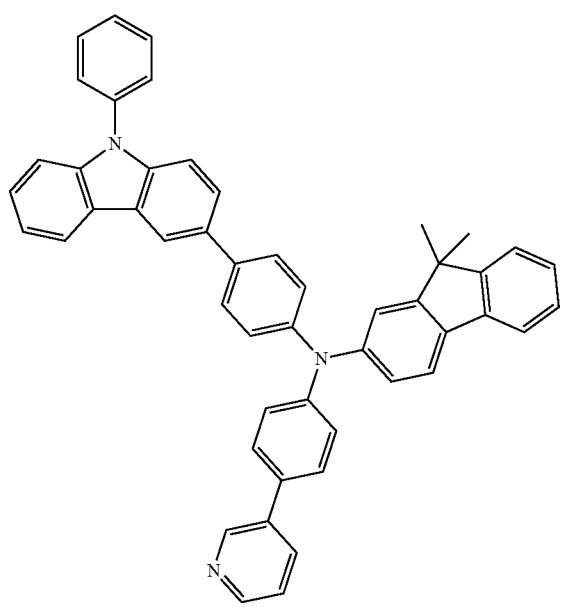
HT11
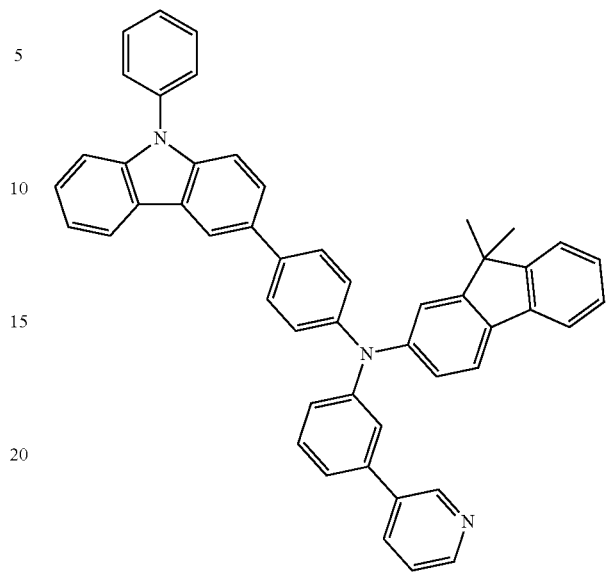
HT12
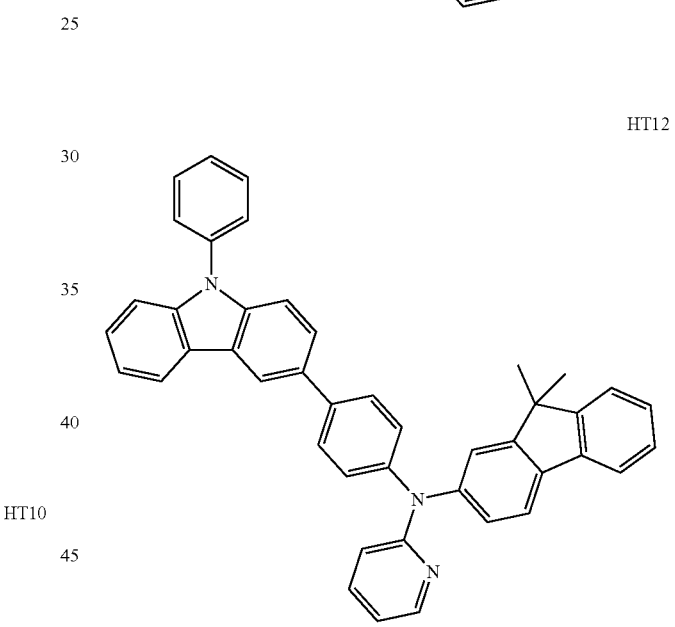
HT13
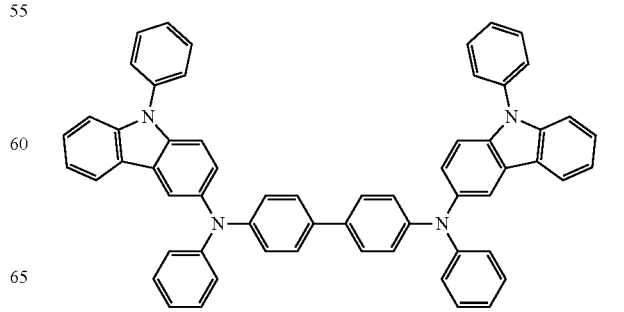

HT14

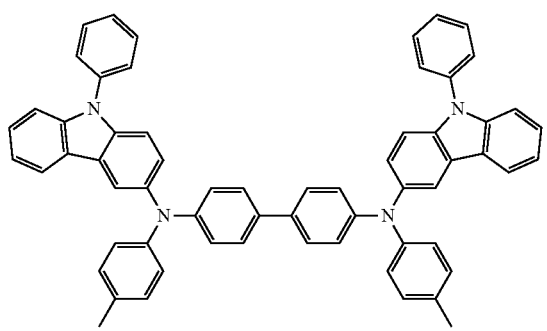

HT15

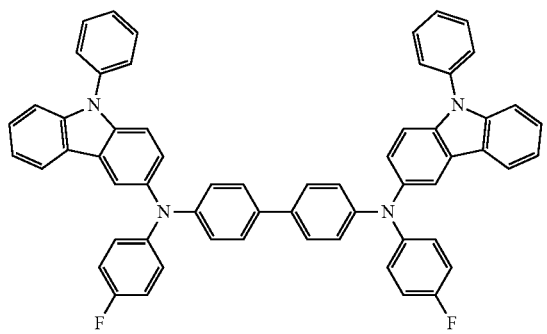

HT16

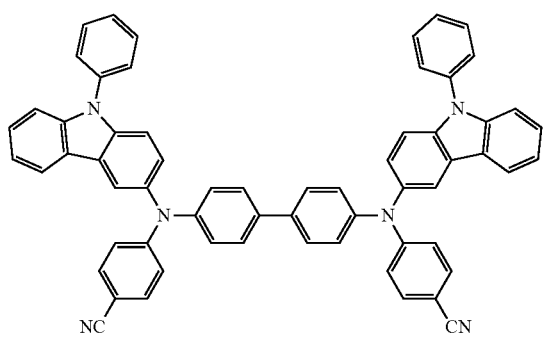

HT17

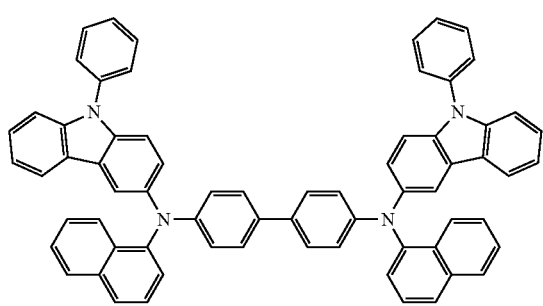

HT18

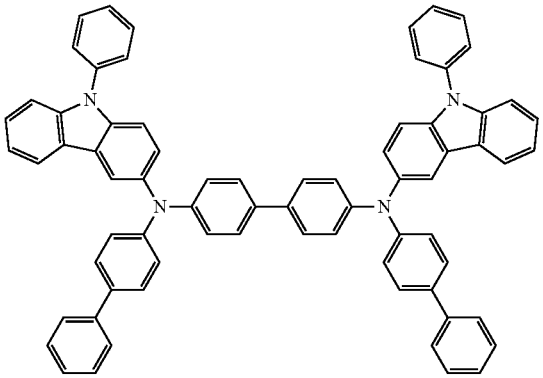

HT19

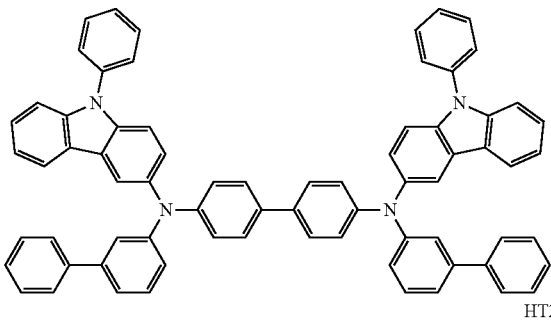

HT20

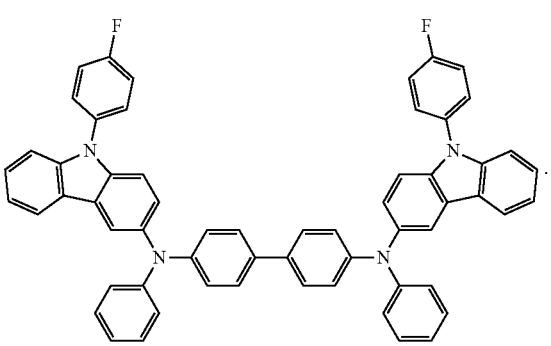

A thickness of the hole transport region may be from about 100 Å to about 10,000 Å, for example, about 100 Å to about 1,000 Å. When the hole transport region includes a hole injection layer, a hole transport layer, or any combination thereof, a thickness of the hole injection layer may be in a range of about 100 Å to about 10000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be a quinone derivative, a cyano group-containing compound, or any combination thereof, but embodiments of the present disclosure are not limited thereto. Non-limiting examples of the p-dopant are a quinone derivative, such as tetracyanoquinodimethane (TCNQ) or 2,3,5,6-tetrafluoro-tetracyano-1,4-benzoquinodimethane (F4-TCNQ); a metal oxide, such as a tungsten oxide or a molybdenum oxide; and a cyano group-containing compound, such as Compound HT-D1, but are not limited thereto:

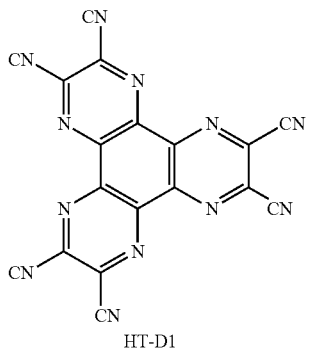

HT-D1

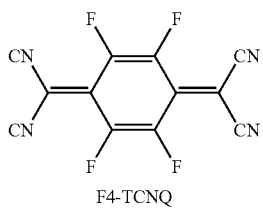

F4-TCNQ

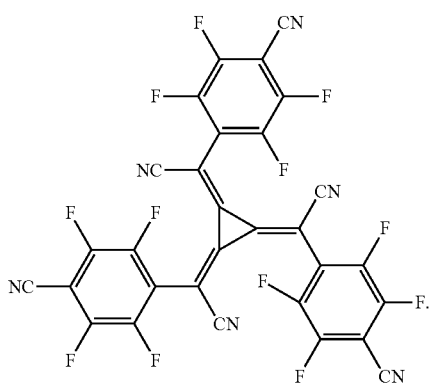

The hole transport region may further include a buffer layer.

Also, the buffer layer may compensate for an optical resonance distance according to a wavelength of light emitted from the emission layer, and thus, efficiency of a formed organic light-emitting device may be improved.

The hole transport region may further include an electron blocking layer, and the electron blocking layer may include a known material, for example, mCP. However, embodiments of the present disclosure are not limited thereto:

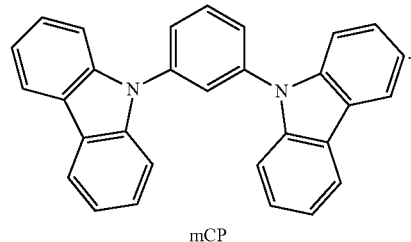

mCP

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a compound that is used to form the emission layer.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

A detailed description of the emission layer is the same as described above.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

An electron transport region may be disposed on the emission layer.

The electron transport region may include a hole blocking layer, an electron transport layer, an electron injection layer, or a combination thereof.

For example, the electron transport region may have a hole blocking layer/electron transport layer/electron injection layer structure, or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, BCP, Bphen, or a combination thereof, but embodiments of the present disclosure are not limited thereto:

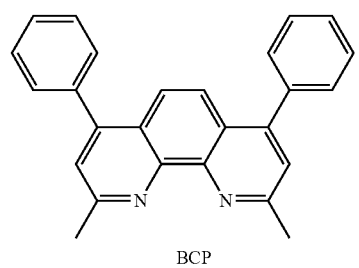

BCP

-continued

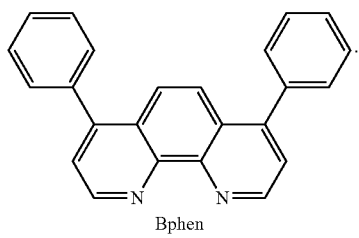

Bphen

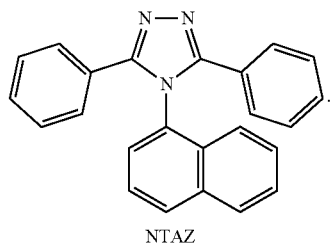

NTAZ

In one or more embodiments, the hole blocking layer may include a host. For example, the hole blocking layer may include Compound H19, but embodiments are not limited thereto.

A thickness of the hole blocking layer may be from about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include BCP, Bphe, Alq$_3$, BAlq, TAZ, NTAZ, or a combination thereof:

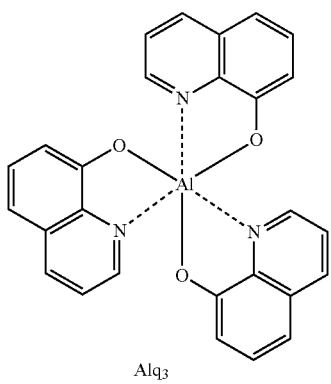

Alq$_3$

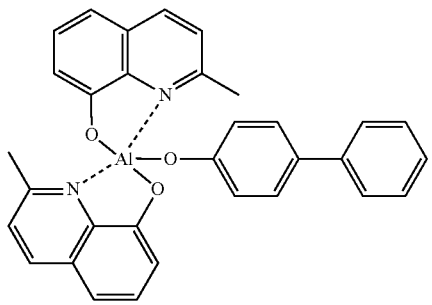

BAlq

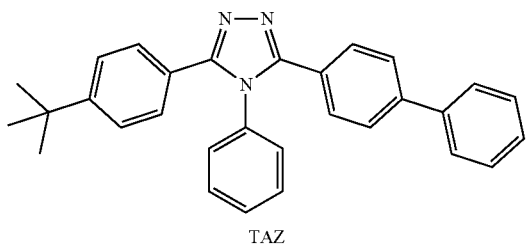

TAZ

In one or more embodiments, the electron transport layer may include Compounds ET1, ET2, ET3, or a combination thereof, but embodiments of the present disclosure are not limited thereto:

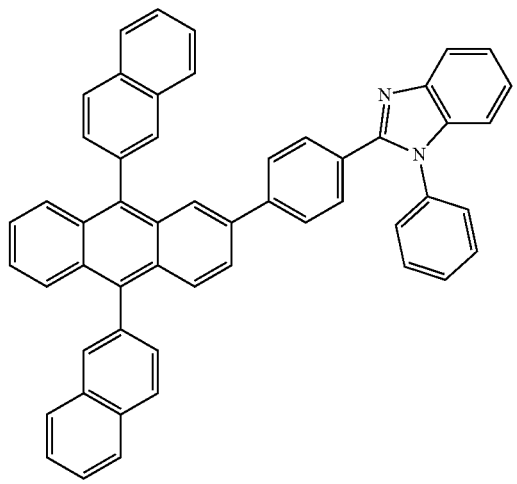

ET1

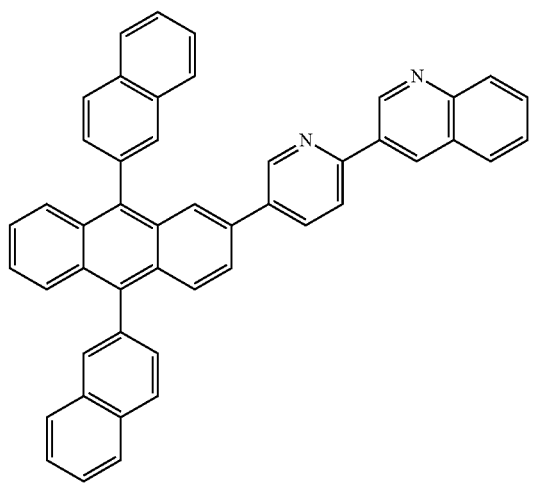

ET2

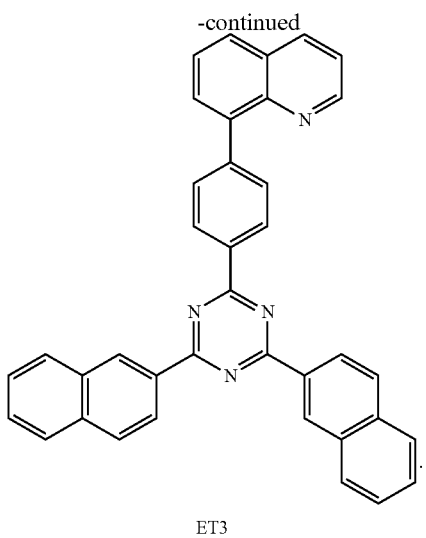

ET3

A thickness of the electron transport layer may be from about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport layer may further include, in addition to the materials described above, a metal-containing material.

The metal-containing material may include a Li complex. The Li complex may include, for example, Compound ET-D1 (lithium quinolate, LiQ) or ET-D2:

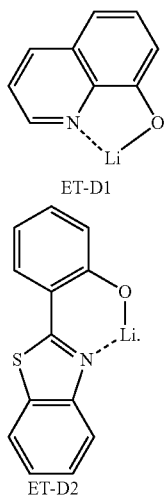

In addition, the electron transport region may include an electron injection layer that promotes flow of electrons from the second electrode 19 thereinto.

The electron injection layer may include LiF, NaCl, CsF, $Li_2O$, BaO, or a combination thereof.

A thickness of the electron injection layer may be from about 1 Å to about 100 Å, for example, about 3 Å to about 90 Å. When a thickness of the electron injection layer is within these ranges, satisfactory electron injection characteristics may be obtained without substantial increase in driving voltage.

The second electrode 19 is disposed on the organic layer 15. The second electrode 19 may be a cathode. A material for forming the second electrode 19 may be a metal, an alloy, an electrically conductive compound, or a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top-emission type light-emitting device, a transmissive electrode formed using ITO or IZO may be used as the second electrode 19.

Hereinbefore, the organic light-emitting device according to an embodiment has been described in connection with the FIGURE.

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_2$-$C_{60}$ alkenyl group" as used herein refers to a hydrocarbon group having a carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having a carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having N, O, P, Si, Se, S, or a combination thereof and 1 to 10 carbon atoms as ring-forming atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and a carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent saturated monocyclic group having N, O, P, Si, Se, S, or a combination thereof, and 1 to 10 carbon atoms as ring-forming atoms, and a double bond in the ring thereof. Non-limiting examples thereof include a 2,3-dihydrofuranyl group and a 2,3-dihydrothiophenyl group. The term "$C_1$-$C_{10}$ heterocycloalkenylene" as used herein refers to a divalent group having the same structure as the $C_1$-$C_{10}$ heterocycloalkenyl group.

The term "$C_6$-$C_{60}$ aryl group" as used herein refers to a monovalent group having a monovalent carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_2$-$C_{60}$ heteroaryl group" as used herein refers to a monovalent group having a heterocyclic aromatic system that has N, O, P, Si, Se, S, or a combination thereof, and 2 to 60 carbon atoms as ring-forming atoms. The term "$C_2$-$C_{60}$ heteroarylene group" as used herein refers to a divalent group having a heterocyclic aromatic system that has N, O, P, Si, Se, S, or a combination thereof, and 2 to 60 carbon atoms as ring-forming atoms. Non-limiting examples of the $C_2$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_2$-$C_{60}$ heteroaryl group and the $C_2$-$C_{60}$ heteroarylene group each include two or more rings, the rings may be fused to each other.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "monovalent non-aromatic condensed polycyclic group" as used herein refers to a monovalent group (for example, having 8 to 60 carbon atoms) having two or more rings condensed to each other, only carbon atoms as ring-forming atoms, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group (for example, having 2 to 60 carbon atoms) having two or more rings condensed to each other, having N, O, P, Si, Se, S, or a combination thereof, and carbon atoms as ring-forming atoms, with no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

The term "$C_5$-$C_{60}$ carbocyclic group" as used herein refers to a saturated or unsaturated cyclic group having, as a ring-forming atom, 5 to 60 carbon atoms only. The $C_5$-$C_{60}$ carbocyclic group may be a monocyclic group or a polycyclic group, and depending on the structure of formula, may be a monovalent, bivalent, trivalent, tetravalent, pentavalent, or hexavalent group.

The term "$C_2$-$C_{60}$ heterocyclic group" as used herein refers to a saturated or unsaturated cyclic group having, as ring-forming atoms, N, O, Si, P, Se, S, or a combination thereof, and 2 to 60 carbon atoms. The $C_2$-$C_{60}$ heterocyclic group may be a monocyclic group or a polycyclic group, and depending on the structure of formula, may be a monovalent, bivalent, trivalent, tetravalent, pentavalent, or hexavalent group.

The term "$C_7$-$C_{60}$ alkylaryl group" as used herein refers to an arylene group substituted with an alkyl group. A non-limiting example of a $C_7$-$C_{60}$ arylalkyl group includes a phenyl-$CH_3$ (i.e., toluyl) group.

The term "$C_2$-$C_{60}$ alkylheteroaryl group" as used herein refers to an heteroarylene group substituted with an alkyl group. A non-limiting example of a $C_2$-$C_{60}$ heteroarylalkyl group includes a pyridyl-$CH_3$ group.

The term "phenyl($C_1$-$C_{20}$ alkyl) group" as used herein refers to an alkylene group substituted with a phenyl group. Non-limiting examples of a phenyl($C_1$-$C_{20}$ alkyl) group include a —$CH_2$-phenyl (i.e., benzyl) group and a ($CH_2$)$_3$-phenyl group.

A substituent of the substituted $C_5$-$C_{60}$ carbocyclic group, the substituted $C_2$-$C_{60}$ heterocyclic group, the substituted 1T electron-depleted nitrogen-containing $C_2$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, or a $C_1$-$C_{60}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), —P(=O)($Q_{18}$)($Q_{19}$), or a combination thereof;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group, each substituted with deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N(Q$_{21}$)(Q$_{22}$), —Si(Q$_{23}$)(Q$_{24}$)(Q$_{25}$), —B(Q$_{26}$)(Q$_{27}$), —P(=O)(Q$_{28}$)(Q$_{29}$), or a combination thereof; or —N(Q$_{31}$)(Q$_{32}$), —Si(Q$_{33}$)(Q$_{34}$)(Q$_{35}$), —B(Q$_{36}$)(Q$_{37}$), or —P(=O)(Q$_{38}$)(Q$_{39}$), and $Q_1$ to $Q_9$, $Q_{11}$ to $Q_{19}$, $Q_{21}$ to $Q_{29}$, and $Q_{31}$ to $Q_{39}$ may each independently be hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryl group substituted with a $C_1$-$C_{60}$ alkyl group, a $C_6$-$C_{60}$ aryl group, or a combination thereof, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group.

The term "room temperature" as used herein refers to the temperature of about 25° C.

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of B used was identical to an amount of A used, in terms of a molar equivalent.

EXAMPLES

Synthesis Example 1: Synthesis of Compound 5

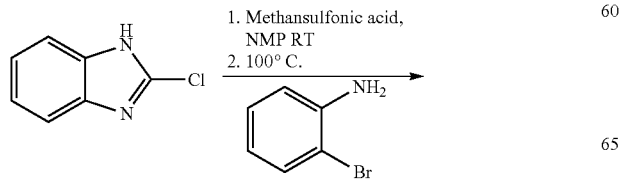

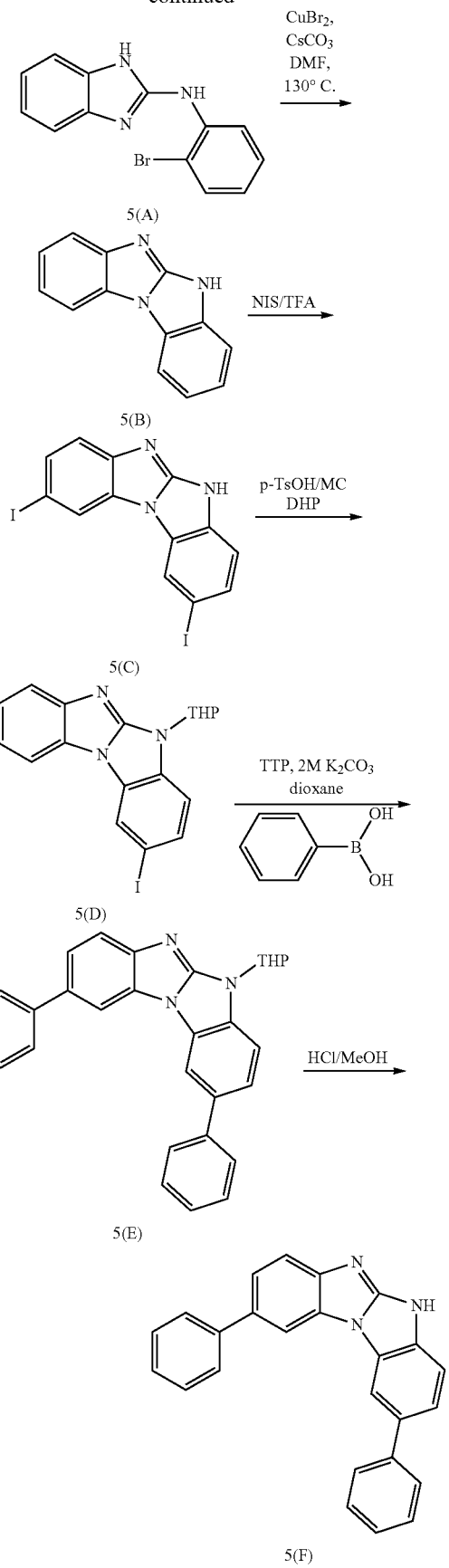

-continued

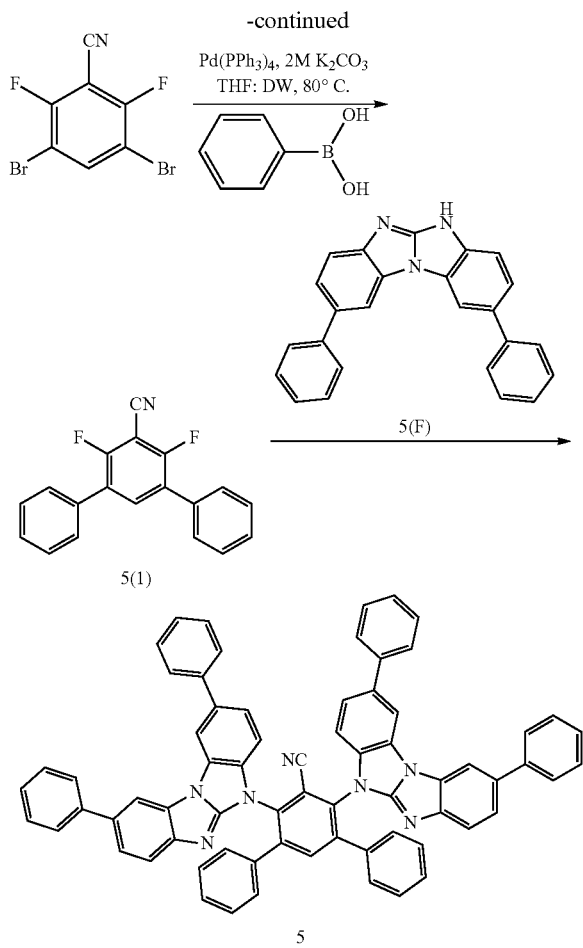

(1) Synthesis of Intermediate 5(A)

2-chloro-1H-benzo[d]imidazole (40 g, 262.16 mmol), methanesulfonic acid (0.05%, 2.78 g), and N-methyl-2-pyrrolidone (NMP) were mixed and stirred at room temperature. Next, 2-bromoaniline (54.12 g, 314.59 mmol) was added thereto, and the mixed solution was stirred at a temperature of 100° C. for 10 hours. After completion of the reaction, the reaction mixture was cooled to room temperature, and then, purified by silica gel column chromatography to obtain 70 g (yield: 93%) of Intermediate 5(A).

(2) Synthesis of Intermediate 5(B)

Intermediate 5(A) (55 g, 190.87 mmol), copper(II) bromide ($CuBr_2$) (2.13 g, 9.54 mmol), cesium carbonate ($Cs_2CO_3$) (93.29 g, 286.31 mmol), and N,N-dimethylformamide (DMF) (380 mL) were mixed and stirred at a temperature of 130° C. for 12 hours. After completion of the reaction, the reaction mixture was cooled to room temperature, and then, methanol was added thereto to obtain a solid. The obtained solid was purified by silica gel column chromatography to obtain 35 g (yield: 88%) of Intermediate 5(B) as a light yellow solid.

(3) Synthesis of Intermediate 5(C)

Intermediate 5(B) (25 g, 120.63 mmol), N-iodosuccinimide (NIS) (59.71 g, 265.39 mmol), and trifluoroacetic acid (TFA) (0.05 mol %) were added to acetonitrile (250 mL), and the mixed solution was stirred at a temperature of 100° C. for 4 hours. The reaction mixture was cooled to room temperature and the reaction was additionally carried out at room temperature for 16 hours. After completion of the reaction, the solvent was removed therefrom, and an extraction process was performed by using water and ethyl acetate. An organic layer extracted therefrom was dried by using anhydrous sodium sulfate ($Na_2SO_4$), concentrated, and then, purified by a silica gel column chromatography (dichloromethane/hexane). A solid obtained therefrom was recrystallized with hexane to obtain 45 g (yield: 81%) of Intermediate 5(C).

(4) Synthesis of Intermediate 5(D)

Intermediate 5(C) (45 g, 98.03 mmol), dihexadecyl phosphate (DHP) (107.218 g, 196.07 mmol), and p-toluenesulfonic acid monohydrate (p-TsOH) (0.466 g, 2.45 mmol) were added to dichloromethane (700 mL), and the mixed solution was stirred at room temperature for 16 hours. After completion of the reaction, an organic layer was separated by using water, and the organic layer was dried by using anhydrous sodium sulfate ($Na_2SO_4$), concentrated, and then, purified by silica gel column chromatography. A solid obtained therefrom was recrystallized with hexane to obtain 41 g (yield: 77%) of Intermediate 5(D).

(5) Synthesis of Intermediate 5(E)

Intermediate 5(D) (40 g, 73.64 mmol), phenylboronic acid (19.75 g, 162.02 mmol), palladium tetrakis(triphenylphosphine) ($Pd(PPh_3)_4$, also abbreviated as TTP) (4.26 g, 3.68 mmol), and potassium carbonate ($K_2CO_3$) (22.39 g, 162.02 mmol) were added to dioxane (150 mL) and distilled water (150 mL), and the mixed solution was heated under reflux. After completion of the reaction, the reaction mixture was cooled to room temperature, and methanol was added thereto. The resulting mixture was filtered through silica gel, and an organic layer obtained therefrom was concentrated. Methanol was added thereto to perform a precipitation process, thereby obtaining 30.65 g (yield: 93%) of Intermediate 5(E) as a white solid.

(6) Synthesis of Intermediate 5(F)

Intermediate 5(E) (30 g, 67.64 mmol) was added to a 500 mL flask containing hydrogen chloride/methanol (2% HCl/MeOH), and the mixed solution was stirred for one day. After completion of the reaction, an extraction process was performed thereon by using dichloromethane. An organic layer extracted therefrom was dried by using anhydrous sodium sulfate ($Na_2SO_4$), concentrated, and purified by silica gel column chromatography (ethyl acetate/hexane) to obtain 17.56 g (yield: 72%) of Intermediate 5(F).

(7) Synthesis of Intermediate 5(1)

Phenylboronic acid (40.66 g, 333.45 mmol), 3,5-dibromo-2,6-difluorobenzonitrile (45 g, 151.57 mmol), palladium tetrakis(triphenylphosphine) ($Pd(PPh_3)_4$) (17.52 g, 15.16 mmol), potassium carbonate ($K_2CO_3$) (92.17 g, 666.89 mmol), and S-phos (24.89 g, 60.63 mmol) were added to tetrahydrofuran (300 mL) and distilled water (150 mL), and the mixed solution was heated under reflux. After completion of the reaction, the reaction mixture was cooled at room temperature, and an extraction process was performed thereon by using ethyl acetate. An organic layer extracted therefrom was dried by using anhydrous sodium sulfate ($Na_2SO_4$), concentrated, and purified by silica gel column chromatography (dichloromethane/hexane). A solid obtained therefrom was recrystallized with hexane to obtain 36.7 g (yield: 83%) of Intermediate 5(1) as a while solid.

(8) Synthesis of Compound 5

Intermediate 5(1) (2.5 g, 8.58 mmol), Intermediate 5(F) (6.79 g, 18.88 mmol), and cesium carbonate ($Cs_2CO_3$) (12.304 g, 37.76 mmol) were added to DMF (22 mL), and the mixed solution was stirred at a temperature of 165° C. for 20 hours. After completion of the reaction, the reaction mixture was cooled to room temperature, and methanol was added thereto. The resulting mixture was filtered through silica gel, and an organic layer obtained therefrom was concentrated. The resulting organic layer was dissolved in toluene, and then, filtered through silica gel, and an organic layer obtained therefrom was concentrated. A solid obtained therefrom was recrystallized (ethyl acetate/ethanol) to obtain 4.2 g (yield: 50%) of Compound 5 as a yellow solid.

LC-Mass (calculated: 970.15 g/mol, found: 971.15 g/mol (M+1))

Evaluation Example 1

According to the methods shown in Table 2, the emission spectrum, HOMO, LUMO, singlet ($S_1$) energy level, triplet ($T_1$) energy level, and $\Delta E_{ST}$ of Compound 5, Compound A, and Compound B were evaluated. The results are shown in Table 3.

TABLE 2

| | |
|---|---|
| Photoluminescence (PL) spectrum | Each compound was diluted in toluene at the concentration of $10^{-5}$M, and the PL spectrum was measured (at 298K) by using the Xenon lamp-equipped Hitachi Model No. F7000 Spectrofluorometer |
| $S_1$ energy level evaluation method | The PL spectrum of a mixture of toluene and each compound (diluted to a concentration of $1 \times 10^{-4}$M) was measured at room temperature by using a PL spectrometer and identified peaks were analyzed to calculate on-set $S_1$ energy level |
| $T_1$ energy level evaluation method | A mixture of toluene and each compound (diluted to a concentration of $1 \times 10^{-4}$M) was placed in a quartz cell and placed in liquid nitrogen (77 K). The PL spectrum thereof was measured, and the PL spectrum at 77K was compared with a PL spectrum measured at room temperature to identify peaks that appeared only at room temperature to calculate on-set $T_1$ energy level |
| $\Delta E_{ST}$ | Difference between $S_1$ energy level and $T_1$ energy level was calculated |

TABLE 3

| Compound No. | HOMO (eV) | LUMO (eV) | $S_1$ energy level (eV) | $T_1$ energy level (eV) | $\Delta E_{ST}$ (eV) | Maximum emission wavelength (nm) of PL spectrum |
|---|---|---|---|---|---|---|
| 5 | −5.273 | −1.954 | 2.744 | 2.733 | 0.011 | 457 |
| A | −5.346 | −2.087 | 2.773 | 2.701 | 0.072 | 467 |
| B | −5.403 | −2.041 | 2.768 | 2.675 | 0.093 | 459 |

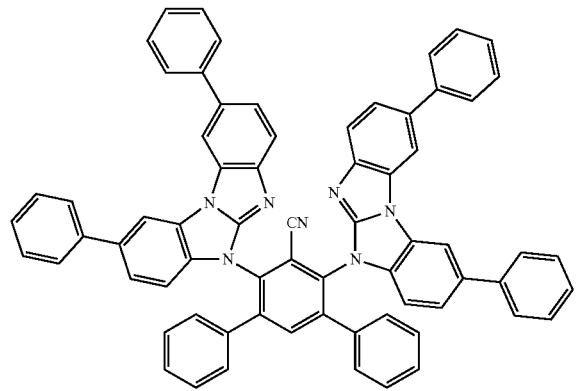

5

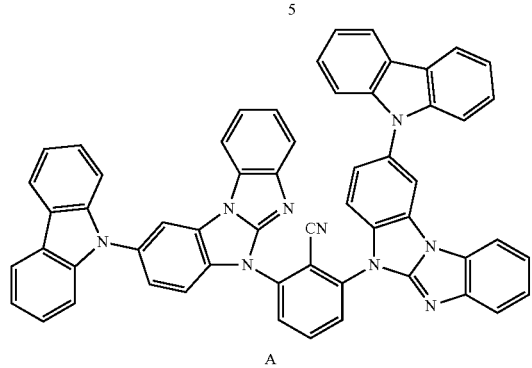

A

TABLE 3-continued

| Compound No. | HOMO (eV) | LUMO (eV) | $S_1$ energy level (eV) | $T_1$ energy level (eV) | $\Delta E_{ST}$ (eV) | Maximum emission wavelength (nm) of PL spectrum |
|---|---|---|---|---|---|---|

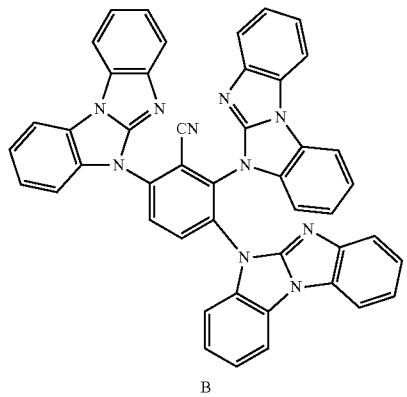

B

From Table 3, it can be seen that Compound 5 can emit deep blue light, have a small $\Delta E_{ST}$, and emit thermal activation delayed fluorescence light at the same time.

Evaluation Example 2

Compound H19 and Compound 5 (15% by weight) were co-deposited on a quartz cell to prepare Film 5 having a thickness of 100 Å. Films were fabricated in the same manner as described above by using the compounds shown in Table 4 respectively instead of Compound 5. Then, Film 5, Film A, and Film B were excited with excitation light having a wavelength of 340 nm under a nitrogen atmosphere by using C9920-02 and PMA-11 of Hamamatsu photonics to measure luminous efficiency (PL yield) of each film, and the results are shown in Table 4.

TABLE 4

| Film No. | Film component | Luminous quantum efficiency (%) |
|---|---|---|
| 5 | Compound 5 + H19 | 0.646 |
| A | Compound A + H19 | 0.589 |
| B | Compound B + H19 | 0.432 |

From Table 4, it can be seen that Film 5 has higher luminous quantum efficiency than Films A and B.

Example 1

A glass substrate, on which a 1,500 Å-thick indium tin oxide (ITO) electrode (first electrode, anode) was formed, was cleaned by distilled water ultrasonication. After the distilled water ultrasonication was completed, ultrasonic cleaning was performed sequentially with isopropyl alcohol, acetone, and methanol, one for each, and the glass substrate was dried and transferred to a plasma cleaner. The glass substrate was cleaned by using oxygen plasma for 5 minutes, and then transferred to a vacuum laminator.

Compound HT3 was vacuum-deposited on the ITO electrode on the glass substrate to form a first hole injection layer having a thickness of 100 Å, Compound HT-D1 was vacuum-deposited on the first hole injection layer to form a second hole injection layer having a thickness of 100 Å, and mCP was vacuum-deposited on the second hole injection layer to form an electron blocking layer having a thickness of 150 Å, thereby completing the formation of a hole transport region.

Compound H19 (host) and Compound 5(dopant) were co-deposited on the hole transport region at a volumetric ratio of 85:15 to form an emission layer having a thickness of 300 Å.

Compound ET3 was vacuum-deposited on the emission layer to form an electron transport layer having a thickness of 300 Å, and then, ET-D1(LiQ) was deposited on the electron transport layer to form an electron injection layer having a thickness of 10 Å, and an Al second electrode (cathode) having a thickness of 1,200 Å was formed on the electron injection layer, thereby completing the manufacture of an organic light-emitting device:

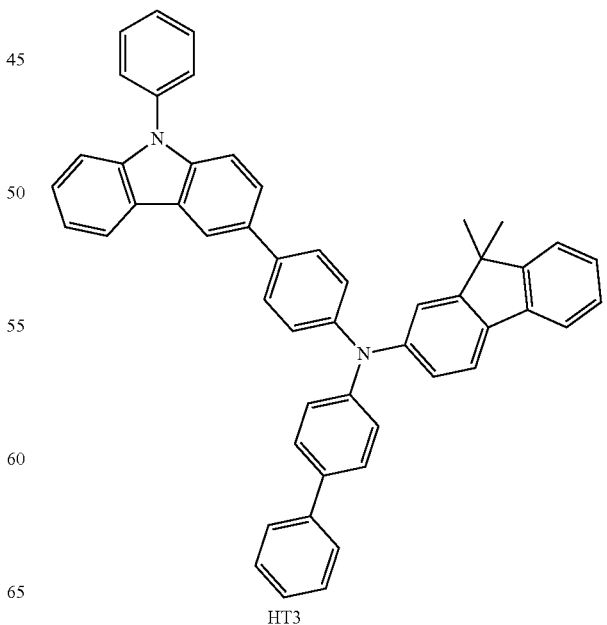

HT3

-continued

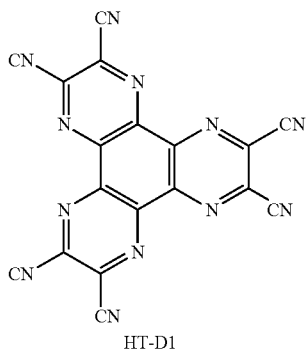

HT-D1

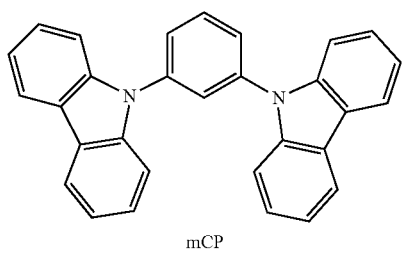

mCP

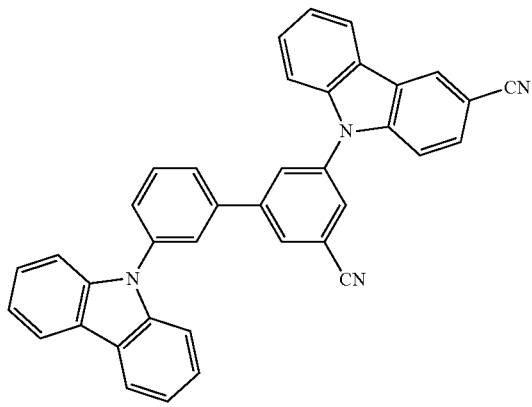

H19

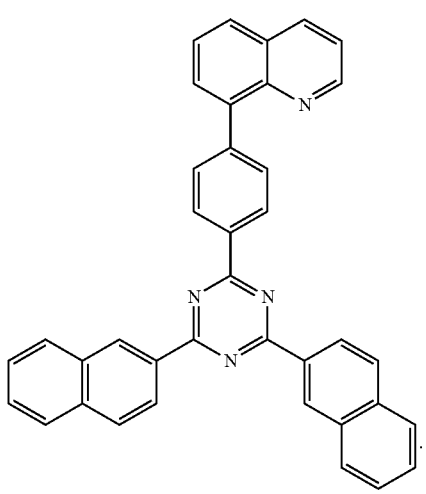

ET3

Comparative Examples A and B

Organic light-emitting devices were manufactured in the same manner as in Example 1, except that in forming an emission layer, for use as a dopant, corresponding compounds shown in Table 5 were used instead of Compound 5.

Evaluation Example 3

The driving voltage, external quantum efficiency, and lifespan of the organic light-emitting devices manufactured according to Example 1 and Comparative Examples A and B were measured by using a current-voltage meter (Keithley 2400) and a luminance meter (Minolta Cs-1000A) at 500 cd/m². Results thereof are shown in Table 5. In Table 5, the lifespan data ($T_{95}$) (at 500 cd/m²) (relative values) indicate an amount of time that lapsed when luminance was 95% of initial luminance (100%) under the same conditions, and were expressed with a relative value.

TABLE 5

| Example No. | Host | Dopant | External quantum efficiency (relative value (%)) | Maximum emission wavelength | $LT_{95}$ at 500 cd/m² (relative value (%)) |
|---|---|---|---|---|---|
| Example 1 | Compound H19 | Compound 5 | 208 | 456 | 100 |
| Comparative Example A | Compound H19 | Compound A | 150 | 465 | 21.7 |
| Comparative Example B | Compound H19 | Compound B | 100 | 460 | 34.2 |

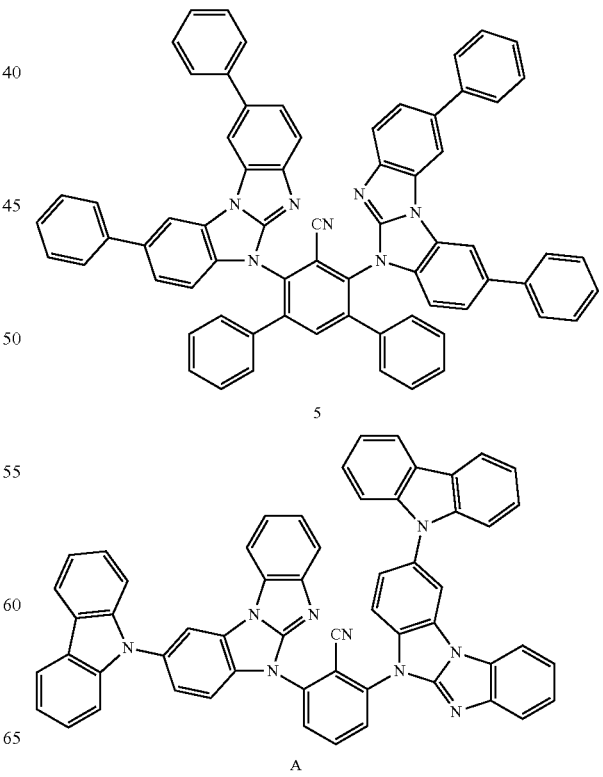

5

A

TABLE 5-continued

| Example No. | Host | Dopant | External quantum efficiency (relative value (%)) | Maximum emission wavelength | LT$_{95}$ at 500 cd/m$^2$ (relative value (%)) |
|---|---|---|---|---|---|

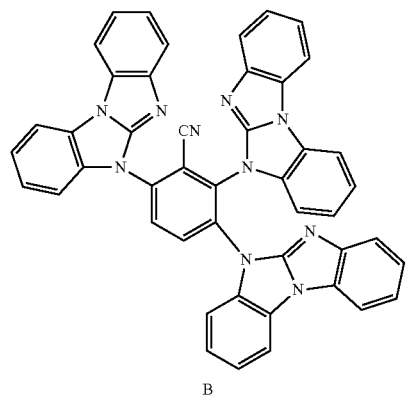

B

From Table 5, it can be seen that the organic light-emitting device of Example 1 has better driving voltage, external quantum efficiency, and/or lifespan characteristics than the organic light-emitting devices of Comparative Examples A to C.

According to the one or more embodiments, the condensed-cyclic compound has excellent delayed fluorescent emission characteristics, and an organic light-emitting device employing the condensed-cyclic compound may have high efficiency and/or long lifespan.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope as defined by the following claims.

What is claimed is:

1. A condensed-cyclic compound represented by any of Formulae 1-1 to 1-58,

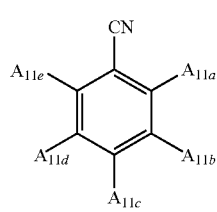

1-1

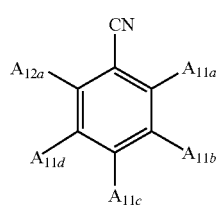

1-2

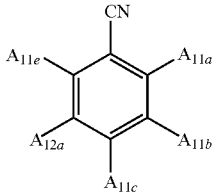

1-3

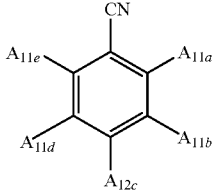

1-4

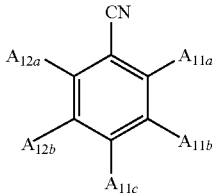

1-5

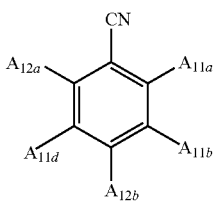

1-6

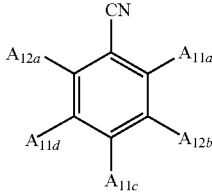

1-7

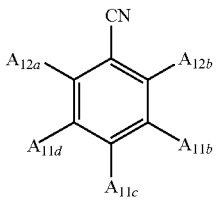

1-8

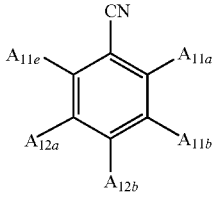

1-9

-continued
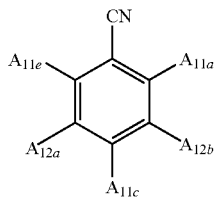
1-10
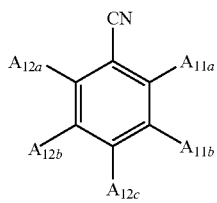
1-11
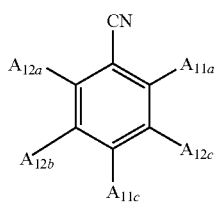
1-12
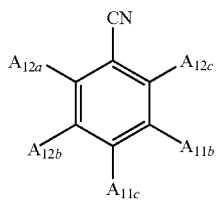
1-13
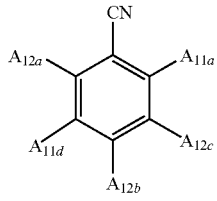
1-14
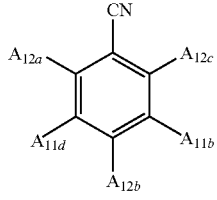
1-15
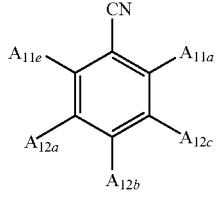
1-16
-continued
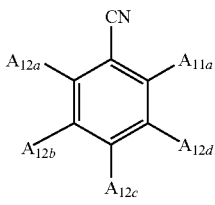
1-17
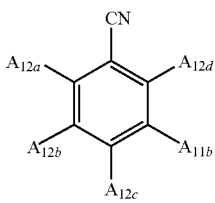
1-18
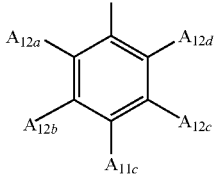
1-19
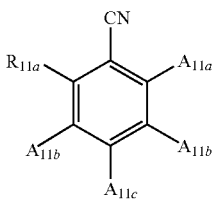
1-20
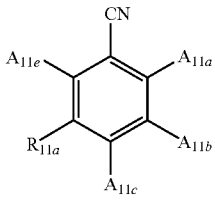
1-21
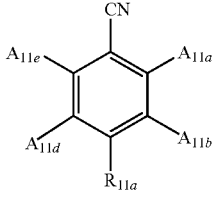
1-22
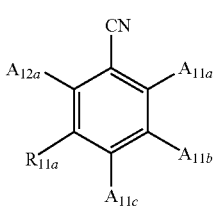
1-23

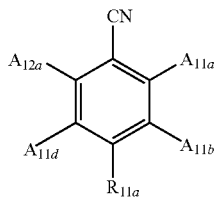
1-24
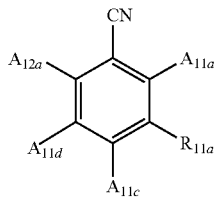
1-25
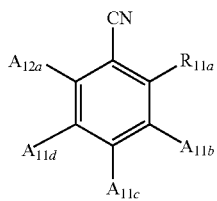
1-26
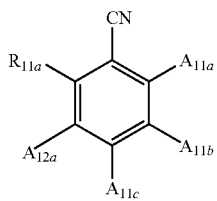
1-27
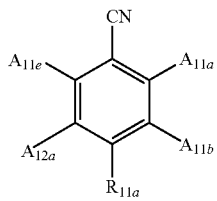
1-28
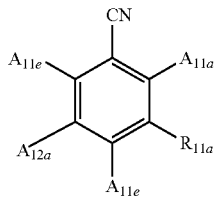
1-29
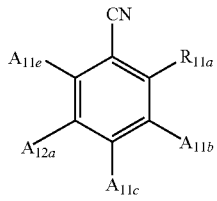
1-30
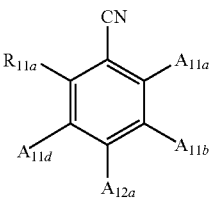
1-31
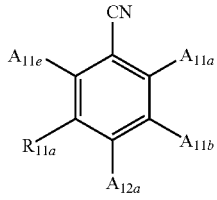
1-32
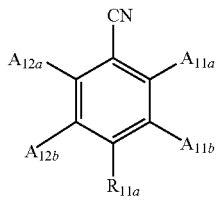
1-33
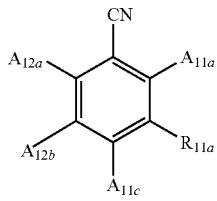
1-34
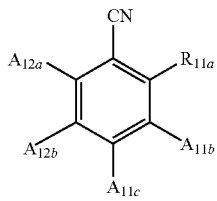
1-35
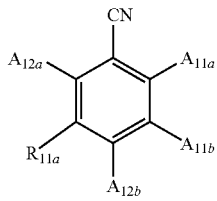
1-36
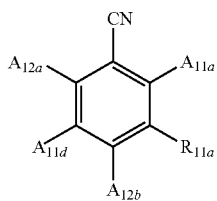
1-37

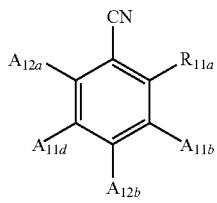 1-38
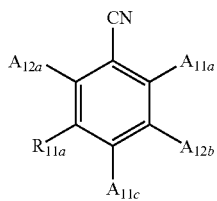 1-39
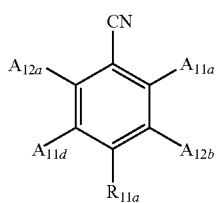 1-40
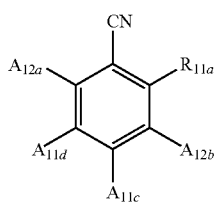 1-41
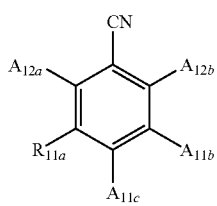 1-42
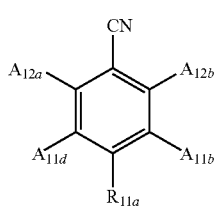 1-43
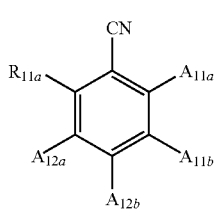 1-44
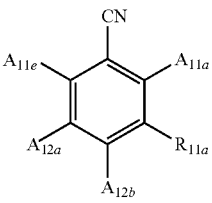 1-45
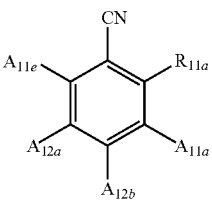 1-46
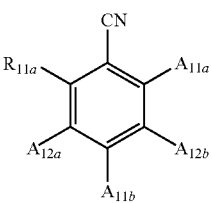 1-47
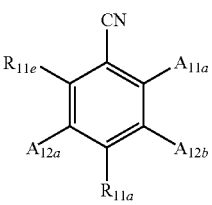 1-48
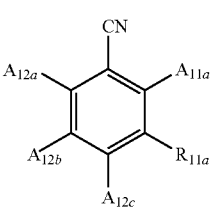 1-49
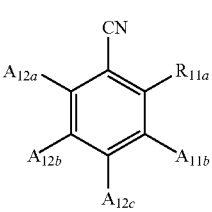 1-50
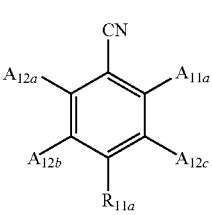 1-51

-continued 1-52 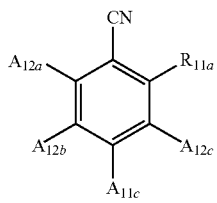

1-53 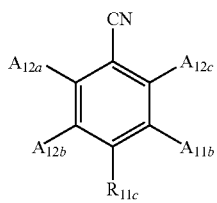

1-54 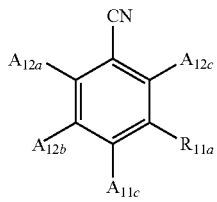

1-55 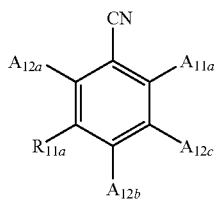

1-56 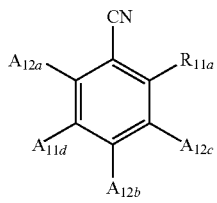

1-57 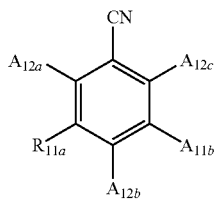

1-58 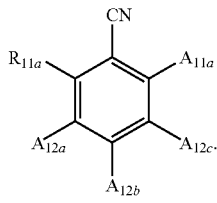

wherein, in Formulae 1-1 to 1-58,
$A_{11a}$ to $A_{11d}$ are each independently represented by any of Formulae 2-1 to 2-3;

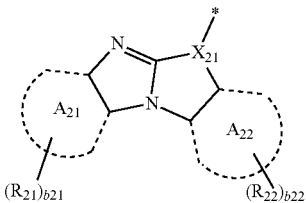

Formula 2-1

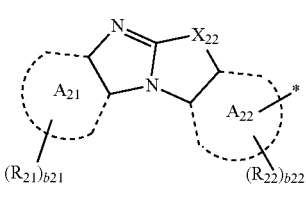

Formula 2-2

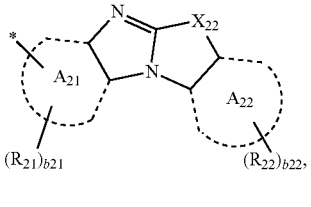

Formula 2-3 wherein, in Formulae 2-1 to 2-3,
$X_{21}$ is N or $C(R_{23})$;
$X_{22}$ is $N(R_{24})$, $C(R_{24})(R_{25})$, O, or S;
ring $A_{21}$ and ring $A_{22}$ are each independently a $C_5$-$C_{60}$ carbocyclic group or a $C_1$-$C_{60}$ heterocyclic group;
$R_{21}$ to $R_{25}$ are each independently hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_2$-$C_{60}$ alkylheteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si$(Q_1)(Q_2)(Q_3)$, —B$(Q_1)(Q_2)$, —N$(Q_1)(Q_2)$, —P$(Q_1)(Q_2)$, —C(=O)$(Q_1)$, —S(=O)$(Q_1)$, —S(=O)$_2(Q_1)$, —P(=O)$(Q_1)(Q_2)$, or —P(=S)$(Q_1)(Q_2)$,
b21 and b22 may each independently be 1, 2, 3, 4, 5, 6, 7, 8, 9, or 10;
* indicates a binding site to a neighboring atom;
$A_{12a}$ to $A_{12d}$ are each independently a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_7$-$C_{60}$ alkylaryl group, a substituted or unsubstituted $C_1$-$C_{60}$ heteroaryl group, a substituted or unsubstituted $C_2$-$C_{60}$ alkylheteroaryl group, a substituted or unsubstituted monovalent non-aromatic condensed polycyclic group, or a substituted or unsubstituted monovalent non-aromatic condensed heteropolycyclic group;

$R_{11a}$ is hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, —Si$(Q_1)(Q_2)(Q_3)$, —B$(Q_1)(Q_2)$, —N$(Q_1)(Q_2)$, —P$(Q_1)(Q_2)$, —C$(=O)(Q_1)$, —S$(=O)(Q_1)$, —S$(=O)_2$ $(Q_1)$, —P$(=O)(Q_1)(Q_2)$, or —P$(=S)(Q_1)$ $(Q_2)$, $Q_1$ to $Q_3$ are each independently hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_7$-$C_{60}$ alkylaryl group, a $C_6$-$C_{60}$ aryloxy group, a $C_6$-$C_{60}$ arylthio group, a $C_1$-$C_{60}$ heteroaryl group, a $C_2$-$C_{60}$ alkylheteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a $C_1$-$C_{60}$ alkyl group substituted with deuterium, —F, a cyano group, a $C_1$-$C_{60}$ alkyl group, a $C_6$-$C_{60}$ aryl group, or a combination thereof, or a $C_6$-$C_{60}$ aryl group substituted with deuterium, —F, a cyano group, a $C_1$-$C_{60}$ alkyl group, a $C_6$-$C_{60}$ aryl group, or a combination thereof.

2. The condensed-cyclic compound of claim 1, wherein $X_{21}$ is N; and
$X_{22}$ is N$(R_{24})$, O, or S.

3. The condensed-cyclic compound of claim 1, wherein ring $A_{21}$ and ring $A_{22}$ are each independently a benzene group, a naphthalene group, an anthracene group, a phenanthrene group, a phenalene group, a triphenylene group, a pyridine group, a pyrimidine group, a pyrazine group, a pyridazine group, a triazine group, a quinoline group, an isoquinoline group, a 2,6-naphthyridine group, a 1,8-naphthyridine group, a 1,5-naphthyridine group, a 1,6-naphthyridine group, a 1,7-naphthyridine group, a 2,7-naphthyridine group, a quinoxaline group, a phthalazine group, a quinazoline group, a phenanthroline group, a benzoquinoline group, a benzoisoquinoline group, a benzoquinoxaline group, a benzoquinazoline group, a furan group, a thiophene group, a silole group, an indene group, a fluorene group, an indole group, a carbazole group, a benzofuran group, a dibenzofuran group, a benzothiophene group, a dibenzothiophene group, a benzosilole group, a dibenzosilole group, an indenopyridine group, an indolopyridine group, a benzofuropyridine group, a benzothienopyridine group, a benzosilolopyridine group, an indenopyrimidine group, an indolopyrimidine group, a benzofuropyrimidine group, a benzothienopyrimidine group, or a benzosilolopyrimidine group.

4. The condensed-cyclic compound of claim 1, wherein $A_{11}$ is a group represented by any of Formulae 2-11 to 2-13:

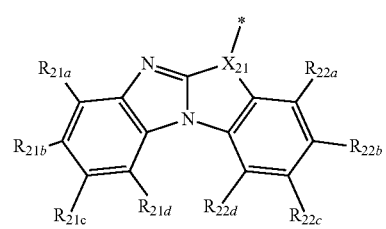

2-11

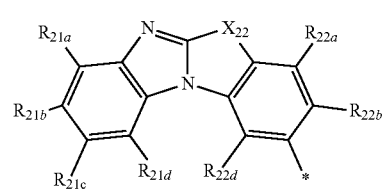

2-12

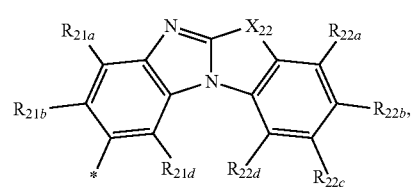

2-13 wherein, in Formulae 2-11 to 2-13, $X_{21}$ and $X_{22}$ are each the same as defined in connection with Formulae 2-1 to 2-3 in claim 1, $R_{21a}$ to $R_{21d}$ are each the same as defined in connection with $R_{21}$ in Formula 2-1 in claim 1, $R_{22a}$ to $R_{22d}$ are each the same as defined in connection with $R_{22}$ Formula 2-1 in claim 1, and

* indicates a binding site to a neighboring atom.

5. The condensed-cyclic compound of claim 1, wherein $A_{12}$ is:

a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group; or a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each substituted with deuterium, —F, —Cl, —Br, —I, —$CD_3$, —$CD_2H$, —$CDH_2$, —$CF_3$, —$CF_2H$, —$CFH_2$, a hydroxyl group, a nitro group, a cyano group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyridinyl group substituted with a phenyl group, a pyrazinyl group, a pyrazinyl group substituted with a phenyl group a pyrimidinyl group, a pyrimidinyl group substituted with a phenyl group, a pyridazinyl group, a pyridazinyl group substituted with a phenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a triazinyl group substituted with a phenyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si($Q_{11}$)($Q_{12}$)($Q_{13}$), —B($Q_{11}$)($Q_{12}$), —N($Q_{11}$)($Q_{12}$), or a combination thereof, and $Q_{11}$ to $Q_{13}$ are each independently:

a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a phenyl($C_1$-$C_{20}$ alkyl) group, or a naphthyl group; or a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group substituted with deuterium, a phenyl group, or a combination thereof.

6. The condensed-cyclic compound of claim 1, wherein $R_{11a}$ is:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, or a $C_1$-$C_{20}$ alkoxy group;

a $C_1$-$C_{20}$ alkyl group or a $C_1$-$C_{20}$ alkoxy group, each substituted with deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a pyridinyl group, a pyrimidinyl group, or a combination thereof;

a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group;

a cyclopentyl group, a cyclohexyl group, a cycloheptyl group, a cycloctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a benzocarbazolyl group, a dibenzocarbazolyl group, an imidazopyridinyl group, or an imidazopyrimidinyl group, each substituted with deuterium, —F, —Cl, —Br, —I, —$CD_3$, —$CD_2H$, —$CDH_2$, —$CF_3$, —$CF_2H$, —$CFH_2$, a hydroxyl group, a nitro group, a cyano group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a cyclopentyl group, a cyclohexyl group, a cycloheptyl group, a cyclooctyl group, an adamantyl group, a norbornyl group, a norbornenyl group, a cyclopentenyl group, a cyclohexenyl group, a cycloheptenyl group, a phenyl group, a biphenyl group, a phenyl($C_1$-$C_{20}$ alkyl) group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyridinyl group substituted with a phenyl group, a pyrazinyl group, a pyrazinyl group substituted with a phenyl group a pyrimidinyl group, a pyrimidinyl group substituted with a phenyl group, a pyridazinyl group, a pyridazinyl group substituted with a phenyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a triazinyl group substituted with a phenyl group, a dibenzofuranyl group, a dibenzothiophenyl group, a dibenzosilolyl group, a benzocarbazolyl group, a dibenzocarbazolyl group, an imidazopyridinyl group, an imidazopyrimidinyl group, —Si($Q_{11}$)($Q_{12}$)($Q_{13}$), —B($Q_{11}$)($Q_{12}$), —N($Q_{11}$)($Q_{12}$), or a combination thereof; or —Si($Q_1$)($Q_2$)($Q_3$), —B($Q_1$)($Q_2$), or —N($Q_1$)($Q_2$), and $Q_1$ to $Q_3$ and $Q_{11}$ to $Q_{13}$ are each independently:

a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, a biphenyl group, a phenyl($C_1$-$C_{20}$ alkyl) group, or a naphthyl group; or a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a sec-pentyl group, a tert-pentyl group, a neo-pentyl group, a 3-pentyl group, a 3-methyl-2-butyl group, a phenyl group, or a naphthyl group substituted with deuterium, a phenyl group, or a combination thereof.

7. The condensed-cyclic compound of claim 1, wherein $R_{11a}$ is hydrogen, deuterium, —F, —Cl, —Br, —I, or a cyano group.

8. The condensed-cyclic compound of claim 1, wherein the condensed-cyclic compound is represented by any of Formulae 1-1 to 1-19, 1-21 to 1-25, 1-28, 1-29, 1-32 to 1-34, 1-36, 1-37, 1-39, 1-40, 1-42, 1-43, 1-45, 1-48, 1-49, 1-51, 1-53 to 1-55, or 1-57.

9. The condensed-cyclic compound of claim 1, wherein the condensed-cyclic compound is any of Compounds 1 to 39:

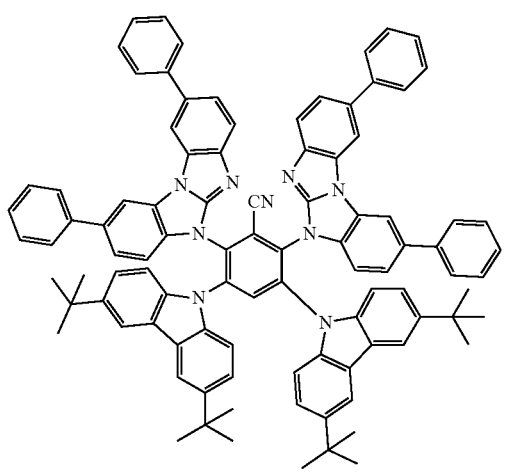

1

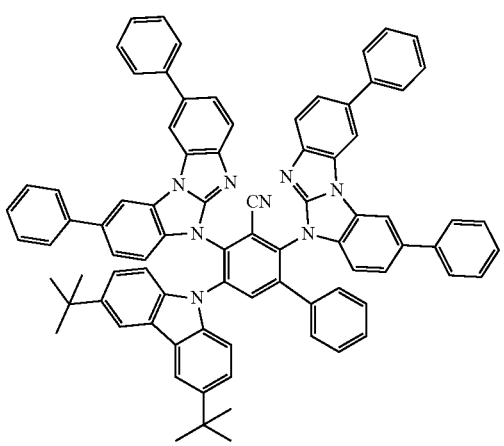

2

-continued
3
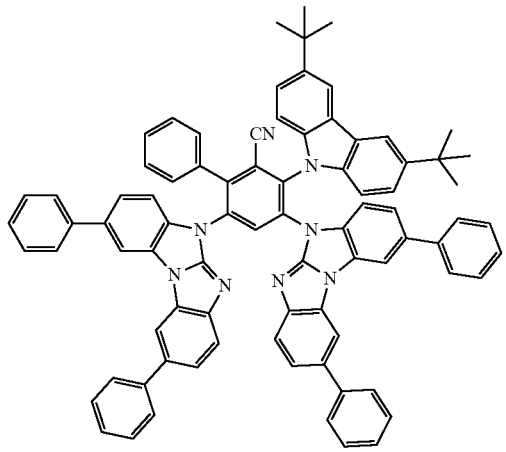
4
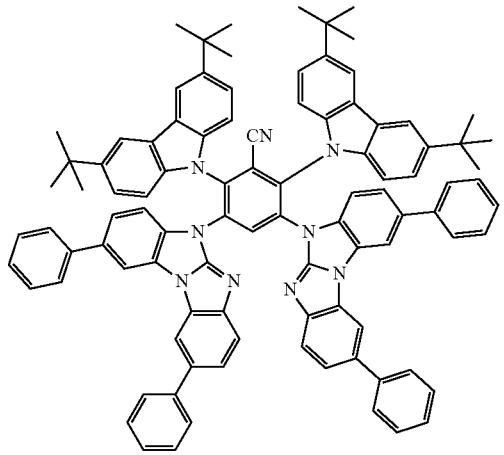
5
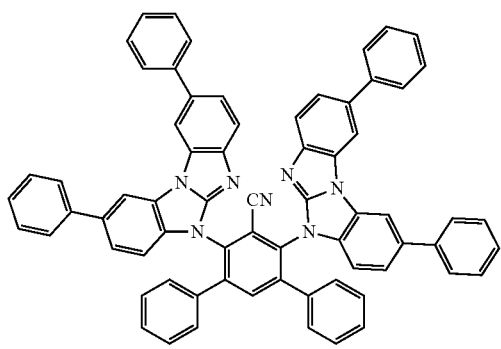
6
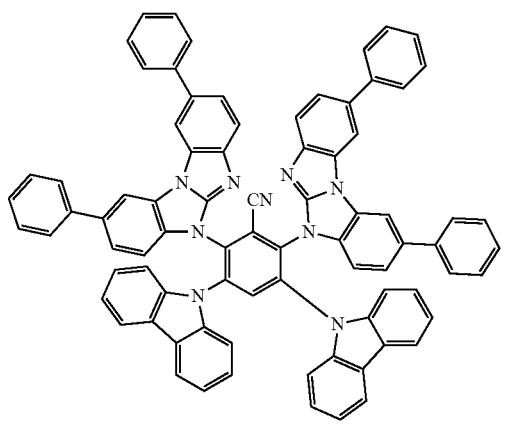
7
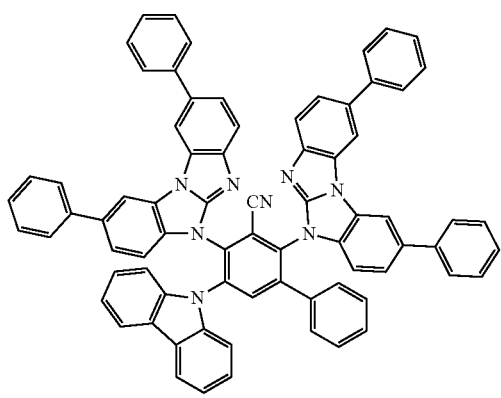
8
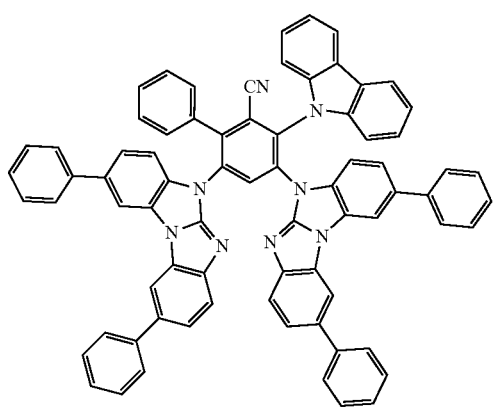

-continued
177
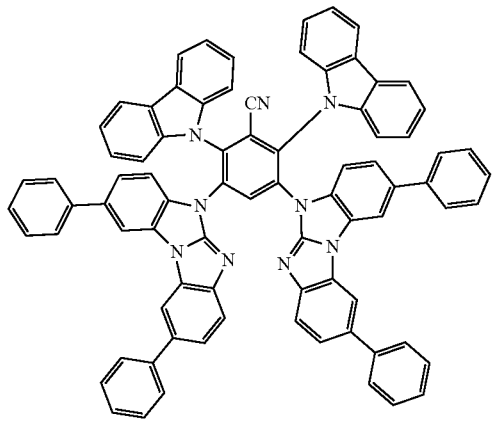
9
178
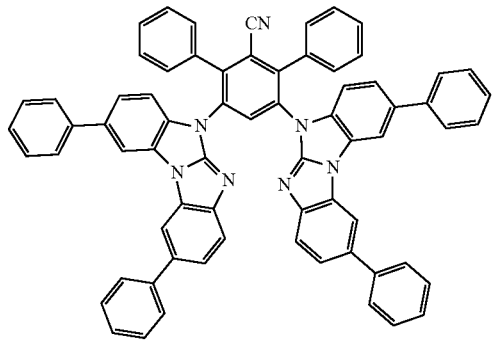
10
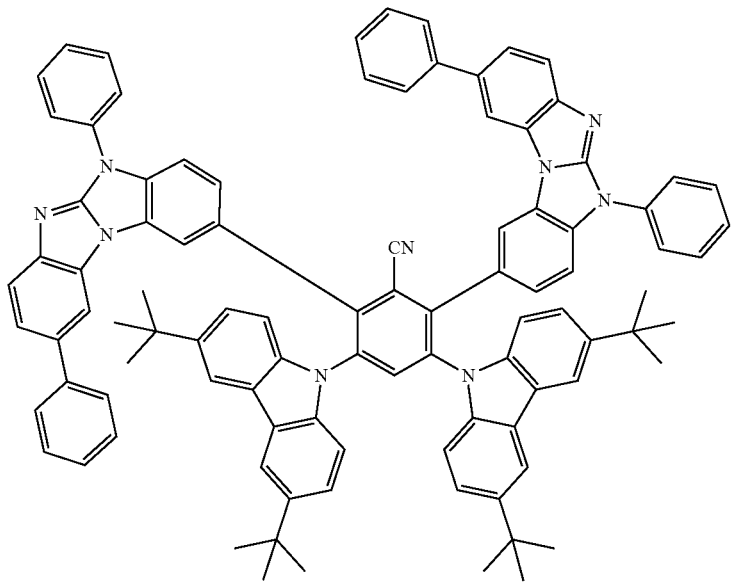
11
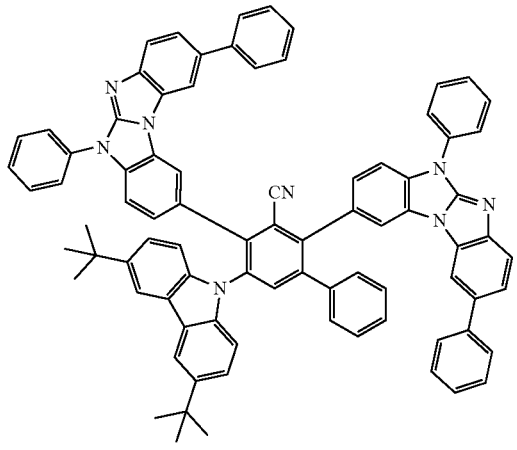
12
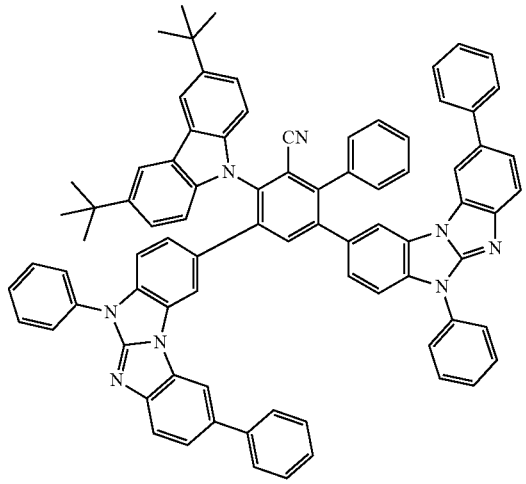
13

14
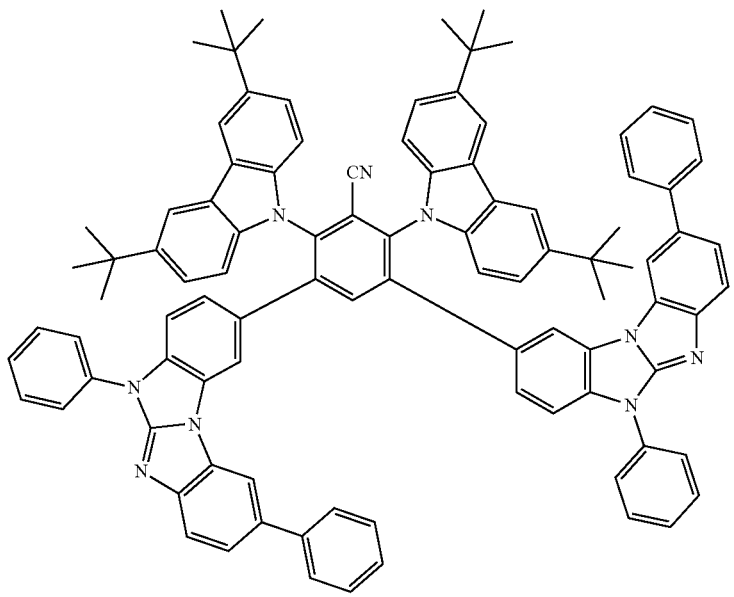
15
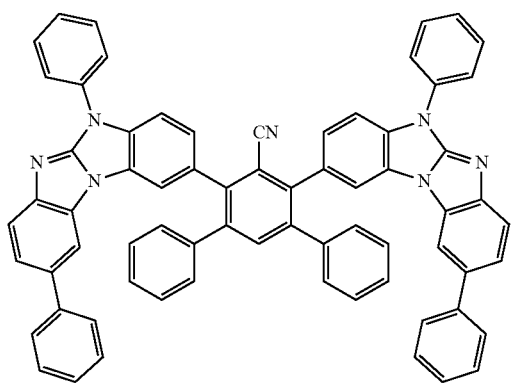
16
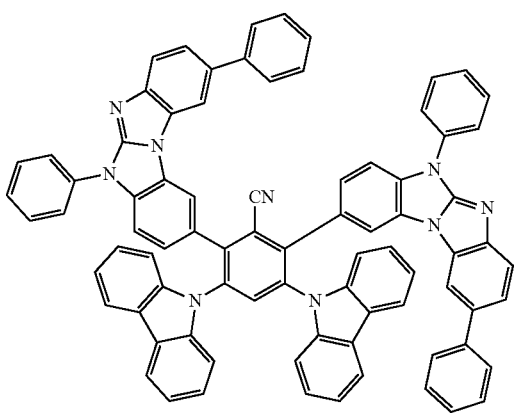
17
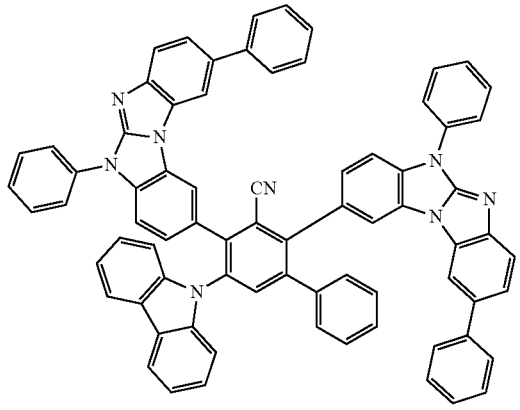
18
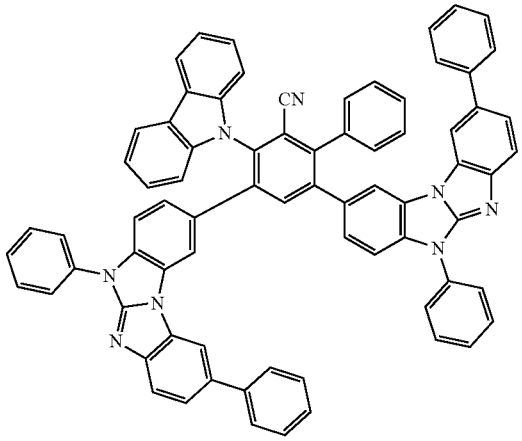

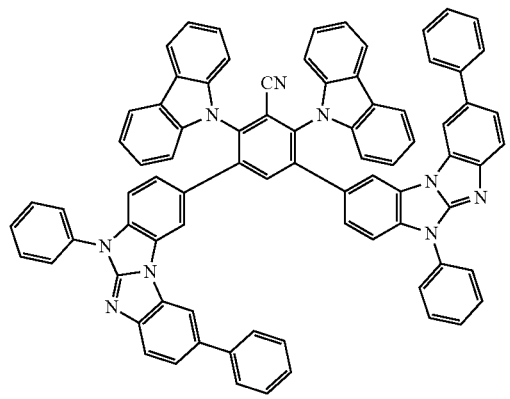
19
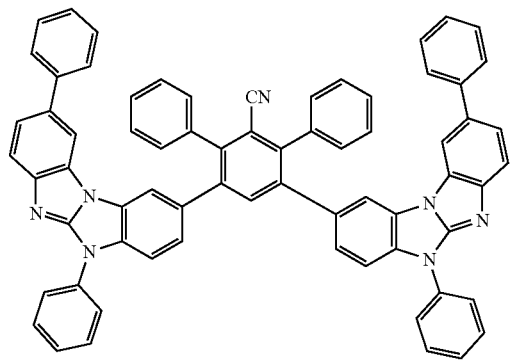
20
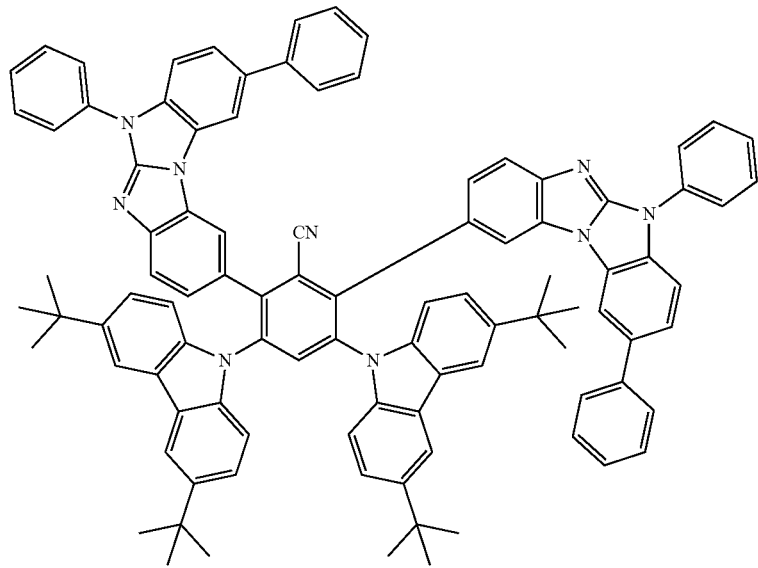
21
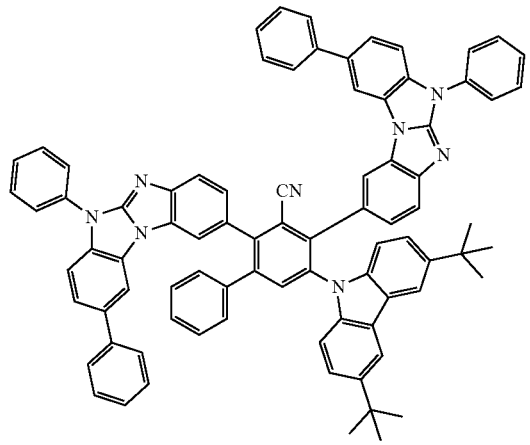
22
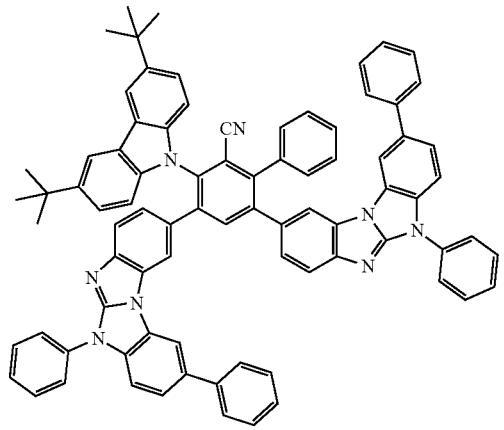
23

24
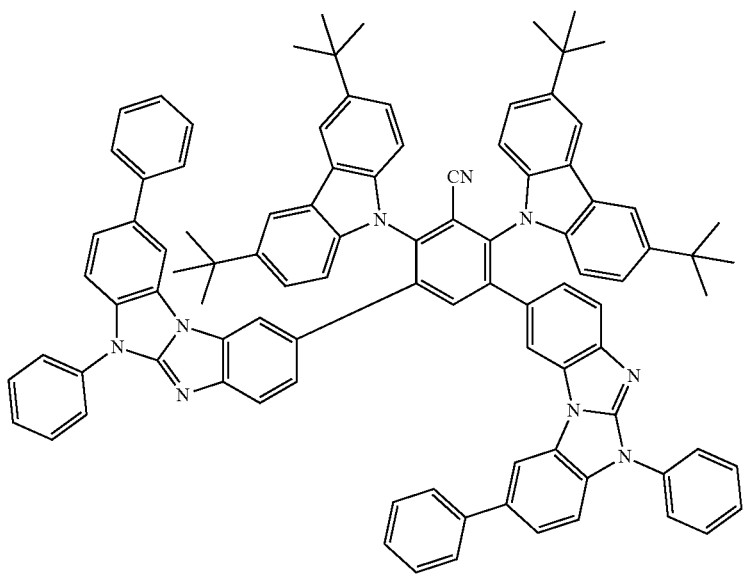
25
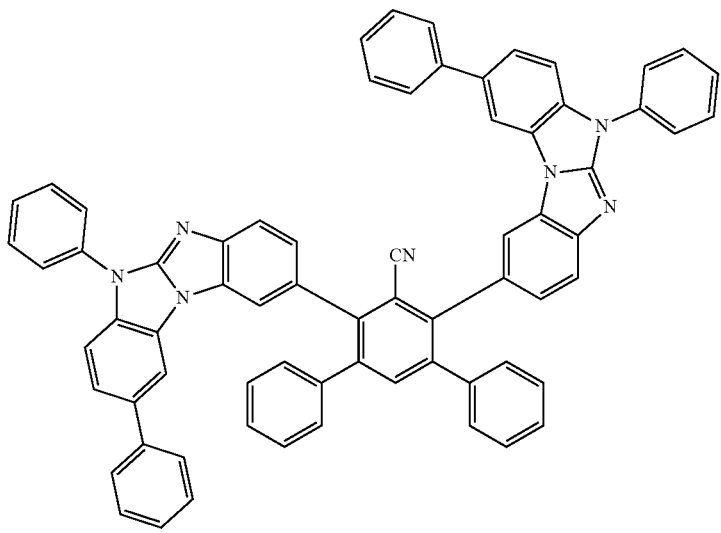
26
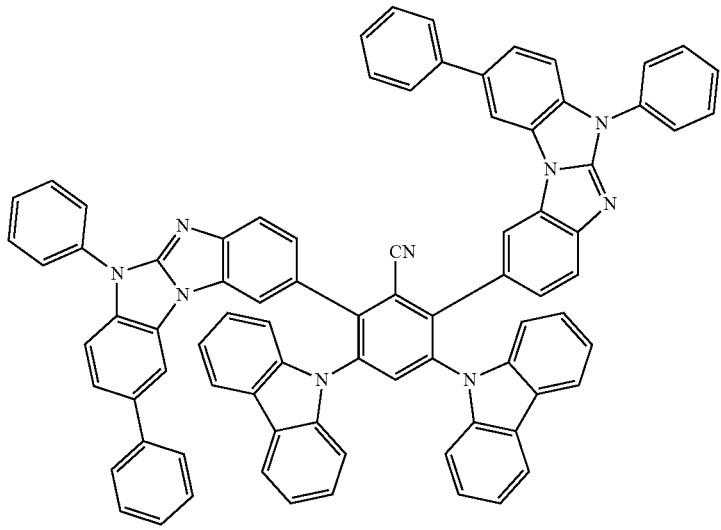

27
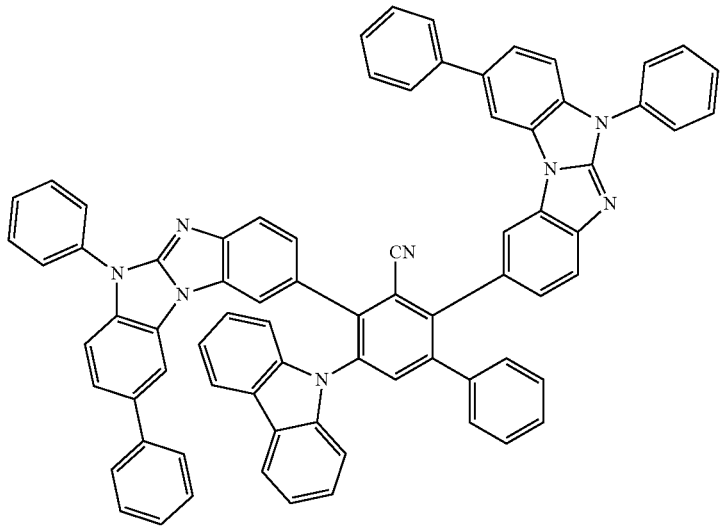
28
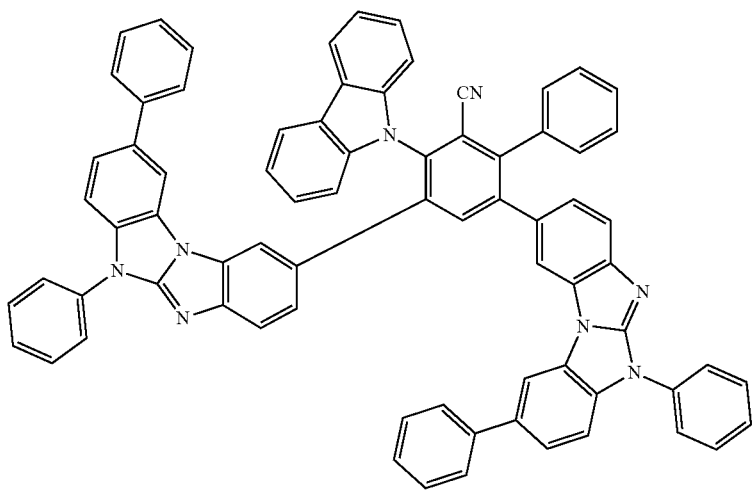
29
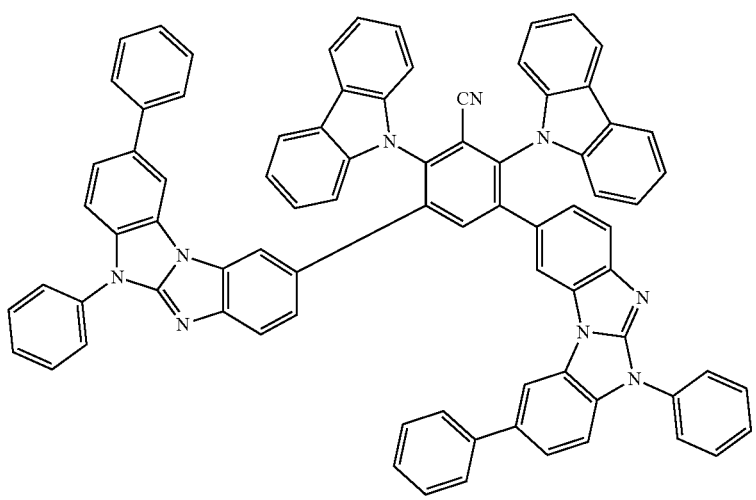

-continued
30
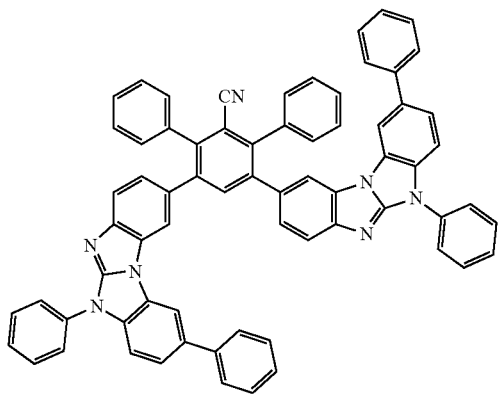
31
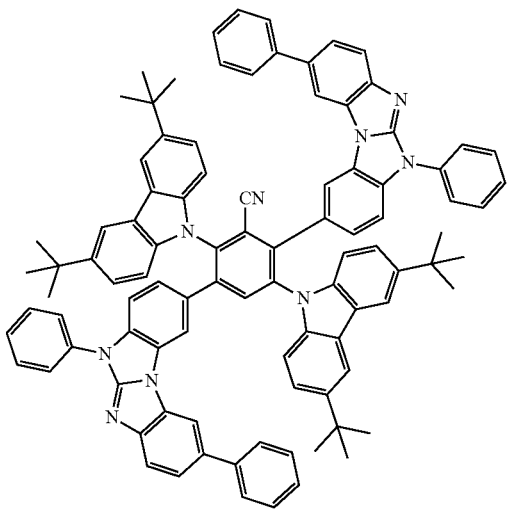
32
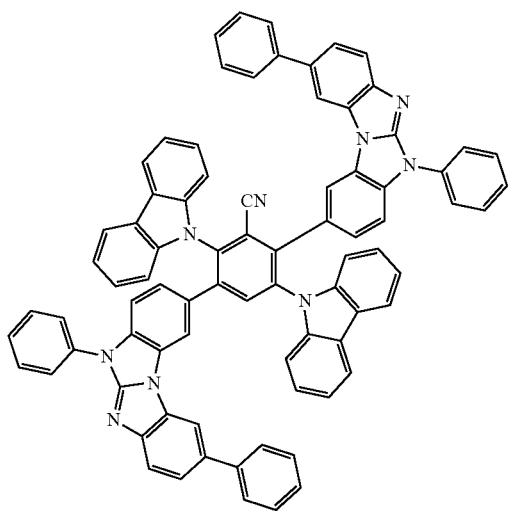
33
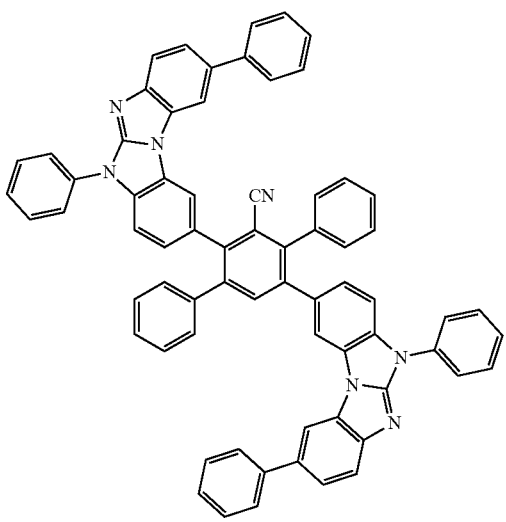
34
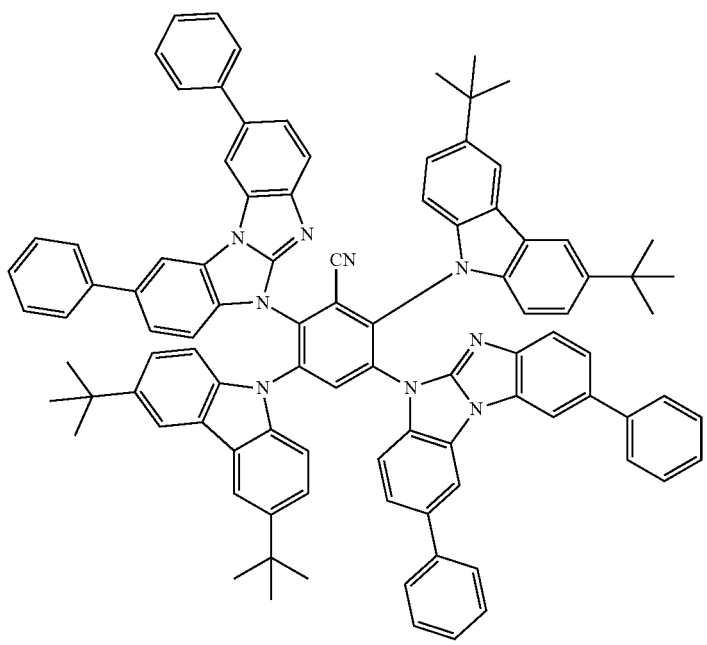

35
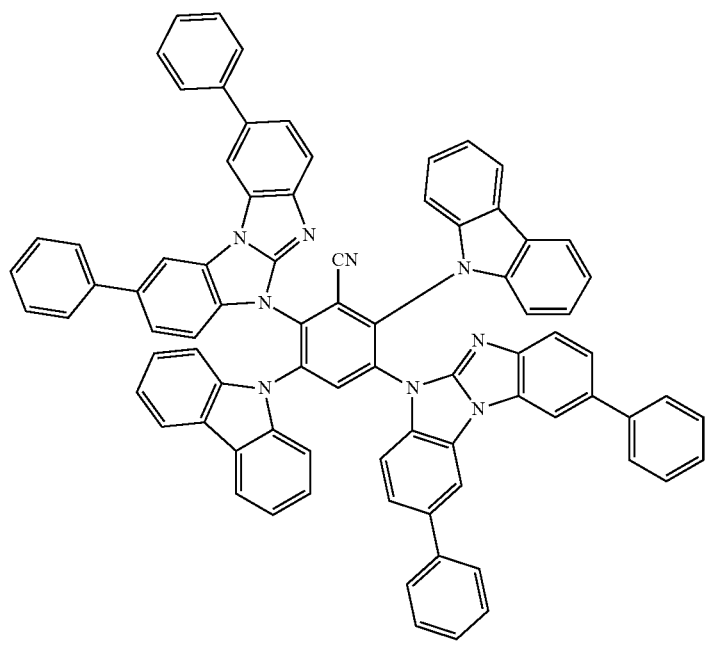
36
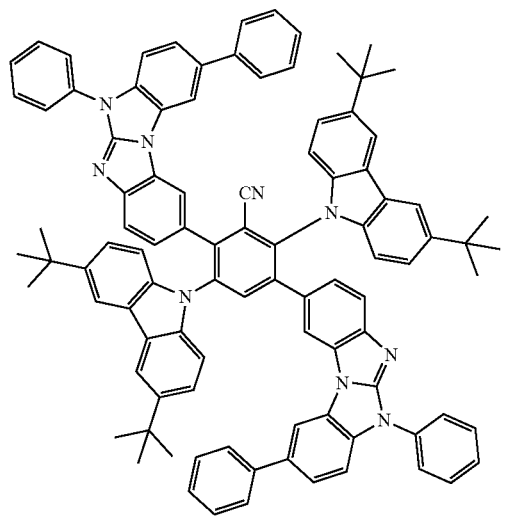
37
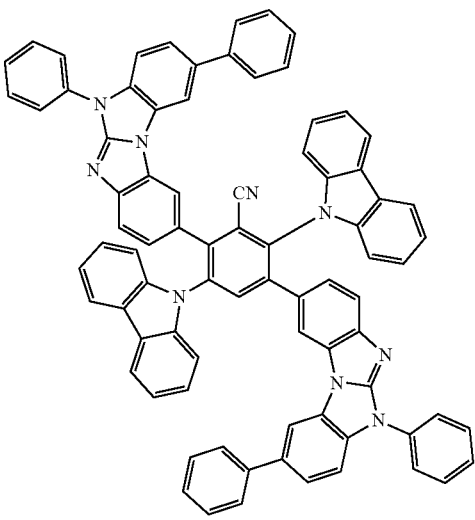
38
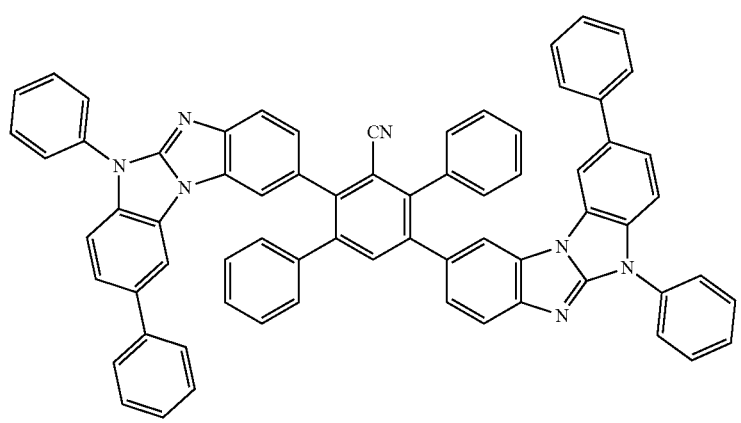

-continued

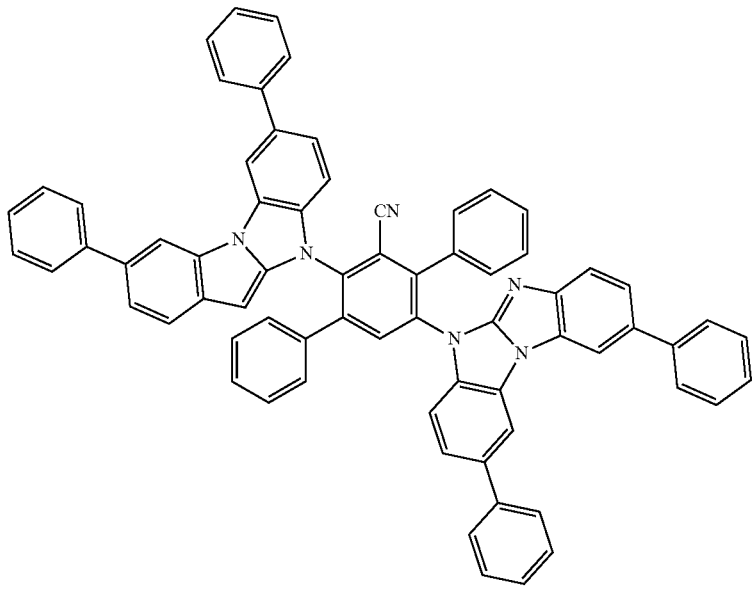

10. An organic light-emitting device comprising:
a first electrode;
a second electrode; and
an organic layer disposed between the first electrode and the second electrode and comprising an emission layer,
wherein the organic layer comprises the condensed-cyclic compound represented by any of Formulae 1-1 to 1-58 of claim 1.

11. The organic light-emitting device of claim 10, wherein the first electrode is an anode,
the second electrode is a cathode,
the organic layer comprises a hole transport region between the first electrode and the emission layer and an electron transport region between the emission layer and the second electrode,
the hole transport region comprises a hole injection layer, a hole transport layer, an electron blocking layer, or any combination thereof, and
the electron transport region comprises a hole blocking layer, an electron transport layer, an electron injection layer, or any combination thereof.

12. The organic light-emitting device of claim 10, wherein the emission layer comprises the condensed-cyclic compound.

13. The organic light-emitting device of claim 12, wherein a ratio of a fluorescent emission component to total emission components emitted from the emission layer is 90% or more.

14. The organic light-emitting device of claim 12, wherein the condensed-cyclic compound is a fluorescent emitter, and
a ratio of an emission component emitted from the condensed-cyclic compound to total emission components emitted from the emission layer is 80% or more.

15. Organic light-emitting device of claim 14, wherein the emission layer consists of the condensed-cyclic compound alone; or
the emission layer further comprises a host.

16. The organic light-emitting device of claim 12, wherein the emission layer comprises a host and a dopant,
the host comprises the condensed-cyclic compound,
an amount of the host is greater than an amount of the dopant, and
a ratio of an emission component of the dopant to total emission components emitted from the emission layer is 80% or more.

17. The organic light-emitting device of claim 12, wherein the emission layer comprises a host, an auxiliary dopant, and a dopant
the auxiliary dopant comprises the condensed-cyclic compound, and
a ratio of an emission component of the dopant to the total emission components emitted from the emission layer is 80% or more.

* * * * *